US010781227B2

(12) United States Patent
Gutsche et al.

(10) Patent No.: US 10,781,227 B2
(45) Date of Patent: Sep. 22, 2020

(54) APPLICATION OF METAL COMPLEXES IN ANTI-TUMOR AND ANTI-BACTERIAL THERAPY

(71) Applicant: biolitec Unternehmensbeteiligungs II AG, Vienna (AT)

(72) Inventors: Claudia S. Gutsche, Berlin (DE); Arno Wiehe, Berlin (DE); Benjamin F. Hohlfeld, Berlin (DE); Burkhard Gitter, Jena (DE); Volker Albrecht, Nuthetal (DE)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 0 days.

(21) Appl. No.: 16/266,509

(22) Filed: Feb. 4, 2019

(65) Prior Publication Data

US 2019/0241593 A1 Aug. 8, 2019

Related U.S. Application Data

(60) Provisional application No. 62/625,411, filed on Feb. 2, 2018.

(51) Int. Cl.
| | | |
|---|---|---|
| *C07F 15/00* | (2006.01) | |
| *C07F 15/06* | (2006.01) | |
| *C07F 15/02* | (2006.01) | |
| *C07F 15/04* | (2006.01) | |
| *C07F 1/08* | (2006.01) | |
| *C07F 3/06* | (2006.01) | |
| *C07F 5/00* | (2006.01) | |
| *C07F 19/00* | (2006.01) | |
| *A61K 47/64* | (2017.01) | |
| *A61K 41/00* | (2020.01) | |
| *A61P 35/00* | (2006.01) | |
| *A61P 31/04* | (2006.01) | |
| *A61P 19/02* | (2006.01) | |
| *C07F 1/00* | (2006.01) | |
| *A61K 49/00* | (2006.01) | |
| *C07F 3/00* | (2006.01) | |
| *A61K 31/555* | (2006.01) | |

(52) U.S. Cl.
CPC ........ *C07F 15/0053* (2013.01); *A61K 31/555* (2013.01); *A61K 41/0057* (2013.01); *A61K 47/64* (2017.08); *A61K 49/0017* (2013.01); *A61P 19/02* (2018.01); *A61P 31/04* (2018.01); *A61P 35/00* (2018.01); *C07F 1/005* (2013.01); *C07F 1/08* (2013.01); *C07F 3/003* (2013.01); *C07F 3/06* (2013.01); *C07F 5/003* (2013.01); *C07F 15/004* (2013.01); *C07F 15/008* (2013.01); *C07F 15/0093* (2013.01); *C07F 15/025* (2013.01); *C07F 15/045* (2013.01); *C07F 15/065* (2013.01); *C07F 19/005* (2013.01)

(58) Field of Classification Search
CPC .. C07F 15/0053; C07F 15/065; C07F 15/045; C07F 15/025; C07F 15/0093; C07F 15/008; C07F 15/004; C07F 1/08; C07F 5/003; C07F 19/005; A61P 19/02; A61P 35/00; A61P 31/04; A61K 47/64; A61K 41/0057
See application file for complete search history.

(56) References Cited

PUBLICATIONS

Pre-/post-functionalization in dipyrrin metal complexes—antitumor and antibacterial activity of their glycosylated derivatives Gutsche, Claudia S.; Graefe, Susanna; Gitter, Dalton Transactions, (2018), 47, (35), 12373-12384.*

* cited by examiner

*Primary Examiner* — Alexander R Pagano
*Assistant Examiner* — Ebenezer O Sackey
(74) *Attorney, Agent, or Firm* — BJ Associates; Bolesh J Skutnik

(57) ABSTRACT

The present invention provides biologically active compounds and methods to obtain biologically active compounds that can be used as photosensitizers for diagnostic and therapeutic applications, particularly for PDT of cancer, infections and other hyperproliferative diseases, fluorescence diagnosis and PDT treatment of non-tumorous indications such as arthritis, inflammatory diseases, viral or bacterial infections, dermatological, ophthalmological or urological disorders. As the compounds exhibit also toxicity against targets (tumor cells, bacteria, inflammation-related cells) without light these biologically active compounds may also be used for the light-independent treatment of such indications. Preferred embodiments of the present invention consist of methods to synthesize metal or half-metal complex structures incorporating one or more substituted 2,3,5,6-tetrafluorophenyl-dipyrromethene (2,3,5,6-tetrafluorophenyldipyrrin) units. These dipyrromethenes (dipyrrins) can carry a variety of different substituents in the 4-position enabling a fine tuning of their biological or amphiphilic/hydrophilic properties. Another object of the present invention is to provide amphiphilic compounds with a higher membrane affinity and increased efficacy.

21 Claims, 8 Drawing Sheets

APPLICATION OF METAL COMPLEXES IN ANTI-TUMOR AND ANTI-BACTERIAL THERAPY

RELATED CASE INFORMATION

This application claims the benefit of U.S. Provisional Application Ser. No. 62/625,411, filed Feb. 2, 2018, entitled "APPLICATION OF METAL COMPLEXES IN ANTI-TUMOR AND ANTI-BACTERIAL THERAPY", which are incorporated by reference herein in its entirety.

BACKGROUND OF THE INVENTION

Field of the Invention

The invention relates to the chemistry of biologically active compounds. More particularly it relates to certain metal complexes that can be used to treat tumorous diseases as well as bacterial infections and other diseases. The action of these metal complexes against tumor cells and bacteria may be intensified by light, thus they can also be used as photosensitizers for a wide range of light irradiation treatments such as photodynamic therapy of cancer, infections and other diseases.

Invention Disclosure Statement

Cancer is one of the main causes of death worldwide. Though many therapeutic approaches are known there is still need for new active substances and therapies that can be applied to tumors which cannot successfully be treated by conventional chemotherapeutics. One of those newer therapeutic approaches is photodynamic therapy (PDT).

PDT is now being explored for use in a variety of medical applications (Photodynamic therapy, basic principles and clinical applications. Eds. B. W. Henderson, Th. J. Dougherty, Marcel Dekker, 1992, New York), and particularly is a well-recognized treatment for the destruction of tumors (Photodynamic tumor therapy. $2^{nd}$ and $3^{rd}$ generation photosensitizers. Ed. J. G. Moser, Harwood Academic Publishers, 1998, Amsterdam). Photodynamic therapy uses light and a photosensitizer (a dye) to achieve its desired medical effect. A large number of naturally occurring and synthetic dyes have been evaluated as potential photosensitizers for PDT. Perhaps the most widely studied class of photosensitizers is tetrapyrrolic macrocyclic compounds. Among them, especially porphyrins and chlorins have been tested for their PDT efficacy. However, recently there has been increasing interest in new photosensitizer structures among them metal complexes e.g. ruthenium complexes (Y. K. Yan, M. Melchart, A. Habtemariam, P. J. Sadler, Organometallic chemistry, biology and medicine: ruthenium arene anticancer complexes, *Chem. Commun.* 2005, 4764-4776).

The photodynamic effect is only observed where the three necessary components, the photosensitizer, light and oxygen (which is present in the cells) are present at the same time (Photodynamic therapy, basic principles and clinical applications. Eds. B. W. Henderson, Th. J. Dougherty, Marcel Dekker, 1992, New York). This makes PDT in itself a local treatment which is opposed to the systemic action of chemotherapeutics. This localized treatment with PDT limits its efficacy mostly to localized tumors though recent reports also suggest a systemic, immunomodulating effect of PDT (J. W. Kleinovink, P. B. van Driel, T. J. Snoeks, N. Prokopi, M. F. Fransen, L. J. Cruz, L. Mezzanotte, A. Chan, C. W. Löwik, F. Ossendorp, Combination of Photodynamic Therapy and Specific Immunotherapy Efficiently Eradicates Established Tumors, *Clin. Cancer Res.* 2016, 22, 1459-1468).

Another field of application for PDT is the antibacterial PDT that is the application of photosensitizers and light against localized bacterial infections. Bacteria are generally divided into two main groups based on the different properties and construction of their outer membranes, i.e. Gram-positive and Gram-negative bacteria. For antibacterial PDT other dyes have been employed than for tumor therapy. Whereas for antitumor PDT amphiphilic photosensitizers have proven to be most effective, for antibacterial PDT usually more hydrophilic and water-soluble dyes have been employed (T. Maisch, Strategies to optimize photosensitizers for photodynamic inactivation of bacteria, *J. Photochem. Photobiol. B,* 2015, 150, 2-10). Specifically for Gram-negative bacteria water-soluble positively charged photosensitizers have been used (T. Maisch, Strategies to optimize photosensitizers for photodynamic inactivation of bacteria, *J. Photochem. Photobiol. B,* 2015, 150, 2-10).

OBJECTIVES AND BRIEF SUMMARY OF THE INVENTION

It is the aim of the present invention to provide biologically active compounds that can be used as photosensitizers for a wide range of applications including light irradiation treatments such as PDT of cancer, infections and other diseases. One of the limitations of current PDT is the localized effect of the treatment which is due to the fact that light has to be delivered to the treatment site. This could be overcome by compounds which act as photosensitizers but additionally exhibit a light-independent toxicity against e.g. tumor cells or bacteria. Therefore, the structures disclosed here are active as photosensitizers but may also be used for a systemic treatment due to their light-independent toxicity against e.g. tumor cells or bacteria. In addition due to their light-absorbing and light-emitting properties these compounds may also be employed for diagnostic purposes e.g. by detecting their fluorescence.

It is an objective of the present invention to use chemically stable metal or half-metal complexes for various medical applications such as photodynamic therapy.

It is yet an objective of the present invention to provide chemically stable metal or half-metal complexes for the treatment of tumorous and other diseases without having to administer light, thereby also enabling a systemic treatment.

It is yet an objective of the present invention to provide metal or half-metal complex structures incorporating one or more substituted 2,3,5,6-tetrafluorophenyl-dipyrromethene (2,3,5,6-tetrafluorophenyl-dipyrrin) units that can be used in the photodynamic therapy of tumors and other hyperproliferative diseases, dermatological disorders, viral or bacterial infections, ophthalmological disorders or urological disorders.

It is yet an objective of the present invention to provide metal or half-metal complex structures incorporating one or more substituted 2,3,5,6-tetrafluorophenyl-dipyrromethene (2,3,5,6-tetrafluorophenyl-dipyrrin) units that can be used in the therapy of tumors and other hyperproliferative diseases, dermatological disorders, viral or bacterial infections, ophthalmological disorders or urological disorders without the necessity to administer light.

It is yet an objective of the present invention to provide metal or half-metal complex structures incorporating one or more substituted 2,3,5,6-tetrafluorophenyl-dipyrromethene (2,3,5,6-tetrafluorophenyl-dipyrrin) units that can be used in light-based diagnostics of tumors and other hyperproliferative diseases, dermatological disorders, bacterial infections, ophthalmological disorders or urological disorders.

It is yet an objective of the present invention to provide metal or half-metal complex structures incorporating one or more substituted 2,3,5,6-tetrafluorophenyl-dipyrromethene (2,3,5,6-tetrafluorophenyl-dipyrrin) units that can be used for the fluorescence diagnosis and PDT treatment of a non-tumorous indication such as arthritis and similar inflammatory diseases.

It is yet an objective of the present invention to provide metal or half-metal complex structures incorporating one or more substituted 2,3,5,6-tetrafluorophenyl-dipyrromethene (2,3,5,6-tetrafluorophenyl-dipyrrin) units that can be used for the treatment of a non-tumorous indication such as arthritis and similar inflammatory diseases.

It is yet another object of the present invention to provide metal and half-metal complexes incorporating one or more substituted 3-nitrophenyl-dipyrromethene (3-nitrophenyl-dipyrrin) units.

It is another object of the present invention to provide highly amphiphilic compounds to be used in the PDT-treatment of tumors, dermatological disorders, viral or bacterial infections, ophthalmological disorders or urological disorders.

It is another object of the present invention to provide highly amphiphilic compounds to be used in the treatment of tumors, dermatological disorders, viral or bacterial infections, ophthalmological disorders or urological disorders without the necessity to administer light.

It is still another objective to provide pharmaceutically acceptable formulations for the biologically active compounds of the present invention such as a liposomal formulation to be injected avoiding undesirable effects like precipitation at the injection site or delayed pharmacokinetics of the compounds.

Briefly stated, the present invention provides biologically active compounds and methods to obtain biologically active compounds that can be used as photosensitizers for diagnostic and therapeutic applications, particularly for PDT of cancer, infections and other hyperproliferative diseases, fluorescence diagnosis and PDT treatment of non-tumorous indications such as arthritis, inflammatory diseases, viral or bacterial infections, dermatological, ophthalmological or urological disorders. As the compounds exhibit also toxicity against targets (tumor cells, bacteria, inflammation-related cells) without light these biologically active compounds may also be used for the light-independent treatment of such indications. Preferred embodiments of the present invention consist of methods to synthesize metal or half-metal complex structures incorporating one or more substituted 2,3,5,6-tetrafluorophenyl-dipyrromethene (2,3,5,6-tetrafluorophenyldipyrrin) units. These dipyrromethenes (dipyrrins) can carry a variety of different substituents in the 4-position enabling a fine tuning of their biological or amphiphilic/hydrophilic properties. Another object of the present invention is to provide amphiphilic compounds with a higher membrane affinity and increased efficacy.

The above and other objects, features and advantages of the present invention will become apparent from the following description read in conjunction with the accompanying drawings.

DETAILED DESCRIPTION OF PREFERRED EMBODIMENTS

Figure 1:
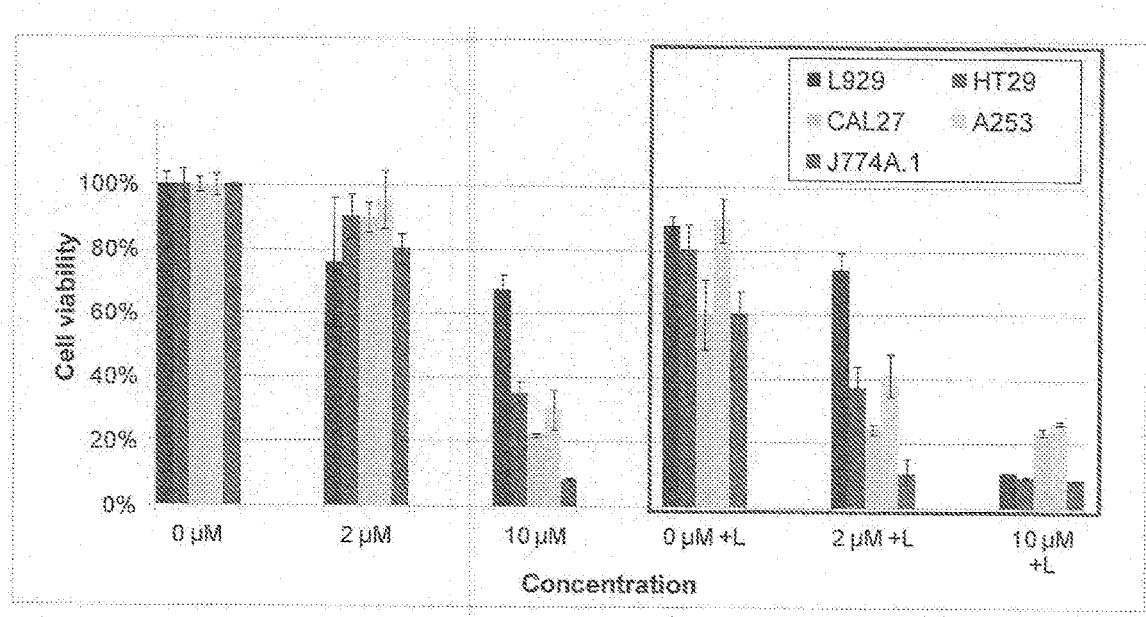
FIG. 1 illustrates the photodynamic activity ('+L' means phototoxicity) and the light independent antitumor activity of [bis(2,2'-bipyridyl(4-(prop-2-ynylamino)-2,3,5,6-tetrafluorophenyl)¬dipyrrinato)]-ruthenium(II) chloride.
Figure 2:
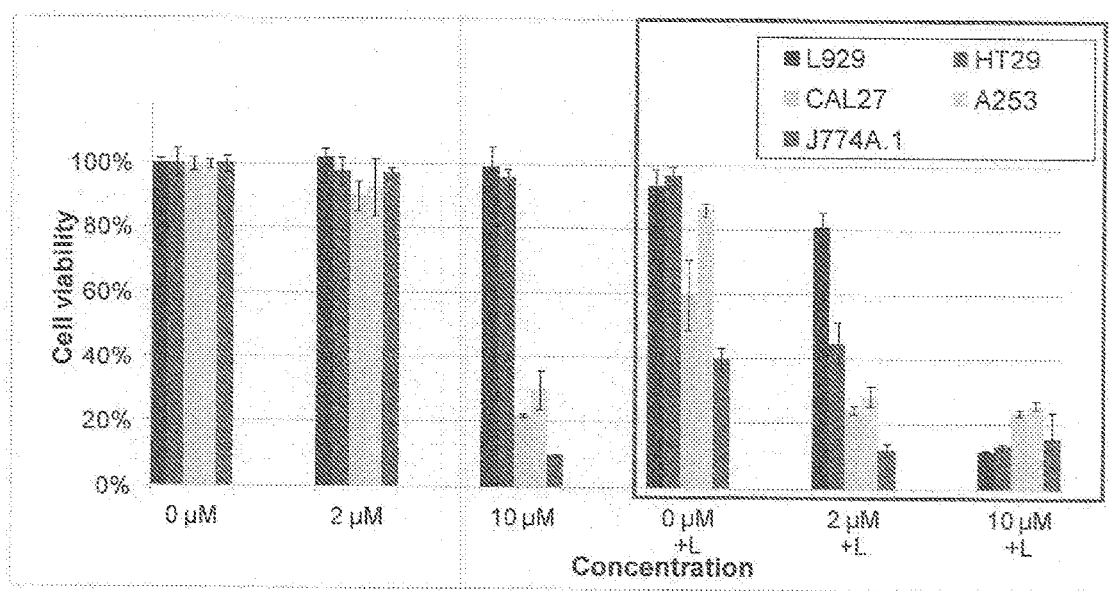
FIG. 2 illustrates the photodynamic activity ('+L' means phototoxicity) and the light independent antitumor activity of [bis(2,2'-bipyridyl(4-(prop-2-ynyloxy)-2,3,5,6-tetrafluorophenyl)¬dipyrrinato)]-ruthenium(II) chloride.
Figure 3:
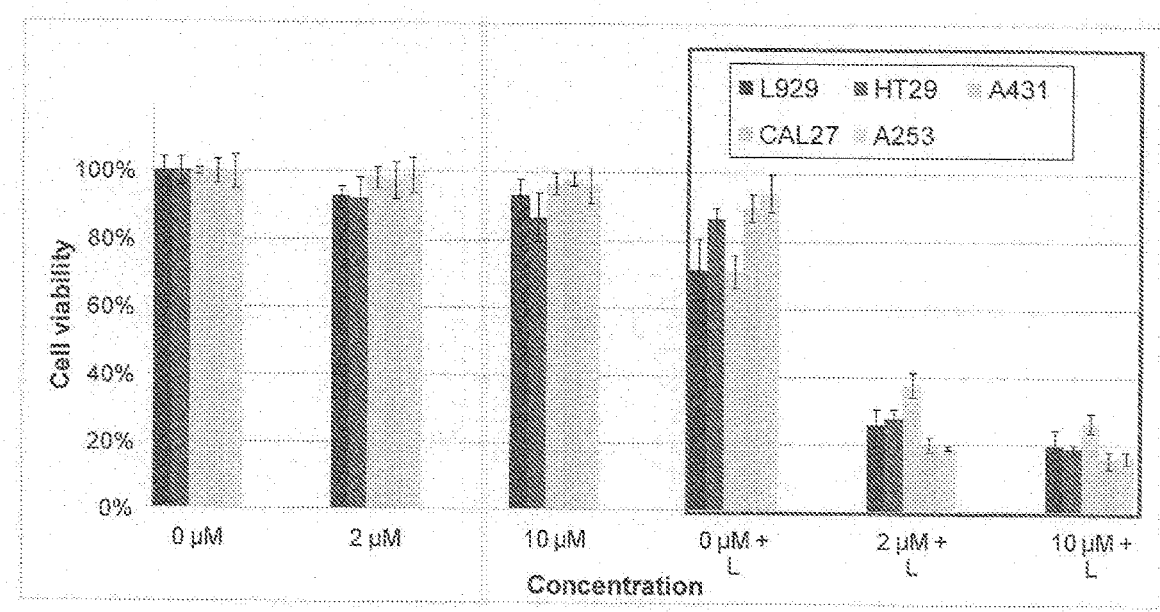
FIG. 3 illustrates the photodynamic activity ('+L' means phototoxicity) and the light independent antitumor activity of tris[5-(4-β-D-thioglucosyl)-2,3,5,6-tetrafluorophenyl) dipyrrinato gallium(III).
Figure 4:
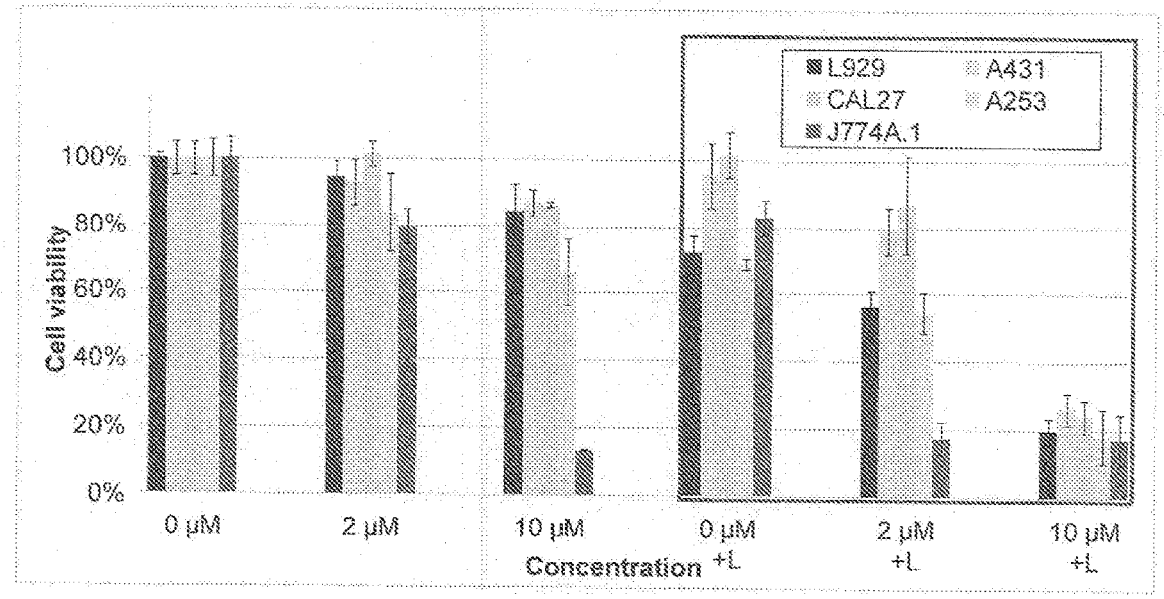
FIG. 4 illustrates the photodynamic activity ('+L' means phototoxicity) and the light independent antitumor activity of complex-BODIPY conjugate.
Figure 5:
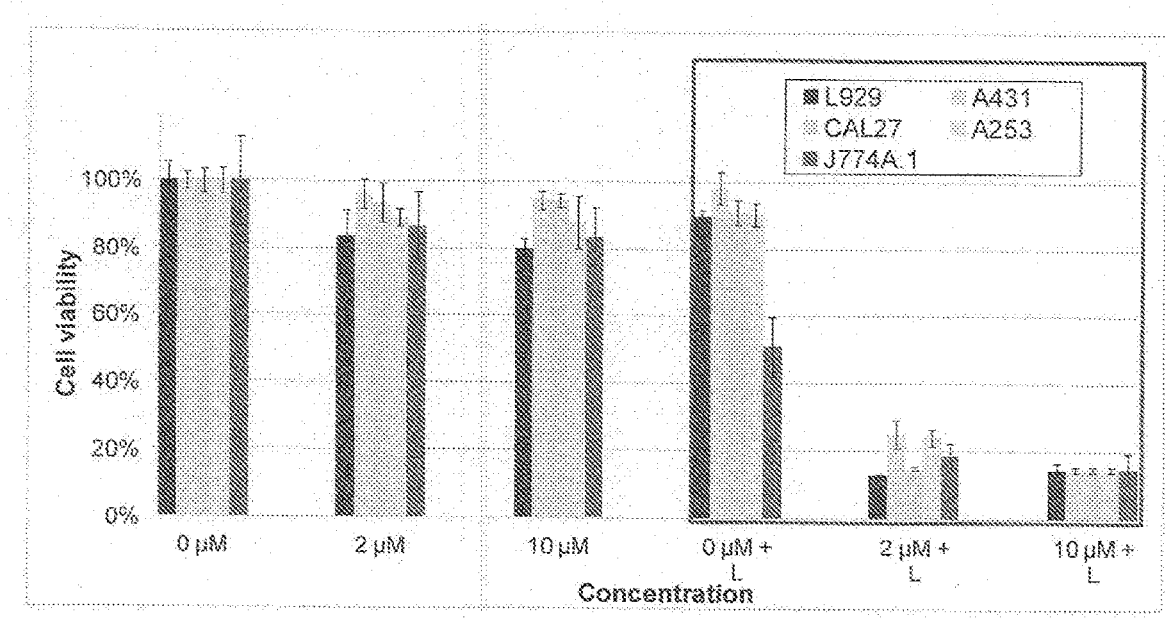
FIG. 5 illustrates the photodynamic activity ('+L' means phototoxicity) and the light independent antitumor activity of tris[5-(4-β-D-thiogalactosyl)-2,3,5,6-tetrafluorophenyl) dipyrrinato gallium(III).

The present invention provides biologically active compounds that can be used as photosensitizers for a wide range of light irradiation treatments such as PDT of cancer, hyperproliferative diseases, dermatological disorders, viral or bacterial infectious diseases, ophthalmological disorders and/or urological disorders. Due to their light-independent toxicity they can also be used for the therapy of such diseases without the necessity to administer light. The compounds provided by the present invention have the advantage that they are easily produced and characterized. The present invention allows the further functionalization to enhance their activity, stability or make new applications possible. Moreover, as the present invention provides methods to tailor amphiphilic compounds for desired applications, target tissue selectivity is increased and thus therapeutic efficacy. The present invention enhances the effectiveness of biologically active compounds in prior art allowing to combine PDT and conventional chemotherapeutic or antibacterial treatment, and enhances selectivity for target tissues over healthy surrounding tissues due to its tailored amphiphilicity and custom-made pharmacokinetic behavior depending on the particular application.

The biologically active compounds of the present invention that can be used for different medical indications and treatments, among them PDT, are metal and half-metal complexes containing one or more substituted dipyrromethene (dipyrrin) ligands. In addition, the invention extends their applications as the structures can be employed for fluorescence diagnosis and the treatment of non-tumorous indications such as arthritis and similar inflammatory diseases.

In order to obtain the novel compounds the present invention uses substituted dipyrromethene (dipyrrin) ligands and provides methods for preparation of the corresponding metal complexes. In one embodiment, these dipyrromethenes (dipyrrins) are obtained from the corresponding dipyrromethanes (dipyrranes) with suitable oxidizing agents (S. R. Halper, J. R. Stork, S. M. Cohen, Preparation and characterization of asymmetric a-alkoxy dipyrrin ligands and their metal complexes, *Dalton Trans.* 2007, 1067-1074).

Alternatively, a suitable dipyrromethene (dipyrrin) ligand, notably 2,3,4,5,6-pentafluorophenyl-dipyrromethene or 4-fluoro-3-nitrophenyl-dipyrromethene, is used to assemble the corresponding metal or half-metal complex. This complex is subsequently modified via nucleophilic aromatic substitution in the 4-position of the phenyl ring with a suitable nucleophile, specifically oxygen, nitrogen or sulfur nucleophiles (alcohols, amines, thiols).

In a specifically preferred embodiment of the present invention the nucleophile is a sugar moiety, e.g. galactosyl-thiol or glucosyl-thiol.

In yet another specifically preferred embodiment the nucleophile is a short-chain aminoalcohol (e.g. 2-aminoethanol) or propargylamine or propargylalcohol. The latter two allow for further modification of the final complex via the copper(I)-catalyzed 1,3-dipolar cycloaddition (CuAAC) or the strain-promoted alkyne-azide cycloaddition (SPAAC) (J.-F. Lutz, 1,3-Dipolar Cycloadditions of Azides and Alkynes: A Universal Ligation Tool in Polymer and Materials Science. *Angew. Chem. Int. Ed.* 2007, 46, 1018-1025; J. Dommerholt, S. Schmidt, R. Temming, L. J. A. Hendriks, F. P. J. T. Rutjes, J. C. M. van Hest, D. J. Lefeber, P. Friedl, F. L. van Delft, Readily Accessible Bicyclononynes for Bioorthogonal Labeling and Three-Dimensional Imaging of Living Cells. *Angew. Chem. Int. Ed.* 2010, 49, 9422-9425). These reactions may also be employed to connect the metal complexes of the present invention with suitable carrier systems such as hydrophilic polymers as exemplified in US patent publication US2016/62300230 and EP patent publication EP3210626A1.

The metal ions used for compiling the desired metal complexes with the dipyrromethene (dipyrrin) ligand(s) are chosen from the wide variety of divalent and trivalent metal ions.

In specifically preferred embodiments the divalent metal ion is selected from the group consisting of iron, ruthenium, cobalt, nickel, copper, platinum, and zinc; the trivalent metal ion is selected from the group consisting of iron, cobalt, rhodium, ruthenium, iridium, indium, gallium.

The half-metal to be used in the present invention is boron as a boron-difluoride ligand. In this case the corresponding boron dipyrromethene is easily obtained by treating the dipyrromethane (dipyrrane) with a suitable oxidizing agent followed by treatment with a base and boron-trifluoride etherate (A. Treibs, F. H. Kreuzer, Difluorboryl-Komplexe von Di- and Tripyrrylmethenen, *Justus Liebigs Ann. Chem.* 1968, 718, 208-223).

In another embodiment of the invention the dipyrromethene (dipyrrin) ligand is combined with other ligands, preferably bipyridyl ligands, and a suitable metal ion, e.g. ruthenium. The dipyrromethene ligand employed for complex formation may either be a substituted 2,3,5,6-tetrafluorophenyl-dipyrromethene (2,3,5,6-tetrafluorophenyldipyrrin) [or a substituted 3-nitrophenyl-dipyrromethene (3-nitrophenyl-dipyrrin)] in which case the substituted complex is directly obtained or it may be 2,3,4,5,6-pentafluorophenyl-dipyrromethene or 4-fluoro-3-nitrophenyl-dipyrromethene whereby a complex is obtained suitable for post-functionalization with e.g. oxygen, nitrogen or sulfur nucleophiles.

Acceptable starting materials for the synthesis of the dipyrromethene-containing complexes which are the subject of the present invention are dipyrromethanes (dipyrranes) which are readily accessible from the condensation reaction of pyrroles and aldehydes (C.-H. Lee, J. S. Lindsey, One-Flask Synthesis of Meso-Substituted Dipyrromethanes and Their Application in the Synthesis of Trans-Substituted Porphyrin Building Blocks, *Tetrahedron* 1994, 50, 11427-11440). Suitable methods for this condensation have long been known in the art (C.-H. Lee, J. S. Lindsey, One-Flask Synthesis of Meso-Substituted Dipyrromethanes and Their Application in the Synthesis of Trans-Substituted Porphyrin Building Blocks, *Tetrahedron* 1994, 50, 11427-11440). The dipyrromethane (dipyrrane) can then be modified with nucleophiles according to the literature (H. R. A. Golf, H.-U. Reissig, A. Wiehe, Nucleophilic Substitution on (Pentafluorophenyl)dipyrromethane: A New Route to Building Blocks for Functionalized BODIPYs and Tetrapyrroles, *Org. Lett.* 2015, 17, 982-985). The dipyrromethanes (dipyrranes)—whether modified with nucleophiles of not—are then oxidized to the corresponding dipyrromethenes (dipyrrins) using suitable oxidizing agents like e.g. p-chloranil or DDQ (H. R. A. Golf, H.-U. Reissig, A. Wiehe, Nucleophilic Substitution on (Pentafluorophenyl)dipyrromethane: A New Route to Building Blocks for Functionalized BODIPYs and Tetrapyrroles, *Org. Lett.* 2015, 17, 982-985). If the oxidation is followed by base treatment and subsequent reaction with boron trifluoride etherate the boron dipyrromethenes (BODIPYs) are obtained (A. Treibs, F. H. Kreuzer, Difluorboryl-Komplexe von Di- and Tripyrrylmethenen, *Justus Liebigs Ann. Chem.* 1968, 718, 208-223).

The synthesis of compounds which are subject of the present invention is illustrated with the examples given below.

Example 1 shows the synthesis of dipyrromethene complexes with divalent metal ions.

Example 2 shows the synthesis of dipyrromethene complexes with trivalent metal ions. It is shown that the complexes are either obtained by assembling the metal complex with the basic dipyrromethene and then functionalizing it with a suitable nucleophile, or the complex is directly synthesized with the functionalized dipyrrin. Further it is shown that alkyne-substituted metal complexes thus obtained can be connected to other active units (e.g. boron dipyrromethenes), e.g. via click reactions.

Example 3 shows the synthesis of ruthenium complexes involving one dipyrromethene and two bipyridyl ligands. In this case again the complex is assembled using the basic dipyrromethene which is then functionalized, or the complex is functionalized with suitable nucleophiles. Further it is shown that alkyne-substituted or azide-substituted metal complexes thus obtained can be connected to other active units (e.g. boron dipyrromethenes, sugar moieties), e.g. via click reactions.

The specifically substituted metal and half-metal complexes produced according to the present invention are suitable to be used for the chemotherapy of cancer and other (hyper) proliferative diseases and infections as well as for the photodynamic therapy of those diseases, infections and conditions.

Treatment is accomplished by first incorporating the derivatives into a pharmaceutically acceptable application vehicle (e.g. ethanolic solution, liposomal formulation, or another pharmaceutical formulation) for delivery of the derivatives to a specific treatment site. After administering the derivatives in the vehicle to a treatment area, sufficient time is allowed so that the complexes preferentially accumulate in the diseased tissue and exert their effect. In case of PDT treatment, the treatment area is irradiated with light of a proper wavelength and sufficient power to activate the metal complexes to induce necrosis or apoptosis in the cells of said diseased tissue. Due to their amphiphilic nature, the chemically stable metal complexes of the present invention can be prepared in various pharmaceutically acceptable and active preparations for different administration methods, e.g. injections. In one embodiment such amphiphilic compounds are formulated into liposomes. This liposomal formulation can then be injected avoiding undesirable effects such as precipitation at the injection site or delayed pharmacokinetics.

Determination of dark toxicity (DT) and phototoxicity (example 4) of the metal complexes of the present invention in cell culture experiments with the HT 29 tumor cell line and other cell lines shows the excellent properties of the compounds for use in PDT.

Moreover, the figures in example 4 show the light-independent toxicity (chemotherapeutic effect) of metal complexes according to the current invention in selected cell lines. It is also exemplified that complexes show a higher activity against the tumor cell lines compared to the conventional fibroblast cell line illustrating the high specific activity against tumor cell lines.

As another object of the present invention is to use the disclosed metal complexes in the diagnosis and treatment of arthritis and similar inflammatory diseases, the data presented in example 4 also show the results of the photodynamic treatment in a model cell line especially relevant for arthritis (J774A.1, a macrophage cell line) with compounds of the present invention.

Another object of the present invention is to provide compounds that can be used to treat bacterial infections. The figures in example 5 illustrate the effect of metal complexes according to the present invention against bacteria, the Gram-positive germ *S. aureus* as well as the Gram-negative *Acinetobacter baumannii* DSM30007 and *Klebsiella pneumoniae* DSM30104. Again it can be seen from the examples that selected compounds show a high antibacterial activity even in the absence of light exemplifying their principal suitability for a systemic treatment.

The following examples are presented to provide those of ordinary skill in the art with a full and illustrative disclosure and description of how to make the metal and half-metal complexes of the invention and show their chemotherapeutic and photodynamic activity and are not intended to limit the scope of what the inventor regards as the invention. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

EXAMPLES

Reagents and solvents were used as purchased from commercial suppliers. Thin layer chromatography (TLC) was performed using Merck silica gel 60 (with fluorescence indicator) pre-coated on aluminium sheets. Flash chromatography was carried out using Fluka silica gel 60, 0.040-0.063 mm (230-400 mesh). $^1$H, $^{19}$F and $^{13}$C NMR spectra were recorded in $CDCl_3$, $(CD_3)_2CO$, $CD_3OD$ or $(CD_3)_2SO$ on Bruker AC 250, AC 500, ECX 400 or AMX 500 instruments. Chemical shifts δ are given in ppm relative to TMS as internal standard or relative to the resonance of the residual solvent peak, J values are given in Hz. Mass spectra were recorded on Varian MAT 771, Varian IonSpec QFT-7 or Agilent 6210 ESI-TOF instruments. Electronic absorption spectra were recorded on a Specord S300 (Analytik Jena) spectrophotometer using dichloromethane or acetone as solvent. Fluorescence spectra were recorded with a Jasco FP-6500 spectrofluorimeter. Elemental analyses were performed with a VARIO EL device. Para-alkoxy substituted (H. R. A. Golf, H.-U. Reissig, A. Wiehe, Nucleophilic Substitution on (Pentafluorophenyl)-dipyrromethane: A New Route to Building Blocks for Functionalized BODIPYs and Tetrapyrroles, *Org. Lett.* 2015, 17, 982-985) and para-amino substituted dipyrranes (C. S. Gutsche, M. Ortwerth, S. Grafe, K. J. Flanagan, M. O. Senge, H.-U. Reissig, N. Kulak, A. Wiehe, Nucleophilic Aromatic Substitution on Pentafluorophenyl-Substituted Dipyrranes and Tetrapyrroles as a Route to Multifunctionalized Chromophores for Potential Application in Photodynamic Therapy, *Chem. Eur. J.* 2016, 22, 13953-13964) and 5-(pentafluorophenyl)dipyrromethene [5-(pentafluorophenyl)dipyrrin] were prepared according to the literature (L. Yu, K. Muthukumaran, I. V. Sazanovich, C. Kirmaier, E. Hindin, J. R. Diers, P. D. Boyle, D. F. Bocian, D. Holten, J. S. Lindsey, Excited-State Energy-Transfer Dynamics in Self-Assembled Triads Composed of Two Porphyrins and an Intervening Bis(dipyrrinato)metal Complex, *Inorg. Chem.* 2003, 42, 6629-6647).

Example 1

Preparation of Dipyrromethene Ligands

Preparation of Bis(Dipyrrinato) Metal Complexes

5-[(4-butyloxy)-2,3,5,6-tetrafluorophenyl)dipyrromethene

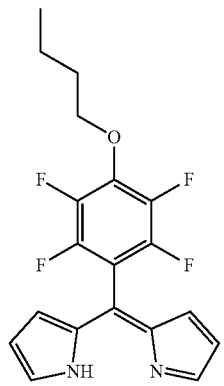 [SMILES: CCCCOc1c(F)c(F)c(/C(=C2\C=CC=N2)c2ccc[nH]2)c(F)c1F]

5-(Pentafluorophenyl)dipyrromethane (654 mg, 1.78 mmol) was dissolved in THF (10 mL), DDQ (526 mg, 2.32 mg, 1.3 eq) was added and the mixture was stirred for 15 min at room temperature (rt). The crude product was filtered through silica gel, evaporated to dryness and purified by column chromatography (silica gel, DCM) to obtain the product as yellow oil (260 mg, 40%).

$^1$H NMR (400 MHz, CDCl$_3$): δ=1.01 (t, J=7.4 Hz, 3H, CH$_3$), 1.50-1.60 (m, 2H, CH$_2$), 1-78-1.88 (m, 2H, CH$_2$), 4.34 (t, J=6.5 Hz, 2H, CH$_2$), 6.41 (dd, J=4.2, 1.4 Hz, 2H, H$_{pyrrole}$), 6.52 (d, J=4.2 Hz, 2H, H$_{pyrrole}$), 7.63-7.65 (m, 2H, H$_{pyrrole}$) ppm.

$^{13}$C NMR (126 MHz, CDCl$_3$): δ=13.79 (CH$_3$), 18.89 (CH$_2$), 32.06 (CH$_2$), 75.22 (CH$_2$), 109.54 (t, J$_{C-F}$=19.2 Hz, Ar—C$_{ipso}$), 118.74 (C$_{pyrrole}$), 127.27 (C$_{pyrrole}$), 138.42 (t, J$_{C-F}$=11.9 Hz, Ar—C$_{para}$) 145.09 (C$_{pyrrole}$), 140.95 (dd, J$_{C-F}$=248.5, 15.0 Hz, Ar—C$_{meta}$), 145.21 (d, J$_{C-F}$=249.0 Hz, Ar—C$_{ortho}$) ppm.

$^{19}$F NMR (376 MHz, CDCl$_3$): δ=−156.54 (m$_c$, J=14.3 Hz, 2F, Ar—F$_{meta}$), −140.42 (m$_c$, J=22.6, 7.9 Hz, Ar—F$_{ortho}$) ppm.

HRMS (ESI-TOF): m/z calc. for C$_{19}$H$_{17}$F$_4$N$_2$O$^+$ [M+H]$^+$ 365.1272, found 365.1277.

UV/VIS (DCM): λ$_{max}$/nm [log(ε/L mol$^{-1}$ cm$^{-1}$)]=431 (4.62) nm.

5-[(4-prop-2-ynyloxy)-2,3,5,6-tetrafluorophenyl] dipyrromethene

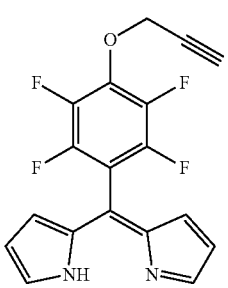 [SMILES: C#CCOc1c(F)c(F)c(/C(=C2\C=CC=N2)c2ccc[nH]2)c(F)c1F]

A mixture of 5-(pentafluorophenyl)dipyrromethane (568 mg, 1.63 mmol) and DDQ (481 mg, 2.11 mmol, 1.3 eq) in THF (10 mL) was stirred for 15 min at rt. The mixture was filtered through silica gel, evaporated to dryness and purified by column chromatography (silica gel, DCM/n-hexane=1:1) to obtain the product as yellow oil (250 mg, 44%).

$^1$H NMR (400 MHz, CDCl$_3$): δ=2.64 (t, J=2.4 Hz, 1H, CH), 4.98 (d, J=2.4 Hz, 2H, CH$_2$), 6.41 (dd, 4.2, 1.4 Hz, 2H, H$_{pyrrole}$), 6.51 (d, J=4.1 Hz, 2H, H$_{pyrrole}$), 7.64-7.66 (m, 2H, H$_{pyrrole}$) ppm.

$^{13}$C NMR (126 MHz, CDCl$_3$): δ=61.77 (CH$_2$), 76.92 (C≡CH), 77.62 (C≡CH), 111.15 (t, J$_{C-F}$=19.1 Hz, Ar—C$_{ipso}$), 118.84 (C$_{pyrrole}$), 127.20 (C$_{pyrrole}$), 136.20 (m, Ar—C$_{para}$) 140.55 (C$_{meso}$), 141.40 (d, J$_{C-F}$=265.5 Hz, Ar—C$_{meta}$), 144.83 (d, J$_{C-F}$=255.3 Hz, Ar—C$_{ortho}$), 145.22 (C$_{pyrrole}$)

$^{19}$F NMR (376 MHz, CDCl$_3$): δ=−155.01 (m$_c$, J=22.7, 8.4 Hz, 2F, Ar—F$_{meta}$), −139.89 (m$_c$, J=22.4, 8.3 Hz, 2F, Ar—F$_{ortho}$) ppm.

HRMS (ESI-TOF): m/z calc. for C$_{18}$H$_{11}$F$_4$N$_2$O$^+$ [M+H]$^+$ 347.0802, found 347.0809.

UV/VIS (DCM): λ$_{max}$/nm [log(ε/L mol$^{-1}$ cm$^{-1}$)]=431 (4.62) nm.

5-[4-(N-prop-2-ynylamino)-2,3,5,6-tetrafluorophenyl]dipyrromethene

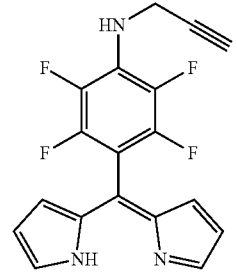 [SMILES: C#CCNc1c(F)c(F)c(/C(=C2\C=CC=N2)c2ccc[nH]2)c(F)c1F]

5-(Pentafluorophenyl)dipyrromethane (913 mg, 2.63 mmol) was dissolved in THF (10 mL), DDQ (776 mg, 3.40 mmol, 1.3 eq) was added and the mixture stirred for 15 min at r t. The mixture was filtered through silica gel, evaporated to dryness and purified by column chromatography (silica gel, DCM/n-hexane=1:1) to obtain the product as yellow oil (640 mg, 70%).

$^1$H NMR (400 MHz, CDCl$_3$): δ=1.26 (t, J=7.2 Hz, 1H, C≡CH), 4.20-4.25 (m, 2H, CH$_2$), 6.40 (dd, J=4.20, 1.4 Hz, 2H, H$_{pyrrole}$), 6.56 (d, J=4.2 Hz, 2H, H$_{pyrrole}$), 7.62-7.62 (m, 2H, H$_{pyrrole}$) ppm.

$^{13}$C NMR (126 MHz, CDCl$_3$): δ=35.30 (CH$_2$), 72.79 (C≡CH), 79.92 (C≡CH), 105.03 (m, Ar—C$_{ipso}$), 118.16 (C$_{pyrrole}$), 127.39 (C$_{pyrrole}$), 140.54 (C$_{meso}$), 144.78 (C$_{pyrrole}$) ppm.

$^{19}$F NMR (376 MHz, CDCl$_3$): δ=−158.33 (m$_c$, J=21.9, 7.7 Hz, 2F, Ar—F$_{meta}$), −140.95 (dd, J=21.2, 7.1 Hz, 2F, Ar—F$_{ortho}$) ppm.

HRMS (ESI-TOF): m/z calc. for C$_{18}$H$_{12}$F$_4$N$_3$$^+$ [M+H]$^+$ 346.0962, found 346.0973.

UV/VIS (DCM): λ$_{max}$/nm [log(ε/L mol$^{-1}$ cm$^{-1}$)]=432 (4.45) nm.

5-[(4-prop-enyloxy)-2,3,5,6-tetrafluorophenyl]dipyrromethene

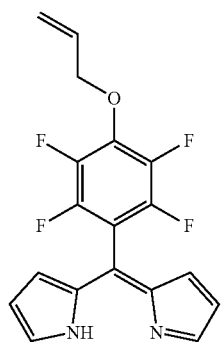 [SMILES: C=CCOc1c(F)c(F)c(/C(=C2\C=CC=N2)c2ccc[nH]2)c(F)c1F]

5-(Pentafluorophenyl)dipyrromethane (372 mg, 1.07 mmol) was dissolved in THF (10 mL), DDQ (315 mg, 1.38 mmol, 1.3 eq) was added and the mixture was stirred for 15 min at rt. The mixture was filtered through silica gel and evaporated to dryness. The crude product was purified by column chromatography (silica gel, DCM/n-hexane=3:1) to obtain the product as yellow oil (300 mg, 80%).

$^1$H (400 MHz, CDCl$_3$): δ=4.83 (d, J=6.1 Hz, 2H, CH$_2$), 5.37 (dd, J=10.3, 1.2 Hz, 1H, C=CH$_2$), 5.46 (dd, J=17.1, 1.4 Hz, 1H, C=CH$_2$), 6.05-6.15 (m, 1H, CH), 6.41 (dd, J=4.2, 1.4 Hz, 2H, H$_{pyrrole}$), 6.50 (d, J=3.6 Hz, 2H, H$_{pyrrole}$), 7.64 (t, J=1.1 Hz, 2H, H$_{pyrrole}$) ppm.

$^{13}$C NMR (126 MHz, CDCl$_3$): δ=75.45 (CH$_2$), 118.77 (C$_{pyrrole}$), 110.01 (t, J$_{C-F}$=19.2 Hz, Ar—C$_{ipso}$), 120.31 (C=CH$_2$), 127.11 (C$_{pyrrole}$), 132.16 (CH), 137.43 (C$_{meso}$), 137.34 (m, Ar—C$_{para}$), 141.01 (dd, J$_{C-F}$=248.6, 15.2 Hz, Ar—C$_{meta}$), 144.93 (d, J$_{C-F}$=243.9 Hz, Ar—C$_{ortho}$), 145.06 (C$_{pyrrole}$) ppm.

$^{19}$F NMR (376 MHz, CDCl$_3$): δ=−155.08 (m$_c$, J=22.4, 8.1 Hz, 2F, Ar—F$_{meta}$), −140.28 (m$_c$, J=21.9, 7.8 Hz, 2F, Ar—F$_{ortho}$) ppm.

HRMS (ESI-TOF): m/z calc for C$_{18}$H$_{13}$F$_4$N$_2$O$^+$ [M+H]$^+$ 349.0959, found 349.1002.

UV/VIS (DCM): λ$_{max}$/nm [log(ε/L mol$^{-1}$ cm$^{-1}$)]=430 (4.65) nm.

5-[(4-N-prop-2-enylamino)-2,3,5,6-tetrafluorophenyl]dipyrromethene

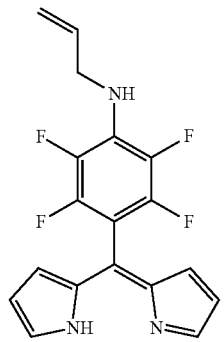 [SMILES: C=CCNc1c(F)c(F)c(/C(=C2\C=CC=N2)c2ccc[nH]2)c(F)c1F]

PFP-dipyrromethane (320 mg, 0.91 mmol) was dissolved in THF (10 mL), DDQ (270 mg, 1.19 mmol, 1.3 eq) was added and the mixture stirred for 15 min at rt. The mixture was filtered through silica gel, evaporated and purified by column chromatography (silica gel, DCM) to obtain the product as yellow oil (122 mg, 38%).

$^1$H NMR (400 MHz, CDCl$_3$): δ=4.07-4.11 (m, 2H, CH$_2$), 5.23 (d, J=10.3 Hz, 1H, C=CH$_2$), 5.31 (d, J=17.0 Hz, 1H, C=CH$_2$), 5.90-6.00 (m, 1H, CH), 6.39 (dd, J=4.2, 1.0 Hz, 2H, H$_{pyrrole}$), 6.57 (d, J=4.1 Hz, 2H, H$_{pyrrole}$), 7.60-7.64 (m, 2H, H$_{pyrrole}$) ppm.

$^{13}$C NMR (126 MHz, CDCl$_3$): δ=48.09 (CH$_2$), 103.50 (t, J$_{C-F}$=19.2 Hz, Ar—C$_{ipso}$), 117.12 (C=CH$_2$), 118.38 (C$_{pyrrole}$), 127.41 (C$_{pyrrole}$), 128.30 (t, J$_{C-F}$=11.3 Hz, Ar—C$_{para}$), 134.91 (CH), 137.04 (dd, J=240.2, 16.5 Hz, Ar—C$_{meta}$), 144.73 (C$_{pyrrole}$), 144.99 (d, J$_{C-F}$=245.7 Hz, Ar—C$_{ortho}$) ppm.

$^{19}$F NMR (376 MHz, CDCl$_3$): δ=−159.55 (m$_c$, J=15.0 Hz, 2F, Ar—F$_{meta}$), 141.16 (m$_c$, J=19.7, 5.1 Hz, 2F, Ar—F$_{ortho}$) ppm.

HRMS (ESI-TOF): m/z calc for C$_{18}$H$_{14}$F$_4$N$_3$$^+$ [M+H]$^+$ 348.1118, found 348.1131.

UV/VIS (DCM): λ$_{max}$/nm [log(ε/L mol$^{-1}$ cm$^{-1}$)]=431 (4.65) nm.

[4-(N-Hexylamino-2,3-5,6-tetrafluorophenyl)dipyrromethene

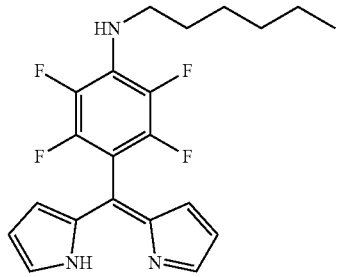 [SMILES: CCCCCCNc1c(F)c(F)c(/C(=C2\C=CC=N2)c2ccc[nH]2)c(F)c1F]

A mixture of PFP-dipyrromethane (603 mg, 1.53 mmol) and DDQ (452 mg, 1.99 mmol, 1.3 eq) in THF (10 mL) was stirred for 20 min at rt. The mixture was filtered through silica gel and evaporated to dryness. Further purification was achieved by column chromatography (silica gel, DCM) to obtain the product as yellow solid (200 mg, 34%).

Mp: 55-57° C.

$^1$H NMR (400 MHz, CDCl$_3$): δ=0.92 (t, J=7.0 Hz, 3H, CH$_3$), 1.30-1.45 (m, 6H, CH$_2$), 1.60-1.70 (m, 2H, CH$_2$), 3.44-3.51 (m, 2H, CH$_2$), 3.95 (br s, 1H, NH), 6.39 (dd, J=4.2, 1.4 Hz, 2H, H$_{pyrrole}$), 6.58 (d, J=4.2 Hz, 2H, H$_{pyrrole}$), 7.61-7.63 (m, 2H, H$_{pyrrole}$) ppm.

$^{13}$C NMR (126 MHz, CDCl$_3$): δ=14.08 (CH$_3$), 22.66 (CH$_2$), 26.42 (CH$_2$), 30.92 (CH$_2$), 31.57 (CH$_2$), 45.94 (t, J$_{C-F}$=4.0 Hz, CH$_2$), 102.79 (t, J$_{C-F}$=19.3 Hz, Ar—C$_{ipso}$), 118.40 (C$_{pyrrole}$), 127.55 (C$_{pyrrole}$), 128.94 (t, J$_{C-F}$=11.4 Hz, Ar—C$_{para}$), 136.94 (dd, J$_{C-F}$=236.3, 13.1 Hz, Ar—C$_{meta}$), 141.11 (C$_{meso}$), 144.66 (C$_{pyrrole}$), 144.93 (d, J$_{C-F}$=243.6 Hz, Ar—C$_{ortho}$) ppm.

$^{19}$F NMR (376 MHz, CDCl$_3$): δ=−160.45 (m$_c$, J=16.9 Hz, 2F, Ar—F$_{meta}$), −141.70 (m$_c$, J=15.8 Hz, 2F, Ar—F$_{ortho}$) ppm.

HRMS (ESI-TOF): m/z calc for C$_{21}$H$_{22}$F$_4$N$_3$$^+$ [M+H]$^+$ 392.1744, found 392.1739.

UV/VIS (DCM): λ$_{max}$/nm [log(ε/L mol$^{-1}$ cm$^{-1}$)]=433 (4.59) nm.

Bis[5-(4-butyloxy)-2,3,5,6-tetrafluorophenyl]dipyrrinato copper(II)

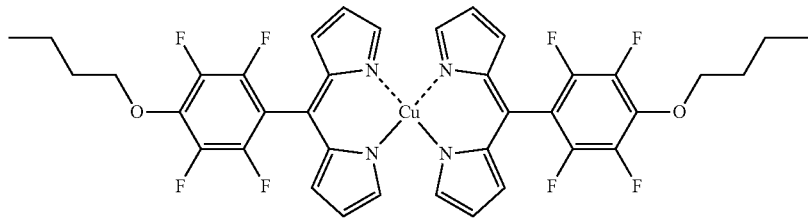

A mixture of the substituted dipyrrin (270 mg, 0.74 mmol, 2.3 eq) and CuSO$_4$.5H$_2$O (80 mg, 0.32 mmol) were dissolved in DMSO (5 mL) and stirred for 5 min at rt. The mixture was diluted with DCM and washed with water several times. The organic layer was dried with sodium sulfate, filtered and evaporated to dryness. The crude product was purified by column chromatography (silica gel, DCM/n-hexane=1:1) and washed with n-pentane to obtain the product as green crystals (219 mg, 86%).

Mp=170-175° C.

$^1$H NMR (400 MHz, (CD$_3$)$_2$CO): δ=0.95 (t, J=6.1 Hz, 6H, CH$_3$), 1.49 (brs, 4H, CH$_2$), 1.76 (brs, 4H, CH$_2$), 4.28 (brs, 4H, CH$_2$) ppm.

$^{19}$F NMR (376 MHz, CDCl$_3$): δ=−158.80--158.60 (m, 4F, Ar—F$_{meta}$), −144.00-143.3 (m, 4F, Ar—F$_{ortho}$) ppm.

HRMS (ESI-TOF): m/z calc. for C$_{19}$H$_{17}$F$_4$N$_2$O$^+$ [L+H]$^+$ 365.1272, found 365.1271; m/z calc. for C$_{38}$H$_{31}$CuF$_8$N$_4$O$_2^+$ [M+H]$^+$ 790.1610, found 790.1578; m/z calc. for C$_{38}$H$_{30}$CuF$_8$N$_4$NaO$_2^+$ [M+Na]$^+$ 812.1429, found 812.1401; m/z calc. for C$_{38}$H$_{30}$CuF$_8$KN$_4$O$_2^+$ [M+K]$^+$ 828.1169, found 828.1136.

UV/VIS (DCM): λ$_{max}$/nm [log(ε/L mol$^{-1}$ cm$^{-1}$)]=476 (4.98), 504 (4.69) nm.

Elemental analysis for C$_{38}$H$_{30}$CuF$_8$N$_4$O$_2$ (789.1): calc. 57.76 (C), 3.83 (H), 7.09 (N), found: 57.80 (C), 4.12 (H), 7.10 (N).

Bis[5-(4-prop-2-ynyloxy)-2,3,5,6-tetrafluorophenyl]dipyrrinato copper(II)

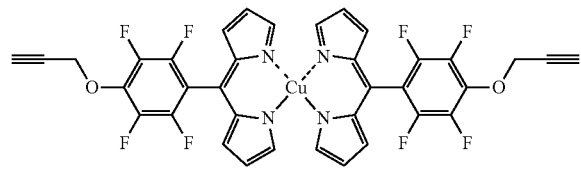

A mixture of the substituted dipyrrin (150 mg, 0.43 mmol, 2.5 eq) and CuSO$_4$.5H$_2$O (42 mg, 0.17 mmol) in DMSO (3 mL) was stirred for 5 min at rt. The mixture was diluted with DCM and washed with water several times. The organic layer was dried with sodium sulfate, filtered and evaporated to dryness. The crude product was purified by column chromatography (silica gel, DCM/n-hexane=1:1) and washed with n-pentane to obtain the product as green crystals (120 mg, 94%).

Mp: 178-180° C.

$^1$H NMR (400 MHz, (CD$_3$)$_2$CO): δ=3.20 (brs, 2H, CH), 4.95 (brs, 4H, CH$_2$) ppm.

$^{19}$F NMR (376 MHz, (CD$_3$)$_2$CO): δ=−157.3--157.0 (m, 4F, Ar—F$_{meta}$), −143.6--143.0 (m, 4F, Ar—F$_{ortho}$) ppm.

HRMS (ESI-TOF): m/z calc. for C$_{18}$H$_{11}$F$_4$N$_2$O$^+$ [L]$^+$ 347.0802, found 347.0834, m/z calc. for C$_{36}$H$_{18}$CuF$_8$N$_4$NaO$_2^+$ [M+Na]$^+$ 776.0490, found 776.0534.

UV/VIS (DCM): λ$_{max}$/nm [log(ε/L mol$^{-1}$ cm$^{-1}$)]=476 (4.80), 504 (4.50) nm.

Elemental analysis for C$_{36}$H$_{18}$CuF$_8$N$_4$O$_2$ (753.0) calc. 57.34 (C), 2.41 (H), 7.43 (H); found 57.06 (C), 2.87 (H), 7.74 (N).

Bis[5-(4-butyloxy)-2,3,5,6-tetrafluorophenyl]dipyrrinato nickel(II)

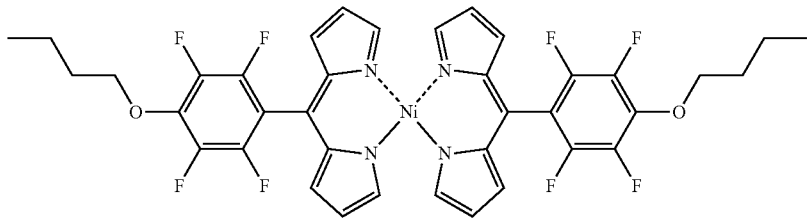

The substituted dipyrrin (55 mg, 0.15 mmol, 2.5 eq) was dissolved in DMSO (5 mL), Ni(OAc)$_2$.4H$_2$O (15 mg, 0.06 mmol) was added and the mixture stirred for 10 min. The mixture was diluted with DCM and washed with water several times. The organic layer was dried with sodium sulfate, filtered and evaporated to dryness. The crude product was purified by column chromatography (silica gel, DCM/n-hexane=1:1) to obtain the product as green solid (20 mg, 42%).

Mp: 185-187° C.

$^1$H NMR (400 MHz, (CD$_3$)$_2$CO): δ=1.03 (t, J=7.2 Hz, 6H, CH$_3$), 1.60 (d, J=6.7 Hz, 4H, CH$_2$), 1.84-1.94 (m, 4H, CH$_2$), 4.42-4.50 (m, 4H, CH$_2$) ppm.

$^{19}$F NMR (376 MHz, (CD$_3$)$_2$CO): δ=−158.9−−158.4 (m, 4F, Ar—F$_{meta}$), −143.5−−143.0 (m, 4F, Ar—F$_{ortho}$) ppm.

HRMS (ES-TOF): m/z calc. for C$_{38}$H$_{31}$F$_8$N$_4$NiO$_2$$^+$ [M+H]$^+$ 785.1667, found 785.1650.

UV/VIS (DCM): λ$_{max}$/nm [log(ε/L mol$^{-1}$ cm$^{-1}$)]=450 (4.03), 486 (4.15) nm.

Bis[5-(4-prop-2-ynyloxy)-2,3,5,6-tetrafluorophenyl]dipyrrinato nickel(II)

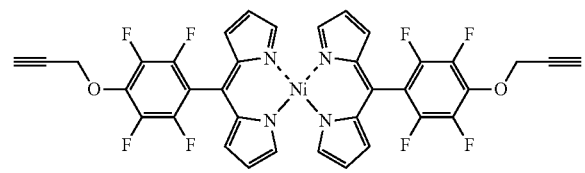

A mixture of the substituted dipyrrin (150 mg, 0.43 mmol, 2.5 eq) and Ni(OAc)$_2$.4H$_2$O (42 mg, 0.17 mmol) was dissolved in DMSO (3 mL) and the mixture stirred for 5 min at rt. The mixture was diluted with DCM and washed with water several times. The organic layer was dried with sodium sulfate, filtered and evaporated to dryness. The crude product was purified by column chromatography (silica gel, DCM/n-hexane=1:1) and the product was washed with n-pentane to obtain the product as green crystals (100 mg, 78%) mg Mp=153-155° C.

$^1$H NMR (400 MHz, (CD$_3$)$_2$CO): δ=3.38-3.40 (m, 2H, C≡CH), 5.18-5.20 (m, 4H, CH$_2$) ppm.

$^{19}$F NMR (376 MHz, (CD$_3$)$_2$CO): δ=−157.19−−157.07 (m, 4F, Ar—F$_{meta}$), −142.85−−142.65 (m, 4F, Ar—F$_{ortho}$) ppm.

HRMS (ESI-TOF): m/z calc for C$_{18}$H$_{11}$F$_4$N$_2$O$^+$ [L+H]$^+$ 347.0802, found 347.0827, m/z calc. for C$_{36}$H$_{19}$F$_8$N$_4$NiO$_2$$^+$ [M+H]$^+$ 749.0728, found 749.0767, m/z calc. for C$_{36}$H$_{18}$F$_8$N$_4$NaNiO$_2$$^+$ [M+Na]$^+$ 772.2358, found 771.0583.

UV/VIS (DCM): λ$_{max}$/nm [log(ε/L mol$^{-1}$ cm$^{-1}$)]=450 (4.60), 483 (4.71) nm.

Elemental analysis for C$_{36}$H$_{18}$F$_8$N$_4$NiO$_2$ (748.0) calc. for 57.71 (C), 2.42 (H), 7.48 (N), found 57.73 (C), 2.54 (H), 7.94 (N).

Bis[5-(4-N-prop-2-ynylamino)-2,3,5,6-tetrafluorophenyl]dipyrrinato nickel(II)

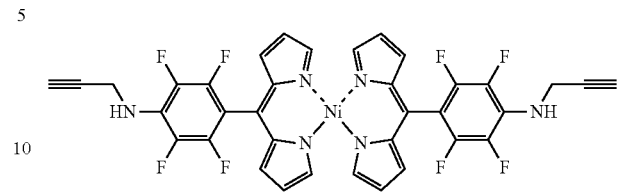

The substituted dipyrrin (55 mg, 0.15 mmol, 2.5 eq) was dissolved in DMSO (3 mL), Ni(OAc)$_2$.4H$_2$O (15 mg, 60 μmol) was added and the mixture stirred for 5 min at rt. The mixture was diluted with DCM and washed with water several times. The organic layer was dried with sodium sulfate, filtered and evaporated to dryness. The crude product was purified by column chromatography (silica gel, DCM/n-hexane=1:1) and washed with n-pentane to obtain the product as red-green crystals (25 mg, 42%).

Mp=195-200° C.

$^1$H NMR (400 MHz, (CD$_3$)$_2$CO): δ=2.85-2.89 (m, 2H, CH), 4.33 (d, J=4.3 Hz, 4H, CH$_2$) ppm.

$^{19}$F NMR (376 MHz, (CD$_3$)$_2$CO): δ=−160.36−−160.16 (m, 4F, Ar—F$_{meta}$), −144.14−−143.90 (m, 4F, Ar—F$_{ortho}$) ppm.

HRMS (ESI-TOF): m/z calc. for C$_{18}$H$_{12}$F$_4$N$_3$$^+$ [L+H]$^+$ 346.0962, found 346.0981; m/z calc. for C$_{36}$H$_{21}$F$_8$N$_6$Ni$^+$ [M+H]$^+$ 747.1048, found 747.1065.

UV/VIS (DCM): λ$_{max}$/nm [log(ε/L mol$^{-1}$ cm$^{-1}$)]=450 (5.03), 483 (5.15) nm.

Elemental analysis for C$_{36}$H$_{20}$F$_8$N$_6$Ni (746.0) calc. 57.86 (C), 2.70 (H), 11.25 (N), found 57.89 (C), 2.76 (H), 11.29 (N).

Bis[5-(4-prop-2-ynyloxy)-2,3,5,6-tetrafluorophenyl]dipyrrinato zinc(II)

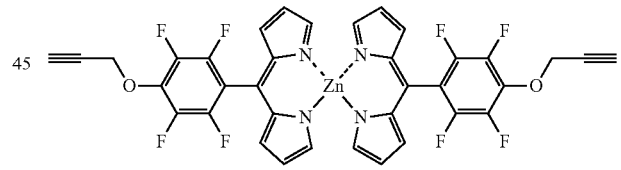

The substituted dipyrrin (100 mg, 0.28 mg) was dissolved in THF (5 mL), Zn(OAc)$_2$.2H$_2$O (161 mg, 0.28 mmol) was added and the mixture stirred for 15 min at rt. The mixture was evaporated to dryness, purified by column chromatography (silica gel, DCM/n-hexane=1:1) and washed with n-hexane to obtain the product as orange solid (51 mg, 47%).

Mp: 182-185° C.

$^1$H NMR (400 MHz, CDCl$_3$): δ=2.65 (t, J=2.3 Hz, 2H, C≡CH), 5.00 (d, J=2.1 Hz, 4H, CH$_2$), 6.45 (d, J=4.1 Hz, 4H, H$_{pyrrole}$), 6.69 (d, J=4.1 Hz, 4H, H$_{pyrrole}$), 7.55-7.58 (m, 4H, H$_{pyrrole}$) ppm.

$^{13}$C NMR (126 MHz, CDCl$_3$): δ=61.82 (CH$_2$), 76.95 (C≡CH), 77.65 (C≡CH), 118.56 (C$_{pyrrole}$), 131.39 (C$_{pyrrole}$), 139.80 (C$_{meso}$), 151.54 (C$_{pyrrole}$) ppm.

$^{19}$F NMR (376 MHz, CDCl$_3$): δ=−155.19 (m$_c$, J=22.7, 8.4 Hz, 4F, Ar—F$_{meta}$), −140.61 (m$_c$, J=23.2, 8.0 Hz, 4F, Ar—F$_{ortho}$) ppm.

HRMS (ESI-TOF): m/z calc. for $C_{18}H_{11}F_4N_2O_+$ $[L+H]^+$ 347.0802, found 347.0826; m/z calc. for $C_{36}H_{19}F_8N_4O_2Zn^+$ $[M+H]^+$ 755.0666, found 755.5752; m/z calc. for $C_{36}H_{18}F_8N_4NaO_2Zn^+$ $[M+Na]^+$ 777.0486, found 777.0499.

UV/VIS (DCM):$\lambda_{max}$/nm [log($\epsilon$/L mol$^{-1}$ cm$^{-1}$)]=475 (4.88), 495 (5.07) nm.

Fluorescence: $\lambda_{max}$: 526 nm at $\lambda_{Excitation}$: 450 nm.

Example 2

Preparation of Tris(dipyrrinato) Metal Complexes a) In(III) Complexes

Tris(5-pentafluorophenyl)dipyrrinato indium (III)

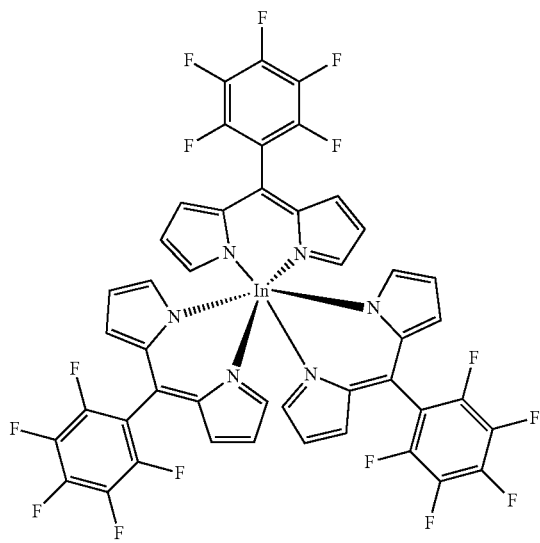

Under argon atmosphere 5-(pentafluorophenyl)dipyrrin (100 mg, 0.32 mmol, 3.1 eq) was dissolved in dry THF (10 mL), InCl$_3$ (23 mg, 0.10 mmol) and DIPEA (186 mg, 1.44 mmol, 14 eq) were added and the mixture was refluxed for 6 hours. The solvent was evaporated to dryness and the crude product was purified by column chromatography (silica gel, DCM) to obtain the product as orange crystals (146 mg, 44%).

Mp: >300° C.

$^1$H (400 MHz, CDCl$_3$): δ=6.39 (dd, J=4.2, 1.3 Hz, 6H, H$_{pyrrole}$), 6.61 (d, J=4.1 Hz, 6H, H$_{pyrrole}$), 7.18-7.20 (m, 6H, H$_{pyrrole}$) ppm.

$^{13}$C NMR (126 MHz, CDCl$_3$): δ=113.63 (t, $J_{C-F}$=18.0 Hz, Ar—C$_{ipso}$), 118.63 (C$_{pyrrole}$), 132.43 (C$_{pyrrole}$), 136.24 (t, $J_{C-F}$=14.0 Hz, Ar—C$_{para}$) 138.26 (t, $J_{C-F}$=13.5 Hz, Ar—C$_{para}$), 139.74 (C$_{meso}$), 141.57 (d, $J_{C-F}$=259.5 Hz, Ar—C$_{meta}$), 144.72 (d, $J_{C-F}$=250.3 Hz, Ar—C$_{ortho}$), 151.52 (C$_{pyrrole}$) ppm.

$^{19}$F NMR (376 MHz, CDCl$_3$): δ=−161.22--161.06 (m, 6F, Ar—F$_{meta}$), −152.66 (t, J=20.8 Hz, 3F, Ar—F$_{para}$), −139.06 (m$_c$, J=23.5, 6.7 Hz, 6F, Ar—F$_{ortho}$) ppm.

HRMS (ESI-TOF): m/z calc for $C_{30}H_{12}F_{10}InN_4^+$ [M−L]$^+$ 732.9941, found 732.9961; m/z calc. for $C_{45}H_{18}F_{15}InKN_6^+$ [M+K]$^+$ 1081.0024, found 1081.0078.

UV/VIS (DCM): $\lambda_{max}$/nm [log($\epsilon$/L mol$^{-1}$ cm$^{-1}$)]=455 (5.17), 508 (4.94) nm.

Tris(5-pentafluorophenyl)dipyrrinato indium(III)

A mixture of the substituted dipyrrin (50 mg, 0.14 mmol, 3.1 eq), InCl$_3$ (10 mg, 0.04 mmol) and DIPEA (23 µmol, 0.14 mmol, 3.1 eq) was dissolved in THF (10 mL) and refluxed for 4 hours. The mixture was diluted with DCM and washed several times with water. The organic layer was dried with sodium sulfate, filtered and evaporated to dryness. The crude product was purified by column chromatography (silica gel, DCM/n-hexane=3:1), washed with pentane to obtain the product as orange crystals (30 mg, 56%).

Mp: 222-230° C.

$^1$H NMR (400 MHz, CDCl$_3$): δ=4.82 (d, J=6.2 Hz, 6H, CH$_2$), 5.36 (dd, J=10.3, 0.8 Hz, 6H, C═CH$_2$), 5.45 (dd, J=17.1, 1.4 Hz, 6H, C═CH$_2$), 6.02-6.14 (m, 3H, CH), 6.37 (dd, J=4.2, 1.2 Hz, 6H, H$_{pyrrole}$), 6.62 (d, J=4.0 Hz, 6H, H$_{pyrrole}$), 7.18-7.20 (m, 6H, H$_{pyrrole}$) ppm.

$^{13}$C NMR (126 MHz, CDCl$_3$): δ=75.53 (CH$_2$), 112.25 (t, $J_{C-F}$=19.5 Hz, Ar—F$_{ipso}$), 118.29 (C$_{pyrrole}$), 120.35 (C═CH$_2$), 132.23 (CH), 132.51 (C$_{pyrrole}$), 140.01 (C$_{meso}$), 151.23 (C$_{pyrrole}$), 137.21 (t, $J_{C-F}$=12.1 Hz, Ar—F$_{para}$), 140.69 (d, $J_{C-F}$=239.6 Hz, Ar—C$_{meta}$), 144.80 (d, $J_{C-F}$=243.0 Hz, Ar—F$_{ortho}$) ppm.

$^{19}$F NMR (376 MHz, CDCl$_3$): δ=−156.09 (m$_c$, J=22.3, 7.4 Hz, 2F, Ar—F$_{meta}$), −141.02 (m$_c$, J=21.4, 7.2 Hz, 2F, Ar—F$_{ortho}$) ppm.

HRMS (ESI-TOF): m/z calc for $C_{54}H_{33}F_{12}InN_6NaO_3^+$ [M+Na]$^+$ 1179.1354, found 1179.1337; m/z calc for $C_{36}H_{22}F_8InN_4O_2^+$ [M−L]$^+$ 809.0654, found 809.0633.

UV/VIS (DCM): $\lambda_{max}$/nm [log($\epsilon$/L mol$^{-1}$ cm$^{-1}$)]=455 (4.71), 507 (4.45) nm.

19
Tris[5-(4-butyloxy)-2,3,5,6-tetrafluorophenyl]dipyrrinato indium(III)

20
Tris[5-(4-N-prop-ynylamino)-2,3,5,6-tetrafluorophenyldipyrrinato indium(III)

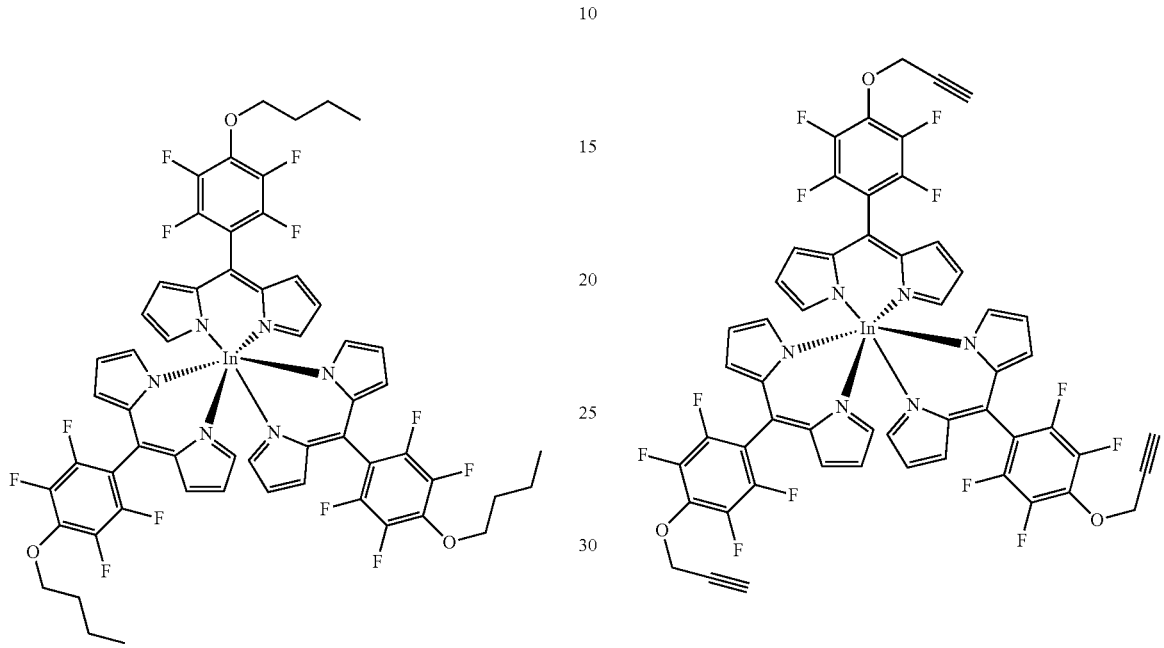

Under argon atmosphere a mixture of the substituted dipyrrin (116 mg, 0.31 mmol, 3.1 eq), InCl$_3$ (22 mg, 0.10 mmol) and DIPEA (41 mg, 50 µL, 0.31 mmol, 3.1 eq) in dry THF (5 mL) was refluxed for 12 hours. The mixture was diluted with DCM and washed several times with water. The organic layer was dried with sodium sulfate, filtered and evaporated to dryness. The crude product was purified by column chromatography (silica gel, DCM/n-hexane=1:1) to obtain the product as orange solid (8 mg, 6%).

Mp: 105-110° C.

$^1$H (700 MHz, CDCl$_3$): δ=1.01 (t, J=7.4 Hz, 9H, CH$_3$), 1.50-1.60 (m, 6H, CH$_2$), 1.79-1.84 (m, 6H, CH$_2$), 4.33 (t, J=6.6 Hz, 6H, CH$_2$), 6.38 (dd, J=4.2, 1.4 Hz, 6H, H$_{pyrrole}$), 6.65 (d, J=4.2 Hz, 6H, H$_{pyrrole}$), 7.00-7.20 (m, 6H, H$_{pyrrole}$) ppm.

$^{13}$C NMR (176 MHz, CDCl$_3$): The signal to noise ratio does not allow a meaningful interpretation.

$^{19}$F NMR (376 MHz, CDCl$_3$): δ=−156.97 (m$_c$, J=22.3, 7.9 Hz, 6F, Ar—F$_{meta}$), −141.16 (m$_c$, J=22.4, 8.1 Hz, 6F, Ar—F$_{ortho}$) ppm.

HRMS (ESI-TOF): m/z calc. for C$_{57}$H$_{45}$F$_{12}$InN$_6$NaO$_3$$^+$ [M+Na]$^+$ 1227.2293, found 1227.2282; m/z calc for C$_{38}$H$_{30}$F$_8$InN$_4$O$_2$$^+$ [M−L]$^+$ calc. for 841.1280, found 841.1274.

UV/VIS (DCM): λ$_{max}$/nm [log(ε/L mol$^{-1}$ cm$^{-1}$)]=449 (4.67), 506 (4.51) nm.

Under argon atmosphere a mixture of the substituted dipyrrin (100 mg, 0.288 mmol, 3.1 eq), InCl$_3$ (32 mg, 90 µmol) and DIPEA (40 µL, 37 mg, 0.288 mmol, 3.1 eq) in dry THF (10 mL) was refluxed for 12 h. The mixture was diluted with DCM, washed with water several times, dried with sodium sulfate, filtered and evaporated to dryness. The crude product was purified by column chromatography (silica gel, DCM/n-hexane=1:1) to obtain the product as yellow solid (86 mg, 83%).

Mp: 70-75° C.

$^1$H NMR (400 MHz, CDCl$_3$): δ=2.64 (t, J=2.4 Hz, 3H, CH), 4.98 (d, J=2.4 Hz, 6H, CH$_2$), 6.41 (dd, J=4.2, 1.5 Hz, 6H, H$_{pyrrole}$), 6.51 (d, J=4.2 Hz, 6H, H$_{pyrrole}$), 7.64-7.66 (m, 6H, H$_{pyrrole}$) ppm.

$^{13}$C NMR (126 MHz, CDCl$_3$): δ=61.82 (CH$_2$), 76.93 (C≡CH), 77.64 (C≡CH), 111.17 (t, J$_{C-F}$=19.2 Hz, Ar—C$_{ipso}$), 118.87 (C$_{pyrrole}$), 124.91 (C$_{meso}$), 127.18 (C$_{pyrrole}$), 136.21 (t, J$_{C-F}$=12.3 Hz, Ar—C$_{para}$), 140.64 (C$_{meso}$), 141.26 (m, Ar—C$_{meta}$), 144.95 (m, Ar—C$_{ortho}$), 145.24 (C$_{pyrrole}$) ppm.

$^{19}$F NMR (376 MHz, CDCl$_3$): δ=−155.08−−154.96 (m, 6F, Ar—F$_{metal}$), −139.95−−139.83 (m, 6F, Ar—F$_{ortho}$) ppm.

HRMS (ESI-TOF): m/z calc. for C$_{54}$H$_{27}$F$_{12}$InKN$_6$O$_3$$^+$ [M+K]$^+$ 1189.0623, found 1189.0607.

UV/VIS (DCM): λ$_{max}$/nm [log(ε/L mol$^{-1}$ cm$^{-1}$)]=432 (4.98) nm.

21
Tris[5-(4-N-prop-2-ynylamino)-2,3,5,6-tetrafluorophenyl)dipyrrinato indium(III)

22
Tris[5-(4-N-prop-2-enylamino)-2,3,5,6-tetrafluorophenyl]dipyrrinato indium(III)

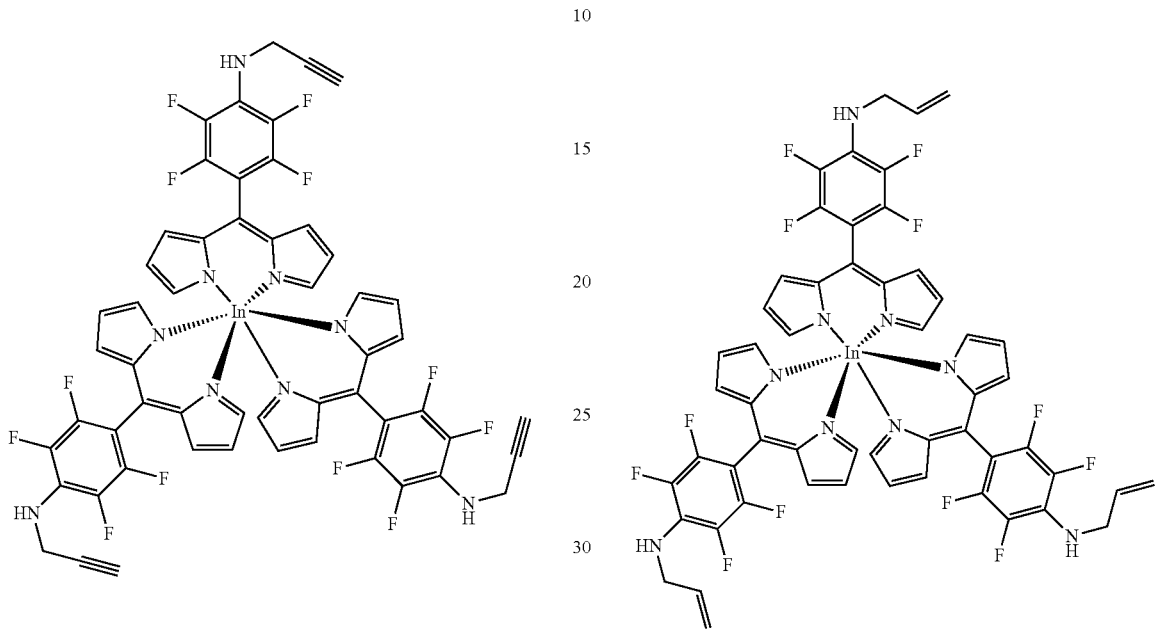

Under argon atmosphere the substituted dipyrrin (120 mg, 0.34 mmol, 3.1 eq), InCl$_3$ (25 mg, 0.11 mmol) and DIPEA (60 µL, 44 mg, 0.34 mmol, 3.1 eq) were dissolved in dry THF and refluxed for 24 hours. The mixture was diluted with DCM and washed with water several times. The organic layer was dried with sodium sulfate, filtered and evaporated to dryness. The crude product was purified by column chromatography (silica gel, DCM/n-hexane=1:1) to obtain the product as red oil (100 mg, 79%).

$^1$H NMR (400 MHz, CDCl$_3$): δ=2.34-2.36 (m, 3H, C≡CH), 4.20-4.25 (m, 6H, CH$_2$), 6.41 (dd, J=4.2, 1.4 Hz, 6H, H$_{pyrrole}$), 6.57 (d, J=4.2 Hz, 6H, H$_{pyrrole}$) 7.63-7.65 (m, 6H, H$_{pyrrole}$) ppm.

$^{13}$C NMR (126 MHz, CDCl$_3$): δ=35.47 (CH$_2$), 80.08 (C≡CH), 72.86 (C≡CH), 105.33 (t, J$_{C-F}$=19.1 Hz, Ar—C$_{ipso}$), 118.59 (C$_{pyrrole}$), 125.88 (t, J$_{C-F}$=2.0 Hz, Ar—C$_{para}$), 127.43 (C$_{pyrrole}$), 137.87 (d, J$_{C-F}$=241.2 Hz, Ar—C$_{meta}$), 141.06 (C$_{meso}$), 144.90 (C$_{pyrrole}$), 145.05 (d, J$_{C-F}$=246.4 Hz, Ar—C$_{ortho}$) ppm.

$^{19}$F NMR (376 MHz, CDCl$_3$): δ=−158.33 (m$_c$, J=21.3, 7.4 Hz, 6F, Ar—F$_{meta}$), −140.95 (m$_c$, J=13.5, 9.8 Hz, 6F, Ar—F$_{ortho}$) ppm.

HRMS (ESI-TOF): m/z calc. for C$_{54}$H$_{30}$F$_{12}$InN$_9$Na$^+$ [M+Na]$^+$ 1170.1364, found 1170.1367; m/z calc. for C$_{54}$H$_{30}$F$_{12}$InKN$_9^+$ [M+K]$^+$ 1186.1103, found 1186.1107.

UV/VIS (DCM): λ$_{max}$/nm [log(ε/L mol$^{-1}$ cm$^{-1}$)]=438 (5.06) nm.

Under argon atmosphere a mixture of the substituted dipyrrin (150 mg, 0.43 mmol, 3.1 eq), InCl$_3$ (31 mg, 0.14 mmol) and DIPEA (73 µL, 0.43 mmol, 3.1 eq) was dissolved in dry THF (10 mL) and refluxed for 24 h. The mixture was diluted with DCM and washed with water several times. The organic layer was dried with sodium sulfate, filtered and evaporated to dryness. The crude product was purified by column chromatography (silica gel, DCM/n-hexane=1:1) to obtain the product as yellow oil (63 mg, 42%).

$^1$H (400 MHz, CDCl$_3$): δ=4.05-4.15 (m, 6H, CH$_2$), 5.24 (dd, J=10.3, 0.6 Hz, 3H, C=CH$_2$), 5.32 (dd, J=17.2, 1.1 Hz, 3H, C=CH$_2$), 5.93-6.04 (m, 3H, CH), 6.40 (dd, J=4.2, 1.4 Hz, 6H, H$_{pyrrole}$), 6.58 (d, J=4.2 Hz, 6H, H$_{pyrrole}$), 7.61-7.64 (m, 6H, H$_{pyrrole}$) ppm.

$^{13}$C NMR (126 MHz, CDCl$_3$): δ=48.13 (t, J$_{C-F}$=4.5 Hz, CH$_2$), 103.58 (t, J$_{C-F}$=19.2 Hz, Ar—C$_{ipso}$), 117.20 (C=CH$_2$), 118.47 (C$_{pyrrole}$), 126.25 (t, J$_{C-F}$=2.1 Hz, Ar—C$_{para}$) 127.51 (C$_{pyrrole}$), 135.00 (CH), 137.23 (d, J$_{C-F}$=240.0 Hz, Ar—C$_{meta}$), 141.10 (C$_{meso}$), 144.75 (C$_{pyrrole}$), 145.02 (d, J$_{C-F}$=245.0 Hz, Ar—C$_{ortho}$).

$^{19}$F NMR (376 MHz, CDCl$_3$): δ=−159.55 (m$_c$, J=14.4 Hz, 6F, Ar—F$_{meta}$), −141.46 (m$_c$, J=20.1, 5.7 Hz, 6F, Ar—F$_{ortho}$) ppm.

HRMS (ESI-TOF): m/z calc. for C$_{54}$H$_{36}$F$_{12}$InN$_9$Na$^+$ [M+Na]$^+$ 1176.1833, found 1176.1857; m/z calc. for C$_{54}$H$_{36}$F$_{12}$InKN$_9^+$ [M+K]$^+$ 1192.1572, found 1192.1594.

UV/VIS (DCM): λ$_{max}$/nm [log(ε/L mol$^{-1}$ cm$^{-1}$)]=437 (4.92) nm.

b) Ga(III) Complexes

Tris(5-pentafluorophenyldipyrrinato) gallium(III)

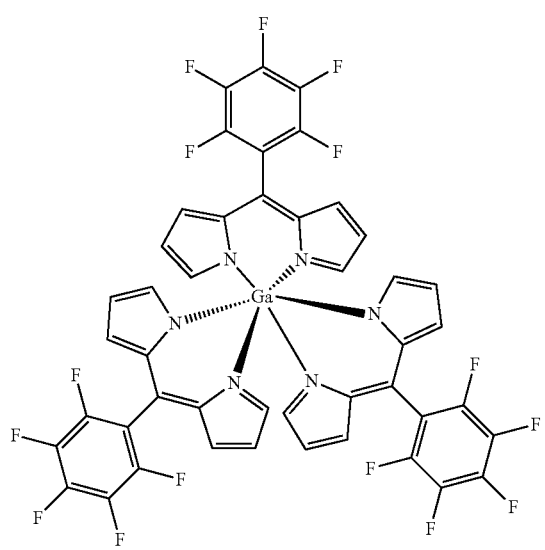

Under argon atmosphere 5-(pentafluorophenyl)dipyrrin (486 mg, 1.56 mmol, 3.1 eq) was dissolved in dry THF (10 mL), GaCl$_3$ (89 mg, 0.50 mmol) and DIPEA (2.3 mL, 7.00 mmol, 14 eq) were added and the mixture was refluxed for 6 h. The solvent was evaporated to dryness and the crude product was purified by column chromatography (silica gel, DCM) to obtain the product as orange crystals (311 mg, 48%).

Mp: 236-240° C.

$^1$H NMR (400 MHz, CDCl$_3$): δ=6.33 (dd, J=4.2, 1.4 Hz, 6H, H$_{pyrrole}$), 6.58 (d, J=4.1 Hz, 6H, H$_{pyrrole}$), 6.96-6.98 (m, 6H, H$_{pyrrole}$) ppm.

$^{13}$C NMR (126 MHz, CDCl$_3$): δ=112.93 (t, J$_{C-F}$=19.5 Hz, Ar—C$_{ipso}$), 118.10. (C$_{pyrrole}$), 131.23 (C$_{pyrrole}$), 136.31 (t, J$_{C-F}$=12.9 Hz, Ar—C$_{para}$) 138.33 (C$_{meso}$), 141.53 (d, J$_{C-F}$=255.5 Hz, Ar—C$_{meta}$), 144.68 (d, J$_{C-F}$=246.5 Hz, Ar—C$_{ortho}$), 150.40 (C$_{pyrrole}$) ppm.

$^{19}$F NMR (376 MHz, CDCl$_3$): δ=−161.15-−161.00 (m, 6F, Ar—F$_{meta}$), −152.50 (t, J=20.8 Hz, 3F, Ar—F$_{para}$), −139.05-−138.90 (m, J=15.3 Hz, 6F, Ar—F$_{ortho}$) ppm.

HRMS (ESI-TOF): m/z calc. C$_{45}$H$_{18}$F$_{15}$GaKN$_6^+$ [M+K]$^+$: 1035.0241, found 1035.0245; m/z calc. for C$_{30}$H$_{12}$F$_{10}$GaN$_4^+$ [M−L]$^+$ 687.0158, found 687.0165.

UV/VIS (DCM): λ$_{max}$/nm [log(ε/L mol$^{-1}$ cm$^{-1}$)]=457 (4.92), 509 (4.83) nm.

Elemental analysis C$_{45}$H$_{18}$F15GaN$_6$ (996.0): calc. 54.19 (C), 1.82 (H), 8.43 (N), found 54.23 (C), 2.05 (H), 8.72 (N).

Tris[5-(4-butyloxy)2,3,5,6-tetrafluorophenyl)dipyrrinato gallium(III)

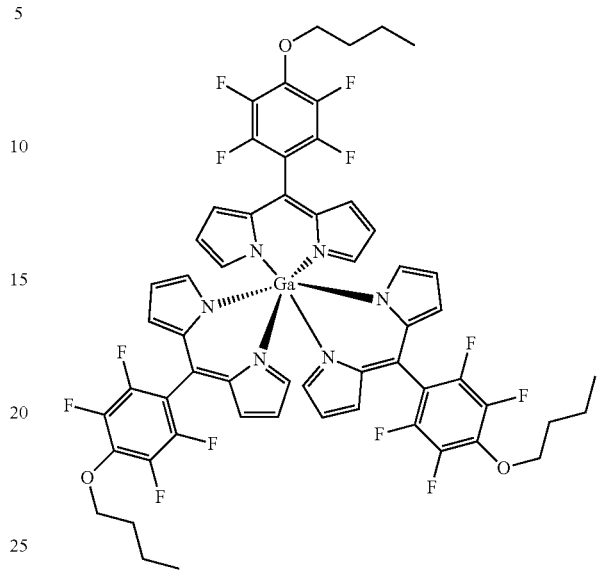

Method A: Under argon atmosphere and the exclusion of light a mixture of tris[5-(pentafluorophenyl)dipyrrinato]gallium(III) (50 mg, 50 μmol), freshly powdered KOH (42 mg, 0.75 mmol, 15 eq) and butanol (90 μL, 74 mg, 1.00 mmol, 20 eq) in dry THF (3 mL) were stirred for 16 hours at rt. The mixture was diluted with DCM and washed several times with water. The organic layer was dried with sodium sulfate, filtered and evaporated to dryness. The crude product was purified by column chromatography (silica gel, DCM/n-hexane=1:2) to obtain the product as orange solid (29 mg, 50%).

Method B: Under argon atmosphere the substituted dipyrrin (130 mg, 0.357 mmol, 3.1 eq) was dissolved in dry THF (10 mL), GaCl$_3$ (20 mg, 0.11 mmol) and DIPEA (40 μL, 46 mg, 0.35 mmol, 3.1 eq) were added and the mixture was refluxed for 12 hours. The mixture was diluted with DCM and washed with water several times. The organic layer was dried with sodium sulfate, filtered and evaporated to dryness. The crude product was purified by column chromatography (silica gel, DCM/n-hexane=1:1) to obtain the product as orange solid (38 mg, 30%).

Mp: 208-218° C.

$^1$H NMR (400 MHz, CDCl$_3$): δ=1.00 (t, J=7.4 Hz, 9H, CH$_3$), 1.50-1.58 (m, 6H, CH$_2$), 1.78-1.86 (m, 6H, CH$_2$), 4.33 (t, J=6.4 Hz, 6H, CH$_2$), 6.30 (dd, J=4.2, 1.5 Hz, 6H, H$_{pyrrole}$), 6.62 (d, J=4.0 Hz, 6H, H$_{pyrrole}$), 6.96-6.98 (m, 6H, H$_{pyrrole}$) ppm.

$^{13}$C NMR (126 MHz, CDCl$_3$): δ=13.84 (CH$_3$), 18.91 (CH$_2$), 32.07 (CH$_2$), 75.26 (CH$_2$), 111.05 (t, J$_{C-F}$=19.6 Hz, Ar—C$_{ipso}$), 117.91 (C$_{pyrrole}$), 131.34 (C$_{pyrrole}$), 138.32 (t, J$_{C-F}$=13.5 Hz, Ar—C$_{para}$) 138.74 (C$_{meso}$), 140.79 (dd, J$_{C-F}$=249.2, 14.7 Hz, Ar—C$_{meta}$), 144.81 (d, J$_{C-F}$=235.3 Hz, Ar—C$_{ortho}$), 150.24 (C$_{pyrrole}$) ppm.

$^{19}$F NMR (376 MHz, CDCl$_3$): δ=−156.93 (m$_c$, J=21.4, 7.3 Hz, 6F, Ar—C$_{meta}$), −141.05 (m$_c$, J=21.7, 7.3 Hz, 6F, Ar—F$_{ortho}$) ppm.

HRMS (ESI-TOF): m/z calc. for C$_{38}$H$_{30}$F$_8$GaN$_4$O$_2^+$ [M−L]$^+$ 795.1497, found 795.1492; m/z calc. for C$_{57}$H$_{45}$F$_{12}$GaN$_6$NaO$_3^+$ [M+Na]$^+$ 1181.2510, found 1181.2491.

UV/VIS (DCM): $\lambda_{max}$/nm [log($\epsilon$/L mol$^{-1}$ cm$^{-1}$)]=457 (4.95), 508 (4.86) nm Tris[(4-prop-2-enyloxy)-2,3,5,6-tetrafluorophenyl] dipyrrinato gallium(III)

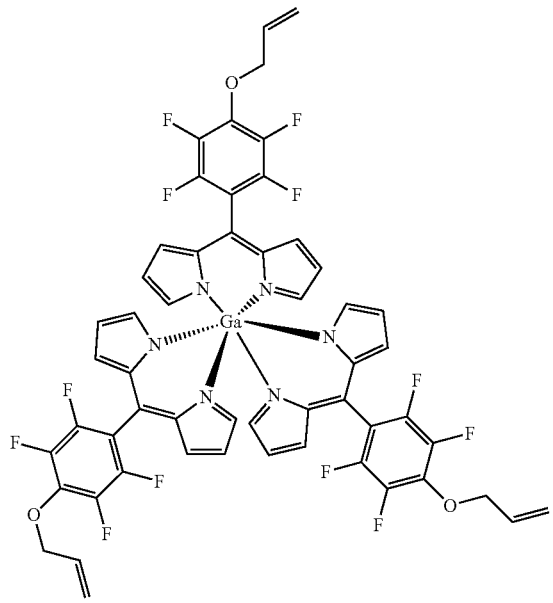

Method A: Under argon atmosphere a mixture of tris[5-(pentafluorophenyl)dipyrrinato]gallium(III) (50 mg, 50 µmol), freshly powdered KOH (26 mg, 1.5 mmol, 30 eq) and allylic alcohol (68µ, 58 mg, 1 mmol, 20 eq) in dry THF (3 mL) were stirred at rt for 16 hours. The mixture was diluted with DCM, washed several times with water and the organic layer was dried with sodium sulfate, filtered and evaporated to dryness. The crude product was purified by column chromatography (silica gel, DCM/n-hexane=1:1) to obtain the product as orange solid (14 mg, 25%).

Method B: Under argon atmosphere the substituted dipyrrin (100 mg, 0.287 mmol, 3.1 eq) was dissolved in dry THF (10 mL), GaCl$_3$ (16 mg, 0.09 mmol) and DIPEA (40 µL, 37 mg, 0.287 mmol, 3.1 eq) were added and the mixture was refluxed for 4 h. The mixture was diluted with DCM and washed with water several times, dried with sodium sulfate, filtered and evaporated to dryness. The crude product was purified by column chromatography (silica gel, DCM/n-hexane=3:1), washed with pentane and the product was obtained as orange crystals (58 mg, 57%).

Mp: 209-216° C.

$^1$H NMR (400 MHz, CDCl$_3$): δ=4.82 (d, J=6.0 Hz, 6H, CH$_2$), 5.36 (dd, J=10.3, 1.1 Hz, 3H, C=CH$_2$), 5.45 (dd, J=17.1, 1.4 Hz, 3H, C=CH$_2$), 6.10-6.15 (m, 3H, CH), 6.30 (dd, J=4.2, 1.4 Hz, 6H, H$_{pyrrole}$), 6.60 (d, J=4.0 Hz, 6H, H$_{pyrrole}$), 6.95-6.98 (m, 6H, H$_{pyrrole}$) ppm.

$^{13}$C NMR (126 MHz, CDCl$_3$): δ=75.53 (CH$_2$), 111.55 (t, $J_{C-F}$=19.5 Hz, Ar—C$_{ipso}$), 117.88 (C$_{pyrrole}$), 120.34 (C=CH$_2$), 131.29 (C$_{pyrrole}$), 132.23 (CH), 138.58 (C$_{meso}$), 137.27 (t, $J_{C-F}$=11.9 Hz, Ar—C$_{para}$) 140.91 (dd, $J_{C-F}$=249.1, 14.8 Hz, Ar—C$_{meta}$), 144.81 (d, $J_{C-F}$=247.6 Hz, Ar—C$_{ortho}$), 150.26 (C$_{pyrrole}$) ppm.

$^{19}$F NMR (376 MHz, CDCl$_3$): δ=−156.04 (m$_c$, J=22.4, 7.7 Hz, 6F, Ar—F$_{meta}$), −140.90 (m$_c$, J=23.1, 7.3 Hz, 6F, Ar—F$_{ortho}$) ppm.

HRMS (ESI-TOF): m/z calc for C$_{54}$H$_{33}$F$_{12}$GaN$_6$NaO$_3$+ [M+Na]$^+$ 1133.1571, found 1133.1576; m/calc for C$_{36}$H$_{22}$F$_8$GaN$_4$O$_2$ [M−L]$^+$ 763.0871, found 763.0891.

UV/Vis (DCM): $\lambda_{max}$/nm [log($\epsilon$/L mol$^{-1}$ cm$^{-1}$)]=456 (4.94), 508 (4.89) nm.

Tris-[5-(4-prop-2-ynyloxy)-2,3,5,6-tetrafluorophenyl]dipyrrinato gallium(III)

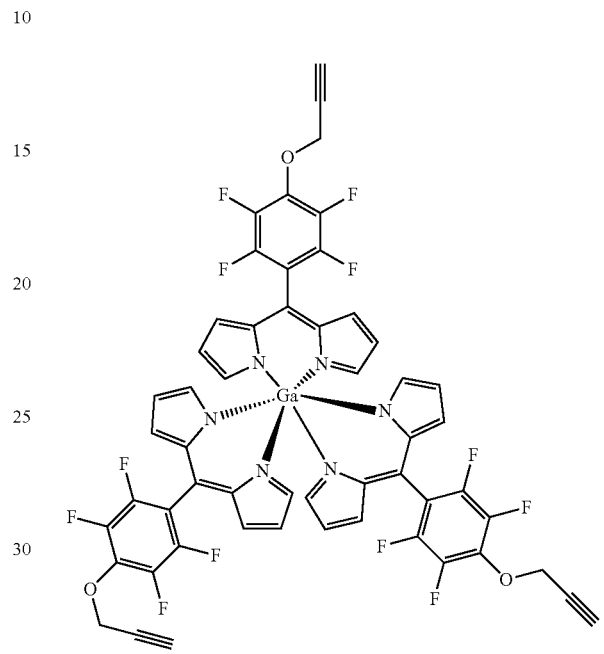

Method A: Under argon atmosphere a mixture of tris[5-(pentafluorophenyl)dipyrrinato]gallium(III) (50 mg, 50 µmol), propargylic alcohol (0.10 mL, 105 mg, 210 µmol, 4.2 eq) and freshly powdered KOH (10 mg, 170 µmol, 3.5 eq) in dry THF (10 mL) was stirred under the exclusion of light for 16 h at rt. TLC shows three products, so that more KOH (10 mg, 170 µmol, 3.5 eq) and alcohol (0.10 mL, 105 mg, 210 µmol, 4.2 eq) were added and the mixture stirred for another 24 h. The mixture was diluted with DCM, washed with water several times, dried with sodium sulfate, filtered and evaporated to dryness. The crude product was purified by column chromatography (silica gel, DCM/n-hexane=1:1) and washed with n-pentane. The product was isolated as orange crystals in 54% (30 mg) yield.

Method B: Under argon atmosphere a mixture of the substituted dipyrrin (100 mg, 0.28 mmol, 3.1 eq), GaCl$_3$ (16 mg, 90 µmol) and DIPEA (37 mg, 40 µL, 288 µmol, 14 eq) was dissolved in dry THF and refluxed for 12 h. The mixture was diluted with DCM and washed with water several times. The organic layer was dried with sodium sulfate, filtered and evaporated to dryness. The crude product was purified by column chromatography (silica gel, DCM/n-hexane=1:1) to obtain the product as orange crystals (23 mg, 23%).

Mp: >300° C.

$^1$H NMR (400 MHz, CDCl$_3$): δ=2.90 (t, J=2.4 Hz, 3H, CH), 5.25 (d, J=2.4 Hz, 6H, CH$_2$), 6.59 (dd, J=4.1, 1.3 Hz, 6H, H$_{pyrrole}$), 6.89 (d, J=4.2 Hz, 6H, H$_{pyrrole}$), 7.53-7.54 (m, 6H, H$_{pyrrole}$) ppm.

$^{13}$C NMR (126 MHz, CDCl$_3$): δ=61.72 (CH$_2$), 76.91 (C≡CH), 77.63 (C≡CH), 112.59 (t, $J_{C-F}$=19.5 Hz, Ar—C$_{ipso}$), 118.12 (C$_{pyrrole}$), 131.30 (C$_{pyrrole}$), 136.07 (m, Ar—C$_{para}$) 138.47 (C$_{meso}$), 141.22 (d, $J_{C-F}$=259.7 Hz, Ar—

$C_{meta}$), 144.65 (d, $J_{C-F}$=240.2 Hz, Ar—$C_{ortho}$), 150.35 ($C_{pyrrole}$) ppm. $^{19}$F NMR (376 MHz, CDCl$_3$): δ=−155.24 ($m_c$, J=21.5, 7.2 Hz, 6F, Ar—$F_{meta}$), −140.50 ($m_c$, J=21.8, 7.3 Hz, 6F, Ar—$F_{ortho}$) ppm.

HRMS (ESI-TOF): m/z calc. for $C_{36}H_{18}F_8GaN_4O_2^+$ [M−L]$^+$ 759.0558, found 759.0551; m/z calc. for $C_{54}H_{27}F_{12}GaKN_6O_3^+$ [M+K]$^+$ 1143.0840, found 1143.0817.

UV/VIS (DCM): $\lambda_{max}$/nm [log(ε/L mol$^{-1}$ cm$^{-1}$)]=457 (5.09), 508 (5.05) nm.

Tris[5-(4-N-hexylamino]-2,3,5,6-tetrafluorophenyl)] dipyrrin gallium(III)

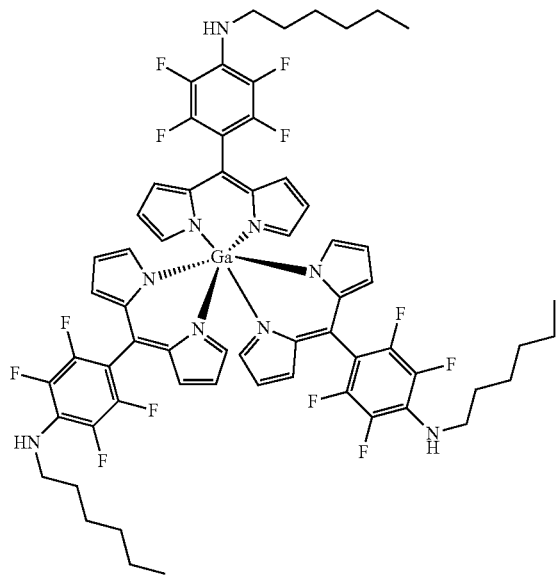

Under argon atmosphere a mixture of the substituted dipyrrin (100 mg, 0.25 mmol, 3.1 eq), GaCl$_3$ (14 mg, 80 μmol) and DIPEA (22 mg, 0.25 mmol, 3.1 eq) was dissolved in dry THF and the mixture was refluxed for 16 h. The mixture was diluted with DCM and washed with water several times. The organic layer was dried with sodium sulfate, filtered and evaporated to dryness. The crude product was purified by column chromatography (silica gel, DCM/n-hexane=1:1) to obtain the product as orange solid (121 mg, 97%).

Mp: 55-60° C.

$^1$H NMR (400 MHz, CDCl$_3$): δ=0.92 (t, J=7.0 Hz, 9H, CH$_3$), 1.30-1.45 (m, 18H, CH$_2$), 1.60-1.70 (m, 6H, CH$_2$), 3.43-3.51 (m, 6H, CH$_2$), 6.39 (dd, J=4.2, 1.4 Hz, 6H, H$_{pyrrole}$), 6.59 (d, J=4.2, 0.8 Hz, 6H, H$_{pyrrole}$), 7.61-7.62 (m, 6H, H$_{pyrrole}$) ppm.

$^{13}$C NMR (126 MHz, CDCl$_3$): δ=14.09 (CH$_3$), 22.68 (CH$_2$), 26.43 (CH$_2$), 30.82 (CH$_2$), 31.50 (CH$_2$), 45.99 (CH$_2$), 102.82 (t, $J_{C-F}$=19.2 Hz, Ar—$C_{ipso}$), 118.42 ($C_{pyrrole}$), 127.50 ($C_{pyrrole}$), 128.96 (t, $J_{C-F}$=11.3 Hz, Ar—$C_{para}$) 136.98 (dd, $J_{C-F}$=239.3, 16.4 Hz, Ar—$C_{meta}$), 141.20 ($C_{meso}$), 145.02 (d, $J_{C-F}$=245.7 Hz, Ar—$C_{ortho}$), 144.67 ($C_{pyrrole}$) ppm.

$^{19}$F NMR (376 MHz, CDCl$_3$): δ=−160.45 ($m_c$, J=16.8 Hz, Ar—$C_{meta}$), −141.70 ($m_c$, J=14.9 Hz, Ar—$C_{ortho}$) ppm.

UV/VIS (DCM): $\lambda_{max}$/nm [log(ε/L mol$^{-1}$ cm$^{-1}$)]=433 (4.96) nm.

Tris[5-(4-N-prop-2-ynylamino)-2,3,5,6-tetrafluorophenyl)dipyrrinato gallium(III)

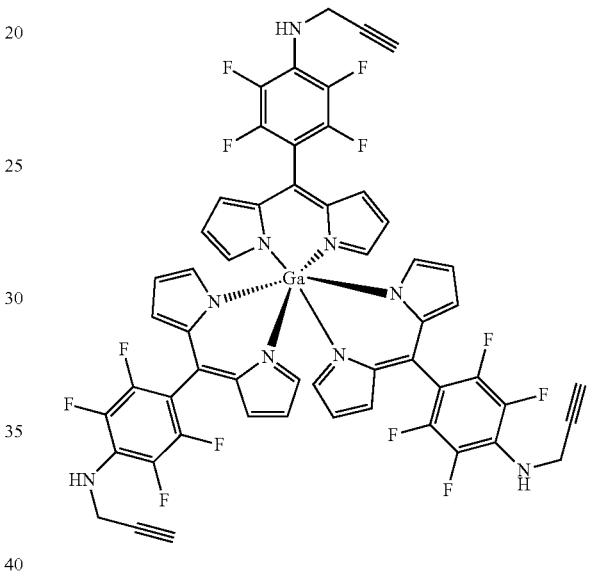

Under argon atmosphere the substituted dipyrrin (125 mg, 0.36 mmol, 3.1 eq), GaCl$_3$ (20 mg, 0.11 mmol) and DIPEA (60 μL, 0.36 mmol, 3.1 eq) were dissolved in dry THF and refluxed for 24 h. The mixture was diluted with DCM and washed with water several times. The organic layer was dried with sodium sulfate, filtered and evaporated to dryness. The crude product was purified by column chromatography (silica gel, DCM/n-hexane=1:1) to obtain the product as red oil (96 mg, 75%).

$^1$H NMR (400 MHz, CDCl$_3$): δ=2.35 (t, J=2.3 Hz, 3H, C≡CH), 4.20-4.24 (m, 6H, CH$_2$), 6.41 (dd, J=4.2, 1.4 Hz, 6H, H$_{pyrrole}$), 6.58 (d, J=4.1 Hz, 6H, H$_{pyrrole}$), 7.62-7.64 (m, 6H, H$_{pyrrole}$) ppm.

$^{13}$C NMR (126 MHz, CDCl$_3$): δ=35.67 (CH$_2$), 72.86 (C≡CH), 80.09 (C≡CH), 105.31 (t, $J_{C-F}$=19.2 Hz, Ar—$C_{ipso}$), 118.59 ($C_{pyrrole}$), 125.89 (t, $J_{C-F}$=2.1 Hz, Ar—$C_{para}$), 127.44 ($C_{pyrrole}$), 137.86 (d, $J_{C-F}$=241.3 Hz, Ar—$C_{meta}$), 141.00 ($C_{meso}$), 144.90 ($C_{pyrrole}$), 145.05 (m, $J_{C-F}$=246.4 Hz, Ar—$C_{ortho}$) ppm.

$^{19}$F NMR (376 MHz, CDCl$_3$): δ=−158.33 ($m_c$, J=22.2, 7.6 Hz, 6F, Ar—$F_{meta}$), −140.97 ($m_c$, J=21.9, 7.7 Hz, 6F, Ar—$F_{ortho}$) ppm.

HRMS (ESI-TOF): m/z calc. for $C_{54}H_{30}F_{12}GaN_9Na^+$ [M+Na]$^+$ 1124.1581, found 1124.1566.

Reaction of Tris-[5-(4-prop-2-ynyloxy)-2,3,5,6-tetrafluorophenyl)]dipyrrinato gallium(III) with 8-(4-Azido-2,3,5,6-tetrafluorophenyl)-4,4-difluoro-4-bora-3a,4a-diaza-s-indacene

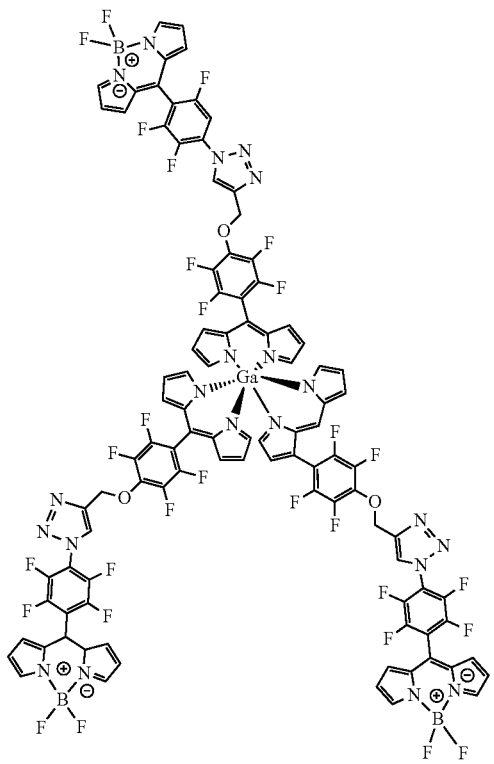

Under argon atmosphere and the exclusion of light, a mixture of tris-[5-(4-prop-2-ynyloxy)-2,3,5,6-tetrafluorophenyl)]dipyrrinato gallium(III) (117 mg, 0.10 mmol), azido-BODIPY (129 mg, 0.34 mmol, 3.2 eq), sodium ascorbate (374 mg, 1.89 mmol, 18 eq) and CuSO$_4$ 5H$_2$O (26 mg, 0.11 mmol, 1 eq) was dissolved in dry DMSO (5 mL) and stirred for 30 min at rt. The mixture was diluted with DCM and washed several times with water. The crude product was purified by column chromatography (silica gel, DCM) and recrystallized (DCM/n-pentane) to obtain the product as red crystals (48 mg, 20%).

Mp: 97-100° C.

$^1$H NMR (400 MHz, CDCl$_3$): δ=5.64 (s, 6H, CH$_2$), 6.40 (dd, J=4.2, 1.4 Hz, 6H, H$_{pyrrole}$), 6.50 (d, J=4.2 Hz, 6H, H$_{pyrrole}$), 6.61 (d, J=4.2 Hz, 6H, H$_{pyrrole}$), 6.88 (d, J=4.2 Hz, 6H, H$_{pyrrole}$), 7.63-7.65 (m, 6H, H$_{pyrrole}$), 7.99-8.02 (m, 6H, H$_{pyrrole}$), 8.21 (s, 3H, H$_{triazole}$) ppm.

$^{13}$C NMR (126 MHz, CDCl$_3$): δ=67.58 (CH$_2$), 111.21 (t, J$_{C-F}$=19.2 Hz, Ar—C$_{ipso}$), 114.73 (t, J$_{C-F}$=18.0 Hz, Ar—C$_{ipso}$), 118.89 (C$_{pyrrole}$), 120.33 (C$_{pyrrole}$), 125.87 (C$_{triazole}$), 127.33 (C$_{pyrrole}$), 130.50 (C$_{pyrrole}$), 136.90 (t, J$_{C-F}$=12.1 Hz, Ar—C$_{para}$) 1, 140.33 (C$_{meso}$), 141.50 (dd, J$_{C-F}$=265.1, 15.7 Hz, Ar—C$_{meta}$), 141.67 (dd, J$_{C-F}$=265.1, 15.7 Hz, Ar—C$_{meta}$), 143.74 (C$_{meso}$), 144.53 (d, J$_{C-F}$=249.2 Hz, Ar—C$_{ortho}$), 145.05 (d, J$_{C-F}$=249.2 Hz, Ar—C$_{ortho}$), 145.31 (C$_{pyrrole}$), 147.20 (C$_{pyrrole}$).

$^{19}$F NMR (376 MHz, CDCl$_3$): δ=−155.37 (m$_c$, J=21.3, 7.3 Hz, 6F, Ar—F$_{meta}$), 144.63 (m$_c$, J=28.0 Hz, 6F, BF$_2$), 144.04 (m$_c$, J=22.3, 10.8 Hz, 6F, Ar—F$_{meta}$), −139.45 J=21.4, 7.3 Hz, 6F, Ar—F$_{ortho}$), −134.49 (m$_c$, J=22.4, 10.9 Hz, 6F, Ar—F$_{ortho}$) ppm.

HRMS (ESI-TOF): m/z calc. for C$_{33}$H$_{17}$BF$_{10}$N$_7$O$^+$ [M+H]$^+$ 728.1422, found 728.1462.

UV/VIS (DCM): λ$_{max}$/nm [log(ε/L mol$^{-1}$ cm$^{-1}$)]=432 (4.89), 500 (4.92), 520 (5.16) nm.

Fluorescence: λ$_{max}$=545 nm at λ$_{Excitation}$=400 nm.

Tris[5-(4-β-D-thiogalactosyl)-2,3,5,6-tetrafluorophenyl)dipyrrinato gallium(III)

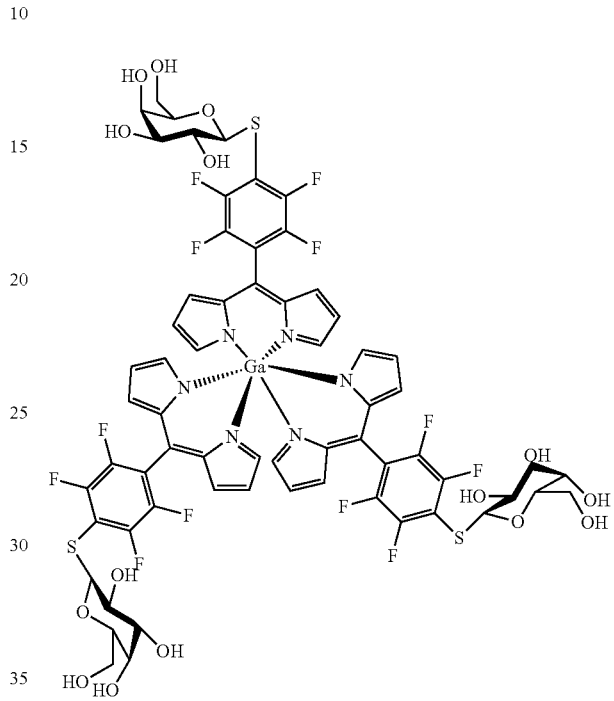

Under argon atmosphere and the exclusion of light tris[5-(pentafluorophenyl)dipyrrinato]gallium(III) (74 mg, 74 μmol) was dissolved in dry DMF (5 mL), β-D-thiogalactose sodium salt (73 mg, 0.33 mmol, 4.5 eq) was added and the mixture stirred for 1.5 h at rt. The mixture was evaporated to dryness and purified by column chromatography (silica gel, DCM/MeOH=85:15) to obtain the product as orange solid (100 mg, 88%).

Mp: >300° C.

$^1$H NMR (400 MHz, CD$_3$OD): δ=2.81 (d, J=0.6 Hz, 3H, CH$_2$), 2.94 (d, J=0.6 Hz, 3H, CH$_2$), 3.26-3.28 (m, 3H, H$_{galactose}$) 3.50-3.56 (m, 9H, H$_{galactose}$), 3.62-3.65 (m, 9H, H$_{galactose}$), 3.88-3.90 (m, 3H, H$_{galactose}$), 6.30 (dd, J=4.2, 1.4 Hz, 6H$_{pyrrole}$), 6.69 (d, J=4.1 Hz, 6H, H$_{pyrrole}$), 6.90-6.92 (m, 6H, H$_{pyrrole}$) ppm.

$^{13}$C NMR (126 MHz, CD$_3$OD): δ=30.58 (CH$_2$), 35.90 (CH$_2$), 61.39 (C$_{galactose}$), 61.47 (C$_{galactose}$), 69.38 (C$_{galactose}$), 71.35 (C$_{galactose}$), 74.83 (C$_{galactose}$), 112.82 (t, J$_{C-F}$=20.5 Hz, Ar—C$_{ipso}$), 117.90 (C$_{pyrrole}$), 131.42 (C$_{pyrrole}$), 138.19 (C$_{meso}$), 144.32 (dd, J$_{C-F}$=248.5, 16.0 Hz, Ar—C$_{meta}$), 147.06 (dd, J$_{C-F}$=246.6, 13.6 Hz, Ar—C$_{ortho}$), 150.00 (C$_{pyrrole}$) ppm.

$^{19}$F NMR (376 MHz, CD$_3$OD): δ=−142.37 (m$_c$, J=24.3, 11.1 Hz, 6F, Ar—F$_{meta}$), −133.82 (m$_c$, J=24.1, 11.1 Hz, Ar—F$_{meta}$) ppm.

HRMS (ESI-TOF): m/z calc. for C$_{63}$H$_{51}$F$_{12}$GaN$_6$NaO$_{15}$S$_3^+$ [M+K]$^+$ 1547.1531, found 1547.1522.

UV/VIS (MeOH): λ$_{max}$/nm [log(ε/L mol$^{-1}$ cm$^{-1}$)]=453 (5.02), 506 (4.99) nm.

Tris[5-(4-β-D-thioglucosyl)-2,3,5,6-tetrafluorophenyl)dipyrrinato gallium(III)

c) Fe(III) Complexes

Tris(pentafluorophenyl)dipyrrinato Iron(III)

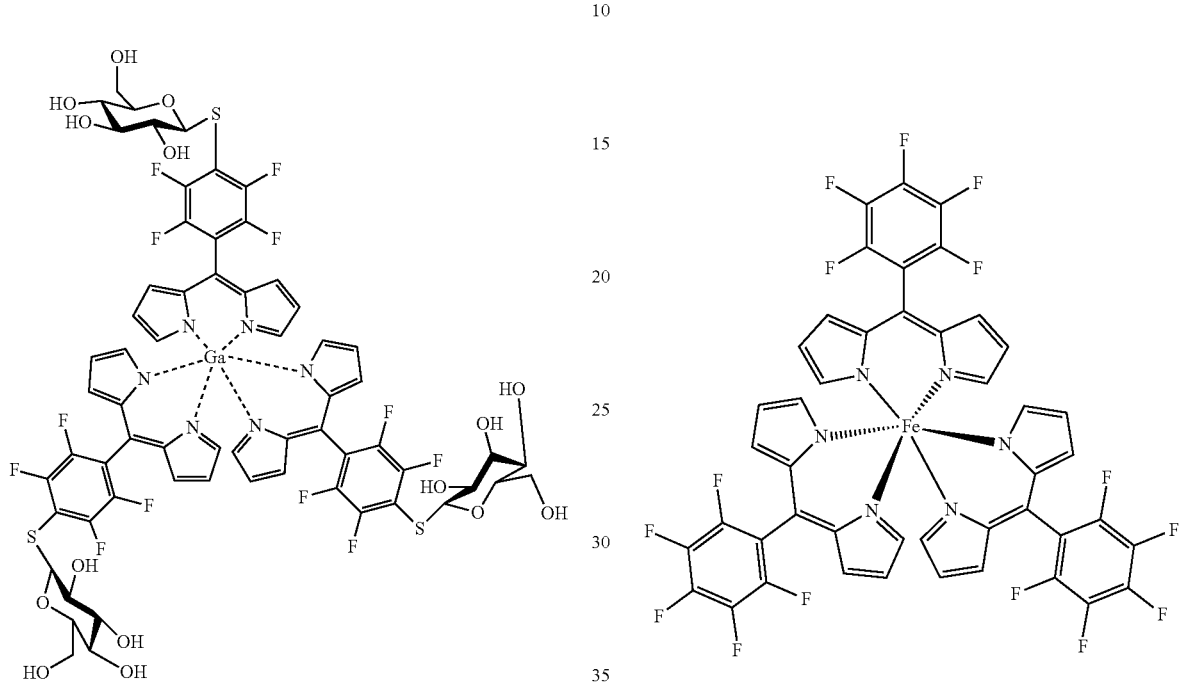

Under argon atmosphere and the exclusion of light a mixture of tris[5-(pentafluorophenyl)dipyrrinato]gallium(III) (67 mg, 67 µmol) and thioglucose sodium salt (55 mmg, 0.25 mmol, 3.7 eq) in THF (5 mL) was stirred for 40 min at rt. The mixture was evaporated to dryness and purified by column chromatography (silica gel, DCM/MeOH=8:2) to obtain the product as red solid (50 mg, 49%).

Mp: >300° C.

$^1$H NMR (400 MHz, CD$_3$OD): δ=3.25-3.45 (m, 22H, H$_{glucose}$), 3.57-3.63 (m, 3H, H$_{glucose}$), 3.77-3.79 (m, 2H, H$_{glucose}$), 3.80-3.82 (m, 1H, H$_{glucose}$), 4.90-4.94 (m, 6H, CH$_2$), 6.32 (dd, J=4.2, 1.4 Hz, 6H, H$_{pyrrole}$), 6.71 (d, J=4.1 Hz, H$_{pyrrole}$), 6.93-6.96 (m, 6H, H$_{pyrrole}$) ppm.

$^{13}$C NMR (126 MHz, CD$_3$OD): δ=61.46 (C$_{glucose}$), 70.17 (C$_{glucose}$), 74.44 (C$_{glucose}$), 78.24 (C$_{glucose}$), 81.11 (C$_{glucose}$), 81.13 (C$_{glucose}$), 85.34 (CH$_2$), 85.42 (CH$_2$), 112.82 (Ar—C$_{ipso}$), 117.77 (C$_{pyrrole}$), 130.36 (Ar—C$_{para}$) 131.36, (C$_{pyrrole}$), 138.19 (C$_{meso}$), 144.37 (dd, J=253.0, 16.4 Hz, Ar—C$_{meta}$), 146.93 (dd, J=244.2, 16.9 Hz, Ar—C$_{ortho}$), 149.94 (C$_{pyrrole}$) ppm.

$^{19}$F NMR (376 MHz, CD$_3$OD): δ=-142.47 (m$_c$, J=24.3, 11.3 Hz, 6F, Ar—F$_{meta}$), -134.60--134.30 (m, 6F, Ar—F$_{ortho}$) ppm.

HRMS (ESI-TOF): m/z calc. for C$_{42}$H$_{34}$F$_8$GaN$_4$O$_{10}$S$_2^+$ [M-L]$^+$ 1039.0844, found 1039.0765; m/z calc. for C$_{63}$H$_{51}$F$_{12}$GaN$_6$NaO$_{15}$S$_3^+$ [M+Na]$^+$ 1547.1531; found 1547.1420.

UV/VIS (MeOH): λ$_{max}$/nm [log(ε/L mol$^{-1}$ cm$^{-1}$)]=453 (4.89), 505 (4.82) nm.

Under argon atmosphere 5-(pentafluorophenyl)dipyrrin (100 mg, 0.32 mmol, 3.1 eq) was dissolved in dry MeOH (10 mL), FeCl$_3$·6H$_2$O (27 mg, 0.10 mmol) and DIPEA (0.24 mL, 186 mg, 1.44 mmol, 14 eq) were added and the mixture was stirred for 30 min at 50° C. The mixture was diluted with DCM and washed several times with water. The organic layer was dried with sodium sulfate, filtered and evaporated to dryness. The crude product was purified by column chromatography (silica gel, DCM) and recrystallized to obtain the product as black solid (60 mg, 61%).

Mp: 240-245° C.

$^1$H NMR (400 MHz, CDCl$_3$): δ=-28.47 (br s, 3H, NH), -7.48 (m, 6H, H$_{pyrrole}$), -5.98 (m, 6H, H$_{pyrrole}$), 7.28 (m, 6H, H$_{pyrrole}$) ppm.

$^{19}$F NMR (376 MHz, CDCl$_3$): δ=-159.82--159.62 (m, 6F, Ar—F$_{meta}$), -151.40 (t, J$_{C-F}$=20.7 Hz, 3F, Ar—F$_{para}$) -138.38--135.20 (m, 6F, Ar—F$_{ortho}$) ppm.

HRMS (ESI-TOF): m/z calc for C$_{45}$H$_{18}$F$_{15}$FeKN$_6^+$ [M+K]$^+$ 1022.0334, found 1022.0342.

UV/VIS (DCM): λ$_{max}$/nm [log(ε/L mol$^{-1}$ cm$^{-1}$)]=450 (4.81), 500 (4.70) nm.

The data are in accordance with the literature (J-Y. Shin, B. O. Patrick, S. B. Son, J. R. Hahn, D. Dolphin, Structural Studies of the Self-Assemblies Created with Dipyrrins, Bull. Korean Chem. Soc. 2010, 4, 1004-1013)

33
Tris[5-(4-butyloxy)-2,3,5,6-tetrafluorophenyl]dipyrrin iron(III)

34
Tris[5-(4-prop-enyloxy)2,3,5,6-tetrafluorophenyl]dipyrrinato iron (III)

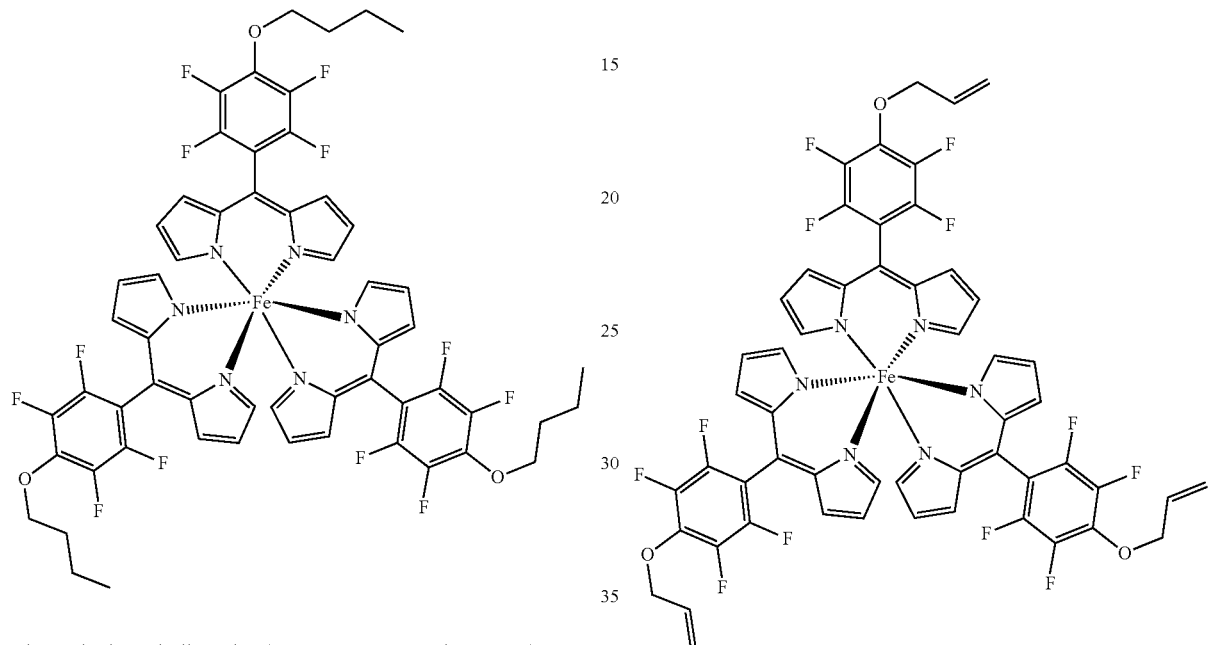

The substituted dipyrrin (91 mg, 240 μmol, 3.1 eq) was dissolved in dry MeOH (10 mL), FeCl$_3$.6H$_2$O (21 mg, 80 μmol) and DIPEA (0.6 mL, 1.12 mmol, 14 eq) were added and the mixture was stirred for 30 min at 50° C. The mixture was evaporated to dryness and purified by column chromatography (silica gel, DCM/n-hexane=1:1) to obtain the product as green solid (38 mg, 41%).

Mp: 235-238° C.

$^1$H NMR (400 MHz, CDCl$_3$): δ=−29.14 (br s, 6H, H$_{pyrrole}$), −7.65 (br s, 6H, H$_{pyrrole}$), −6.36 (br s, 6H, H$_{pyrrole}$), 1.37 (t, J=7.4 Hz, 9H, CH$_3$), 1.98-2.10 (m, 6H, CH$_2$), 2.34-2.42 (m, 6H, CH$_2$), 5.10 (t, J=6.4 Hz, 6H, CH$_2$) ppm.

$^{13}$C NMR (126 MHz, CDCl$_3$): δ=14.20 (CH$_3$), 19.42 (CH$_2$), 32.62 (CH$_2$), 43.87 (C$_{pyrrole}$), 75.97 (CH$_2$), 108.31 (Ar—C$_{ipso}$), 126.28 (C$_{meso}$), 134.20 (C$_{pyrrole}$), 136.16 (Ar—C$_{para}$) 143.40 (dd, J$_{C-F}$=249.5, 54.7 Hz, Ar—C) ppm.

$^{19}$F NMR (376 MHz, CDCl$_3$): δ=−155.62 (m$_c$, J=18.0 Hz, 6F, Ar—F$_{meta}$), −137.32 (m$_c$, J=16.5 Hz, 6F, Ar—F$_{ortho}$) ppm.

HRMS (ESI-TOF): m/z calc. for C$_{38}$H$_{30}$F$_8$FeN$_4$O$_2^+$ [M−L]$^+$ 782.1590, found 782.1567; m/z calc. for C$_{57}$H$_{45}$F$_{12}$FeN$_6$NaO$_3^+$ [M+K]$^+$ 1168.2603, found 1168.2582.

UV/VIS (DCM): λ$_{max}$/nm [log(ε/L mol$^{-1}$ cm$^{-1}$)]=451 (4.69), 505 (4.55).

The substituted dipyrrin (161 mg, 0.462 mmol, 3.1 eq) was dissolved in MeOH (10 mL), FeCl$_3$.6H$_2$O (40 mg, 0.149 mmol) and DIPEA (20 μL, 16 mg, 2.08 mmol, 14 eq) were added and the mixture was stirred at 50° C. for 1 h. The mixture was evaporated to dryness and purified by column chromatography (silica gel, DCM/n-hexane=1:2) to obtain the product as green crystals (106 mg, 65%).

Mp: >300° C.

$^1$H NMR (400 MHz, CDCl$_3$): δ=−29.54 (br s, 6H, H$_{pyrrole}$), −7.72 (brs, 6H, H$_{pyrrole}$), −6.39 (brs, 6H, H$_{pyrrole}$), 5.58 (d, J=6.0 Hz, 6H, CH$_2$), 5.84 (dd, J=17.2, 13 Hz, 3H, C=CH$_2$), 6.04 (dd, J=17.2, 13 Hz, 3H, C=CH$_2$), 6.64-6.76 (m, 3H, CH) ppm.

$^{19}$F NMR (376 MHz, CDCl$_3$): δ=−154.72 (m$_c$, J=17.7 Hz, 6F, Ar—F$_{meta}$), −137.19 (m$_c$, J=16.4 Hz, 6F, Ar—F$_{ortho}$) ppm.

HRMS (ESI-TOF): m/z calc. for C$_{54}$H$_{33}$F$_{12}$FeKN$_6$O$_3^+$ [M+K]$^+$ 1136.1404, found 1136.1371; m/z calc. for C$_{36}$H$_{22}$F$_8$FeN$_4$O$_2^+$ [M−L]$^+$ 750.0964, found 750.0938.

UV/VIS (DCM): λ$_{max}$/nm [log(ε/L mol$^{-1}$ cm$^{-1}$)]=450 (3.83) nm.

35
Tris[5-(4-prop-2-ynyloxy)-2,3,5,6-tetrafluorophenyl) dipyrrinato iron(III)

36
Tris[5-(4-N-hexylamino)-2,3,5,6-tetrafluorophenyl] dipyrrinato iron(III)

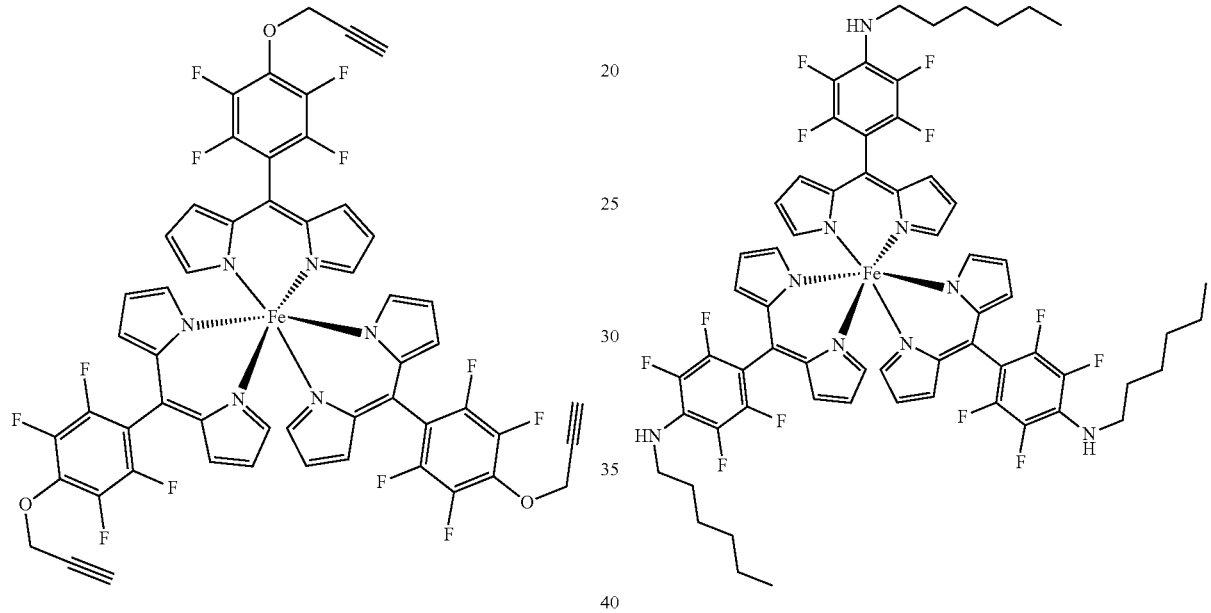

The substituted dipyrrin (100 mg, 0.28 mmol, 3.1 eq) was dissolved in MeOH (8 mL), FeCl$_3$.6H$_2$O (25 mg, 90 µmol) and DIPEA (0.2 mL, 162 mg, 1.26 mmol, 14 eq) were added and the mixture stirred for 2 h at 50° C. The mixture was evaporated to dryness and purified by column chromatography (silica gel, DCM/n-hexane=1:1) to obtain the product as red solid (20 mg, 20%).

Mp: >300° C.

$^1$H NMR (400 MHz, CDCl$_3$): δ=−29.47 (br s, 6H, H$_{pyrrole}$), −7.78 (br s, 6H, H$_{pyrrole}$), −6.33 (br s, 6H, H$_{pyrrole}$), 3.15-3.20 (m, 3H, C≡CH), 5.65-5.73 (m, 6H, CH$_2$), ppm.

$^{19}$F NMR (376 MHz, CDCl$_3$): δ=−153.92 (m$_c$, J=17.9 Hz, 6F, Ar—F$_{meta}$), −136.80 (m$_c$, J=17.0 Hz, Ar—F$_{ortho}$) ppm.

HRMS (ESI-TOF): m/z calc. for C$_{36}$H$_{18}$F$_8$FeN$_4$O$_2^+$ [M−L]$^+$ 746.0651, found 746.0640; m/z calc for C$_{54}$H$_{27}$F$_{12}$FeN$_6$NaO$_3^+$ [M+Na]$^+$ 1114.1200, found 1114.1181.

UV/VIS (DCM): λ$_{max}$/nm [log(ε/L mol$^{-1}$ cm$^{-1}$)]=445 (4.63), 450 (3.57) nm.

A mixture of the substituted dipyrrin (100 mg, 0.255 mmol, 3.1 eq), FeCl$_3$. 6H$_2$O (22 mg, 82 µmol) and DIPEA (0.19 mL, 1.14 mmol, 14 eq) was dissolved in MeOH (3 mL) and stirred for 1.5 h at 50° C. The mixture was evaporated to dryness and purified by column chromatography (silica gel, DCM/n-hexane=1:2) to obtain the product as black solid (24 mg, 21%).

Mp: 205-208° C.

$^1$H NMR (400 MHz, CDCl$_3$): δ=−29.55 (brs, 6H, H$_{pyrrole}$), −7.44 (br s, 6H, H$_{pyrrole}$), −6.43 (br s, 6H, . H$_{pyrrole}$), 1.18 (t, J=7.1 Hz, 9H, CH$_3$), 1.60-1.75 (m, 12H, CH$_2$), 1.85-1.95 (m, 6H, CH$_2$), 2.20-2.30 (m, 6H, CH$_2$), 4.15-4.20 (m, 6H, CH$_2$), 4.83 (br s, 3H, NH) ppm.

$^{19}$F NMR (376 MHz, CDCl$_3$): δ=−159.65 (m$_c$, J=18.3 Hz, 6F, Ar—F$_{meta}$), −138.52 (m$_c$, J=16.5 Hz, Ar—F$_{ortho}$) ppm.

HRMS (ESI-TOF): m/z calc. for C$_{42}$H$_{40}$F$_8$FeN$_6^+$ [M−L]$^+$ 836.2536, found 836.2548; m/z calc. for C$_{63}$H$_{60}$F$_{12}$FeN$_9$Na [M+Na]$^+$ 1249.4027, found 1249.4057.

UV/VIS (DCM): λ$_{max}$nm [log(ε/L mol$^{-1}$ cm$^{-1}$)]=449 (4.72), 500 (4.60) nm.

37

Tris[5-(4-N-prop-2-enylamino)-2,3,5,6-tetrafluorophenyl)dipyrrinato iron(III)

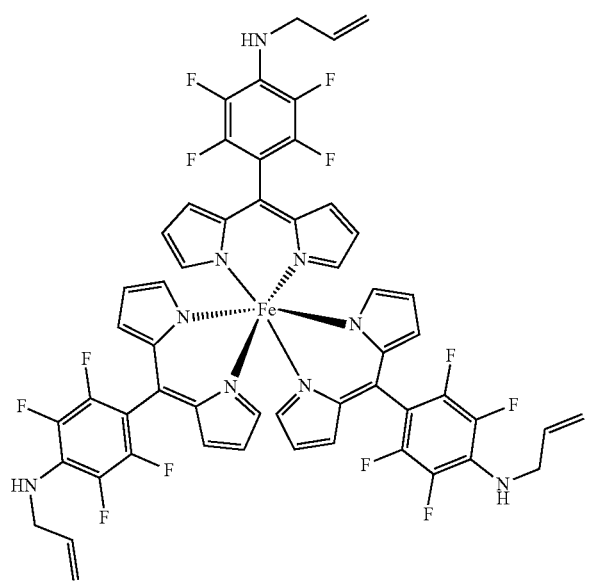

Under argon atmosphere the substituted dipyrrin (99 mg, 0.28 mmol, 3.1 eq) was dissolved in MeOH (5 mL), $FeCl_3 \cdot 6H_2O$ (24 mg, 92 µmol) and DIPEA (0.21 mL, 166 mg, 1.28 mmol, 14 eq) were added and the mixture stirred for 3 d at 50° C. The mixture was evaporated to dryness and purified by column chromatography (silica gel, DCM/n-hexane=1:1) to obtain the product as red solid (30 mg, 30%).

Mp: 225-230° C.

$^1$H NMR (400 MHz, $CDCl_3$): δ=−29.54 (brs, 6H, $H_{pyrrole}$), −7.50 (brs, 6H, $H_{pyrrole}$), 6.41 (brs, 6H, $H_{pyrrole}$), 4.77 (t, J=5.9 Hz, 6H, $CH_2$), 4.97 (brs, 3H, NH), 5.68 (dd, J=10.3, 0.8 Hz, 3H, C=$CH_2$), 5.88 (dd, J=10.3, 0.8 Hz, 3H, C=$CH_2$), 6.50-6.62 (m, 3H, CH) ppm.

$^{19}$F NMR (376 MHz, $CDCl_3$): δ=−158.44 ($m_c$, J=18.4 Hz, 6F, Ar—$F_{meta}$), 138-27 ($m_c$, J=17.2 Hz, 6F, Ar—$F_{ortho}$) ppm.

HRMS (ESI-TOF): m/z calc. for $C_{36}H_{24}F_8FeN_6^+$ [M−L]$^+$ 748.1284, found 748.1302; m/z calc. for $C_{54}H_{35}F_{12}FeN_9^+$ [M−H]$^+$ 1093.2173, found 1093.2187; m/z calc. for $C_{54}H_{36}F_{12}FeN_9Na^+$ [M+Na]$^+$ 1117.2149, found 1117.2166; m/z calc. for $C_{54}H_{36}F_{12}FeKN_9^+$ [M+K]$^+$ 1133.1889, found 1133.1904.

UV/VIS (DCM): $\lambda_{max}$/nm [log(ε/L mol$^{-1}$ cm$^{-1}$)]=450 (5.16), 500 (5.01) nm.

38

Tris[5-(4-N-prop-ynylamino)-2,3,5,6-tetrafluorophenyl)dipyrrinato iron(III)

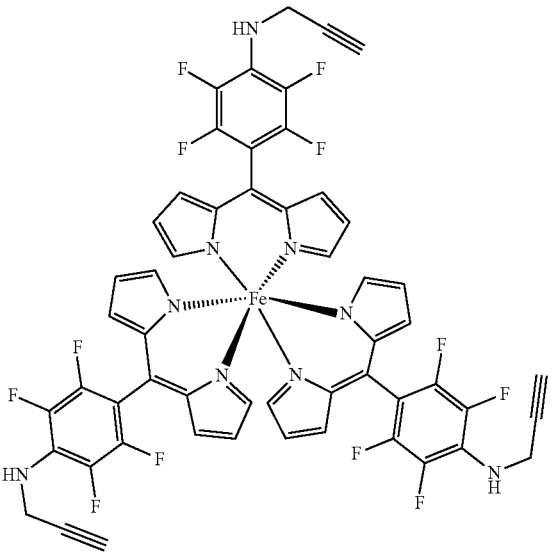

Under an argon atmosphere a mixture of the substituted dipyrrin (130 mg, 0.374 mmol, 3.1 eq), DIPEA (0.28 mL, 216 mg, 1.68 mmol, 14 eq) and $FeCl_3 \cdot 6H_2O$ (32 mg, 0.120 mmol) in MeOH (5 mL) was stirred at 50° C. for 2 h. The mixture was evaporated to dryness and purified by column chromatography (silica gel, DCM/n-hexane=1:1) to obtain the product as red solid (27 mg, 66%).

Mp: >300° C.

$^1$H NMR (400 MHz, $CDCl_3$): δ=−29.47 (br s, 6H, $H_{pyrrole}$), −7.57 (m, 6H, $H_{pyrrole}$), 6.36 (m, 6H, $H_{pyrrole}$), 2.82 (t, J=2.3 Hz, 3H, C≡CH), 4.88-4.92 (m, 6H, $CH_2$), 5.04-5.12 (m, 3H, NH) ppm.

$^{19}$F NMR (376 MHz, $CDCl_3$): δ=−157.20 ($m_c$, J=18.2 Hz, 6F, Ar—$F_{meta}$), −137.77 ($m_c$, J=16.3 Hz, 6F, Ar—$F_{ortho}$) ppm.

HRMS (ESI-TOF): m/z calc. for $C_{54}H_{30}F_{12}FeN_9Na^+$ [M+Na]$^+$ 1111.1674, found 1111.1738; m/z calc. for $C_{54}H_{30}F_{12}FeKN_9^+$ [M+K]$^+$ 1127.1414, found 1127.1476.

UV/VIS (DCM): $\lambda_{max}$/nm [log(ε/L mol$^{-1}$ cm$^{-1}$)]=448 (4.86), 500 (4.74) nm.

39

Tris[5-(4-β-D-thiogalactosyl)-2,3,5,6-tetrafluorophenyl)dipyrrinato iron(III)

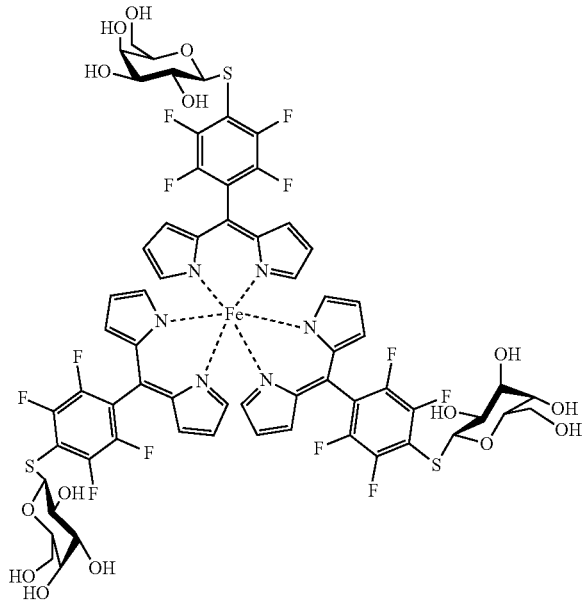

Under argon atmosphere and the exclusion of light tris[5-(pentafluorophenyl)dipyrrinato]iron(III) (100 mg, 0.10 mmol) was dissolved in dry DMF (5 mL), β-D-thiogalactose sodium salt (93 mg, 0.43 mmol, 4.5 eq) was added and the mixture stirred for 3 h at rt. The mixture was evaporated to dryness and purified by column chromatography (silica gel, DCM/MeOH=85:15) to obtain the product as orange solid (50 mg, 32%).

Mp: >300° C.

$^1$H NMR (400 MHz, CDCl$_3$): δ=−29.19 (brs, 6H, H$_{pyrrole}$), −7.41 (d, J=17.0 Hz, 6H, H$_{pyrrole}$), −6.55 (brs, 6H, H$_{pyrrole}$), 3.48-3.51 (m, 4H, H$_{galactose}$) 3.56-3.59 (m, 4H, H$_{galactose}$), 3.66-3.70 (m, 4H, H$_{galactose}$), 4.40 (s, 2H, CH$_2$), 4.42 (s, 2H, CH$_2$), 4.57-4.59 (brs, 12H, OH) ppm.

$^{19}$F NMR (376 MHz, CDCl$_3$): δ=−138.87 (m$_c$, J=18.5 Hz, 6F, Ar—F$_{meta}$), −132.97 (m$_c$, J=19.6 Hz, Ar—F$_{ortho}$) ppm.

HRMS (ESI-MS): m/z calc. for C$_{63}$H$_{51}$F$_{12}$FeN$_6$NaO$_{15}$S$_3^+$ [M+Na]$^+$ 1534.1625, found 1534.1659.

UV/VIS (MeOH): λ$_{max}$/nm [log(ε/L mol$^{-1}$ cm$^{-1}$)]=455 (4.99), 508 (4.90) nm.

40

Tris[5-(4-β-D-thioglucosyl)-2,3,5,6-tetrafluorophenyl)dipyrrinato iron(III)

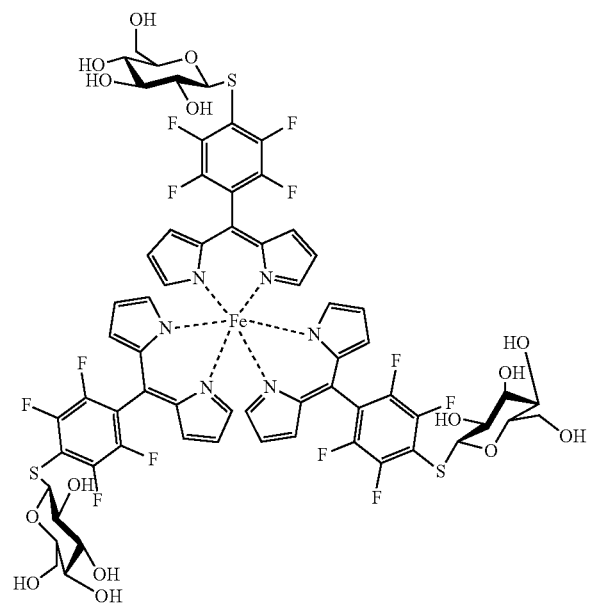

Under argon atmosphere tris[5-(pentafluorophenyl)dipyrrinato]iron(III) (61 mg, 62 µmol) was dissolved in dry DMF (5 mL), thio-glucose sodium salt (57 mg, 0.26 mmol, 4.2 eq) was added and the mixture stirred for 40 min at rt. The mixture was evaporated to dryness and the crude product was purified by column chromatography (silica gel, DCM/MeOH=85:15) to obtain the product as black solid (20 mg, 21%).

Mp: 175-180° C.

$^1$H NMR (400 MHz, CDCl$_3$): δ=−26.88 (brs, 6H, H$_{pyrrole}$), −5.02 (d, J=14.7 Hz, 6H, H$_{pyrrole}$), −4.18 (brs, 6H, H$_{pyrrole}$), 5.74-5.80 (m, 2H, CH), 5.86-5.92 (m, 1H, CH), 6.00-6.30 (m, 16H, CH, OH), 6.40-6.50 (m, 2H, CH$_2$), 6.60-6.70 (m, 2H, CH$_2$), 8.01-8.10 (m, 2H, CH$_2$) ppm.

$^{19}$F NMR (376 MHz, CDCl$_3$): δ=−138.95--138.65 (m, 6F, Ar—F$_{meta}$), −133.35 (m, 6F, Ar—F$_{ortho}$) ppm.

HRMS (ESI-TOF): m/z calc. for C$_{63}$H$_{51}$F$_{12}$FeN$_6$NaO$_{15}$S$_3^+$ [M+Na]$^+$ 1534.1630, found 1534.1611.

UV/VIS (MeOH): λ$_{max}$/nm [log(ε/L mol$^{-1}$ cm$^{-1}$)]=453 (4.67), 500 (4.59) nm.

Example 3

Preparation of Ruthenium Complexes [Ru(dpm)(bpy)$_2$ Complexes]

[Bis(2,2'-bipyridyl)-(5-pentafluorophenyl)dipyrrinato)]ruthenium(II) chloride

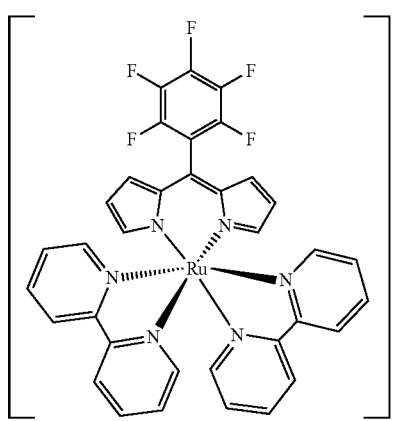

Under argon atmosphere 5-(pentafluorophenyl)dipyrrin (180 mg, 0.31 mmol) was dissolved in dry EtOH (20 mL), 2,2'-bipyridin (97 mg, 0.62 mmol, 2 eq) was added and the mixture was refluxed for 24 h. The mixture was diluted with DCM and washed with water several times. The organic layer was dried with sodium sulfate, filtered and evaporated to dryness. The crude product was purified by column chromatography (silica gel, DCM to DCM/MeOH=8:1) to obtain the product as black-green solid (160 mg, 68%).

Mp: 168-170° C.

$^1$H NMR (400 MHz, CDCl$_3$): δ=6.29 (dd, J=4.4, 1.4 Hz, 2H, H$_{pyrrole}$), 6.37 (t, J=1.3 Hz, 2H, H$_{pyrrole}$), 6.53 (d, J=4.3 Hz, 2H, H$_{pyrrole}$), 7.25-7.32 (m, 4H, H$_{bipyr}$), 7.65 (dd, J=5.6, 0.7 Hz, 2H, H$_{bipyr}$), 7.89-7.95 (m, 4H, H$_{bipyr}$), 7.97-8.02 (m, 2H, H$_{bipyr}$), 8.71-8.79 (m, 4H, H$_{bipyr}$) ppm.

$^{13}$C NMR (126 MHz, CDCl$_3$): δ=113.39 (t, J$_{C-F}$=19.3 Hz, Ar—C$_{ipso}$), 119.67 (C$_{pyrrole}$), 126.34 (C$_{bipyr}$), 126.81 (C$_{bipyr}$), 129.77 (C$_{pyrrole}$), 134.47 (C$_{meso}$), 136.18 (C$_{bipyr}$), 136.88 (C$_{bipyr}$), 138.32 (t, J$_{C-F}$=15.5 Hz, Ar—C$_{para}$), 141.33 (d, J$_{C-F}$=242.8 Hz, Ar—C$_{meta}$), 144.68 (d, J$_{C-F}$=244.9 Hz, Ar—C$_{ortho}$), 150.74 (C$_{pyrrole}$), 150.58 (C$_{bipyr}$), 151.82 (C$_{bipyr}$), 157.39 (C$_{bipyr}$), 158.17 (C$_{bipyr}$) ppm.

$^{19}$F NMR (376 MHz, CDCl$_3$): δ=−161.20−−161.00 (m, 2F, Ar—F$_{meta}$), −152.91 (t, J=20.8 Hz, 1F, Ar—F$_{para}$), −139.88-139.76 (m$_c$, J=23.1, 6.7 Hz, 2F, Ar—F$_{ortho}$) ppm.

HRMS (ESI-TOF): δ=m/z calc. for C$_{35}$H$_{22}$F$_5$N$_6$Ru$^+$ [M]$^+$ 723.0864, found 723.0900.

UV/VIS (DCM): λ$_{max}$/nm [log(ε/L mol$^{-1}$ cm$^{-1}$)]=471 (4.66), 513 (4.07) nm.

[Bis(2,2'-bipyridyl)-(4-N-hexylamino)-2,3,5,6-tetrafluorophenyl)dipyrrinato)]ruthenium(II) chloride

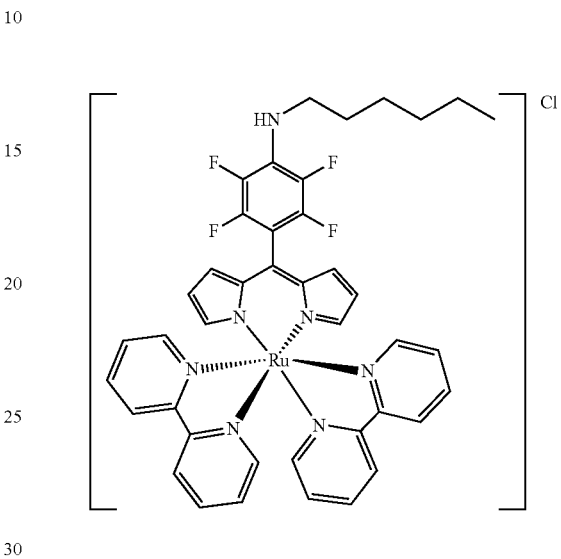

Under argon atmosphere [bis(2,2'-bipyridyl)-(5-pentafluorophenyl)dipyrrinato)]ruthenium(II) chloride (70 mg, 92 μmol) was dissolved in dry DMSO (3.0 mL), hexylamine (0.2 mL, 154 mg, 1.52 mmol, 16 eq) was added and the mixture was stirred for 1 hour at 80° C. The mixture was diluted with DCM and washed with water several times. The organic layer was dried with sodium sulfate, filtered and evaporated to dryness. Further purification was achieved by column chromatography (silica gel, DCM/MeOH=85:15) and recrystallisation (DCM/n-pentane) to obtain the product as black solid (33 mg, 43%).

Mp: 157-160° C.

$^1$H NMR (400 MHz, CDCl$_3$): δ=0.90 (t, J=6.9 Hz, 3H, CH$_3$), 1.30-1.45 (m, 4H, CH$_2$), 1.60-1.70 (m, 4H, CH$_2$), 3.42-3.49 (m, 2H, CH$_2$), 3.82 (br s, 1H, NH), 6.28 (dd, J=4.4, 1.4 Hz, 2H, H$_{pyrrole}$), 6.34-6.35 (m, 2H, H$_{pyrrole}$), 6.67 (d, J=4.3 Hz, 2H, H$_{pyrrole}$), 7.30 (dd, J=12.9, 6.4 Hz, 4H, H$_{bipyr}$), 7.68 (d, J=5.5 Hz, 2H, H$_{bipyr}$), 7.88-7.93 (m, 2H, H$_{bipyr}$), 7.99 (d, J=6.1 Hz, 4H, H$_{bipyr}$), 8.63 (dd, J=14.0, 8.1 Hz, 4H, H$_{bipyr}$) ppm.

$^{13}$C NMR (126 MHz, CDCl$_3$): δ=14.08 (CH$_3$), 22.65 (CH$_2$), 26.42 (CH$_2$), 30.90 (CH$_2$), 31.56 (CH$_2$), 46.01 (CH$_2$), 119.02 (C$_{pyrrole}$), 124.01 (C$_{bipyr}$), 124.07 (C$_{bipyr}$), 126.30 (C$_{bipyr}$), 126.81 (C$_{bipyr}$), 130.39 (C$_{pyrrole}$), 135.60 (C$_{bipyr}$), 135.85 (C$_{bipyr}$), 136.63 (C$_{bipyr}$), 150.00 (C$_{pyrrole}$), 150.69 (C$_{bipyr}$), 152.05 (C$_{bipyr}$), 157.37 (C$_{bipyr}$), 158.15 (C$_{bipyr}$) ppm.

$^{19}$F NMR (376 MHz, CDCl$_3$): δ=−160.60−−160.48 (m$_c$, J=16.3 Hz, 2F, Ar—F$_{meta}$), −143.29 (m$_c$, J=15.7 Hz, 2F, Ar—F$_{ortho}$) ppm.

HRMS (ESI-TOF): m/z calc. for C$_{41}$H$_{36}$F$_4$N$_7$Ru+ [M]$^+$ 804.2006, found 804.2046.

UV/VIS (DCM): λ$_{max}$/nm [log(ε/L mol$^{-1}$ cm$^{-1}$)]=469 (4.68), 515 (4.07) nm.

[Bis(2,2'-bipyridyl(4-(prop-2-enylamino)-2,3,5,6-tetrafluorophenyl)dipyrrinato)]ruthenium(II) chloride

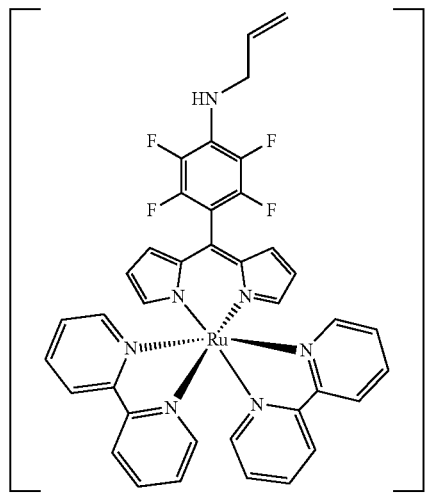

Under argon atmosphere [bis(2,2'-bipyridyl)-(5-pentafluorophenyl)dipyrrinato)]ruthenium(II) chloride (70 mg, 90 μmol) was dissolved in DMSO (3.0 mL), allylamine (0.13 mL, 105 mg, 1.84 mmol, 20 eq.) was added and the mixture was stirred at 80° C. for 1 hour. The mixture was diluted with DCM and washed with water several times. The organic layer was dried with sodium sulfate, filtered and evaporated to dryness. The crude product was purified by column chromatography (silica gel, DCM/MeOH=85:15) and recrystallisation (DCM/n-pentane) to obtain the product as black-green crystals (31 mg, 43%).

Mp: 172-175° C.

$^{1}$H NMR (400 MHz, CDCl$_3$): δ=4.04-4.16 (m, 2H, CH$_2$), 5.21 (dd, J=10.3, 0.9 Hz, 1H, C=CH$_2$), 5.30 (dd, J=17.1, 1.2 Hz, 1H, C=CH$_2$), 5.92-6.02 (m, 1H, CH), 6.27 (dd, J=4.4, 1.2 Hz, 2H, H$_{pyrrole}$), 6.33-6.35 (m, 2H, H$_{pyrrole}$), 6.65 (d, J=4.2 Hz, 2H, H$_{pyrrole}$), 7.24-7.32 (m, 4H, H$_{bipyr}$), 7.66 (d, J=5.2 Hz, 2H, H$_{bipyr}$), 7.89 (t, J=7.6 Hz, 2H, H$_{bipyr}$), 7.94-7.95 (m, 4H, H$_{bipyr}$), 8.60-8.72 (m, 4H, H$_{bipyr}$) ppm.

$^{13}$C NMR (126 MHz, CDCl$_3$): δ=48.16 (CH$_2$), 105.40 (t, J$_{C-F}$=20.0 Hz, Ar—C$_{ipso}$), 117.16 (C=CH$_2$), 119.07 (C$_{pyrrole}$), 124.12 (C$_{bipyr}$), 124.15 (C$_{bipyr}$), 126.30 (C$_{bipyr}$), 126.76 (C$_{bipyr}$), 128.05 (t, J=11.8 Hz, Ar—C$_{para}$), 130.31 (C$_{pyrrole}$), 131.34 (C$_{bipyr}$), 135.03 (CH), 135.50 (C$_{meso}$), 135.93 (C$_{bipyr}$), 136.66 (C$_{bipyr}$), 136.95 (d, J$_{C-F}$=245.3 Hz, Ar—C$_{meta}$), 144.89 (d, J$_{C-F}$=243.5 Hz, Ar—C$_{ortho}$), 150.05 (C$_{pyrrole}$), 150.63 (C$_{bipyr}$), 151.98 (C$_{bipyr}$), 157.36 (C$_{bipyr}$), 158.17 (C$_{bipyr}$) ppm.

$^{19}$F NMR (376 MHz, CDCl$_3$): δ=−159.74--−159.58 (m$_c$, J=17.2 Hz, 2F, Ar—F$_{meta}$), −143.21--−143.00 (m$_c$, J=15.6 Hz, 2F, Ar—F$_{ortho}$) ppm.

HRMS (ESI-TOF): m/z calc. for C$_{38}$H$_{28}$F$_4$N$_7$Ru$^+$ [M]$^+$ 760.75, found 760.1416.

UV/VIS (DCM): λ$_{max}$/nm [log(ε/L mol$^{-1}$ cm$^{-1}$)=469 (4.53), 518 (3.92) nm.

[Bis(2,2'-bipyridyl(4-(prop-2-ynylamino)-2,3,5,6-tetrafluorophenyl)dipyrrinato)]ruthenium(II) chloride

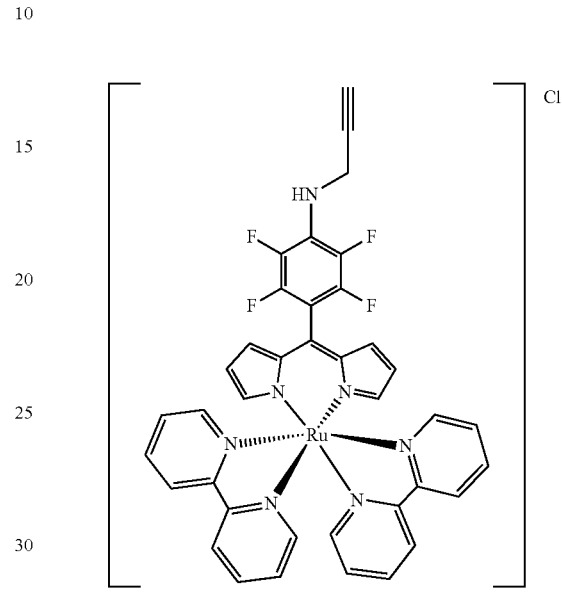

Under argon atmosphere [bis(2,2'-bipyridyl)-(5-pentafluorophenyl)dipyrrinato)]ruthenium(II) chloride (70 mg, 90 μmol) was dissolved in dry DMSO (3 mL), propargylamine (198 mg, 3.60 mmol, 0.23 mL, 40 eq) was added and the mixture stirred for 7 h at 80° C. The mixture was diluted with DCM and washed several times with water. The organic layer was dried with sodium sulfate, filtered and evaporated to dryness. The crude product was purified by column chromatography (silica gel, DCM/MeOH=85:15) and recrystallisation (DCM/n-pentane) to obtain the product as black crystals (29 mg, 41%).

Mp: >300° C.

$^{1}$H NMR (400 MHz, CDCl$_3$): δ=2.33 (t, J=1.5 Hz, 1H C≡H), 4.22-4.24 (m, 2H, CH$_2$), 6.29 (dd, J=4.4, 1.4 Hz, 2H, H$_{pyrrole}$), 6.36-6.38 (m, 2H, H$_{pyrrole}$), 6.65 (d, J=4.2 Hz, 2H, H$_{pyrrole}$), 7.28-7.32 (m, 4H, H$_{bipyr}$), 7.69 (d, J=4.8 Hz, 2H, H$_{bipyr}$), 7.90-7.95 (m, 2H, H$_{bipyr}$), 7.96-8.01 (m, 4H, H$_{bipyr}$), 8.63-8.70 (m, 4H, H$_{bipyr}$) ppm.

$^{13}$C NMR (126 MHz, CDCl$_3$): δ=35.73 (CH$_2$), 72.81 (C≡CH), 80.07 (C≡CH), 119.17 (C$_{pyrrole}$), 124.17 (C$_{bipyr}$), 124.23 (C$_{bipyr}$), 126.31 (C$_{bipyr}$), 126.80 (C$_{bipyr}$), 130.27 (C$_{pyrrole}$), 131.02 (C$_{bipyr}$), 135.33 (C$_{meso}$), 135.93 (C$_{bipyr}$), 136.70 (C$_{bipyr}$), 150.17 (C$_{pyrrole}$), 150.62 (C$_{bipyr}$), 152.00 (C$_{bipyr}$), 157.39 (C$_{bipyr}$), 158.17 (C$_{Bipyr}$) ppm.

$^{19}$F NMR (376 MHz, CDCl$_3$): δ=−158.50--−158.36 (m, 2F, Ar—F$_{meta}$), −142.58--−142.46 (m, 2F, Ar—F$_{ortho}$) ppm.

HRMS (ESI-TOF): m/z calc. for C$_{38}$H$_{26}$F$_4$N$_7$Ru$^+$ [M]$^+$ 758.1224, found 758.1291.

UV/VIS (DCM): λ$_{max}$/nm [log(ε/L mol$^{-1}$ cm$^{-1}$)=469 (4.53), 518 (3.92) nm.

45

[Bis(2,2'-bipyridyl)-(4-N-azidopropylamino)-2,3,5,6-tetrafluorophenyl)dipyrrinato)]ruthenium(II) chloride

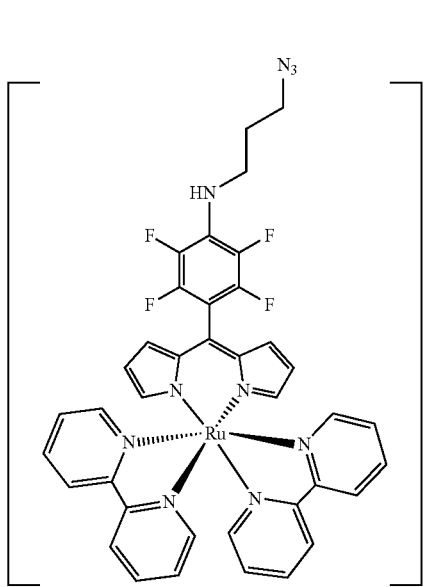

Under argon atmosphere [bis(2,2'-bipyridyl)-(5-pentafluorophenyl)dipyrrinato)]ruthenium(II) chloride (100 mg, 0.13 mmol) was dissolved in dry DMSO (3.0 mL), 3-azidopropylamine (5258 mg, 5.27 mmol, 40 eq) was added and the mixture was stirred for 6 h at 80° C. The mixture was diluted with DCM and washed with water several times. The organic layer was dried with sodium sulfate, filtered and evaporated to dryness. The crude product was purified by column chromatography (silica gel, DCM/MeOH=85:15) and recrystallisation (DCM/n-pentane) to obtain the product as black solid (49 mg, 45%).

Mp: 150-155° C.

IR (ATM): v=1545 ($N_3$) cm$^{-1}$.

$^1$H NMR (400 MHz, CDCl$_3$): δ=1.90-1.98 (m, 2H, CH$_2$), 3.45-3.51 (m, 2H, CH$_2$), 3.55-3.61 (m, 2H, CH$_2$), 4.20 (brs, 1H, NH), 6.27 (d, J=4.3 Hz, 2H, H$_{pyrrole}$), 6.33-6.35 (m, 2H, H$_{pyrrole}$), 6.64 (d, J=4.0 Hz, 2H, H$_{pyrrole}$) 7.26-7.30 (m, 4H, H$_{bipyr}$), 7.67 (d, J=5.3 Hz, 2H, H$_{bipyr}$), 7.84-7.92 (m, 2H, H$_{bipyr}$), 7.92-8.00 (m, 4H, H$_{bipyr}$), 8.50-8.60 (m, 4H, H$_{bipyr}$) ppm.

$^{13}$C NMR (126 MHz, CDCl$_3$): δ=29.98 (CH$_3$), 43.37 (CH$_2$), 49.14 (CH$_2$), 105.20 (t, J$_{C-F}$=19.8 Hz, Ar—C$_{ipso}$), 119.09 (C$_{pyrrole}$), 123.94 (C$_{bipyr}$), 126.32 (C$_{bipyr}$), 126.77 (C$_{bipyr}$), 128.15 (t, J$_{C-F}$=11.1 Hz, Ar—C$_{para}$), 130.33 (C$_{pyrrole}$), 135.50 (C$_{meso}$), 135.91 (C$_{bipyr}$), 136.61 (C$_{bipyr}$), 136.75 (d, J$_{C-F}$=231.8 Hz, Ar—C$_{meta}$), 144.89 (d, J$_{C-F}$=255 Hz, Ar—C$_{ortho}$), 150.06 (C$_{pyrrole}$), 150.71 (C$_{bipyr}$), 152.00 (C$_{bipyr}$), 157.33 (C$_{bipyr}$), 158.15 (C$_{bipyr}$) ppm.

$^{19}$F NMR (376 MHz, CDCl$_3$): δ=−160.21 (m$_c$, J=16.8 Hz, 2F, Ar—F$_{meta}$), −142.91 (m$_c$, J=16.9 Hz, 2F, Ar—F$_{ortho}$) ppm.

HRMS (ESI-TOF): m/z calc. for C$_{38}$H$_{29}$F$_4$N$_{10}$Ru$^+$ [M]$^+$ 803.1551, found 803.1559.

UV/VIS (DCM) λ$_{max}$/nm [log(ε/L mol$^{-1}$ cm$^{-1}$)]=468 (3.81) nm.

46

[Bis(2,2'-bipyridyl(4-(hexyloxy)-2,3,5,6-tetrafluorophenyl)dipyrrinato)]ruthenium(II) chloride

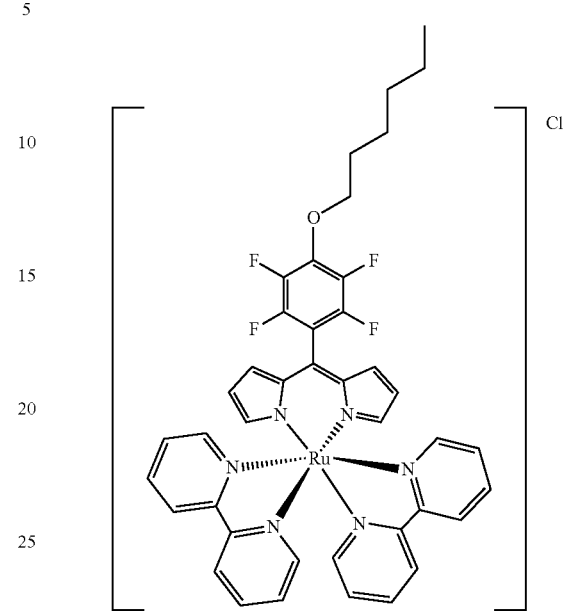

Under argon atmosphere and under exclusion of light [bis (2,2'-bipyridyl)-(5-pentafluorophenyl)dipyrrinato)]ruthenium(II) chloride (70 mg, 90 μmol) was dissolved in dry THF (3.0 mL), freshly powdered KOH (6.00 mg, 117 μmol, 1.3 eq) and hexanol (20 μL, 135 μmol, 13 mg, 1.5 eq) were added and the mixture was stirred for 2 hours at room temperature. Afterwards the mixture was diluted with DCM and washed several times with water. The organic layer was dried with sodium sulfate, filtered and evaporated to dryness. The crude product was purified by column chromatography (silica gel, DCM/MeOH=85:15) and recrystallisation (DCM/n-hexane) to obtain the product as black crystals (20 mg, 26%).

Mp: 137-140° C.

$^1$H NMR (400 MHz, CDCl$_3$): δ=0.91 (t, J=7.0 Hz, 3H, CH$_3$), 1.30-1.40 (m, 4H, CH$_2$), 1.45-1.55 (m, 2H, CH$_2$), 1.80-1.85 (m, 2H, CH$_2$), 4.32 (t, J=6.5 Hz, 2H, CH$_2$), 6.29 (dd, J=1.2, 4.5 Hz, 2H, H$_{pyrrole}$) 6.36-6.39 (m, 2H, H$_{pyrrole}$) 6.59 (d, J=4.1 Hz, 2H, H$_{pyrrole}$), 7.26-7.32 (m, 4H, H$_{bipyr}$), 7.68 (d, J=5.0 Hz, 2H, H$_{bipyr}$), 7.88-7.94 (m, 2H, H$_{bipyr}$), 7.94-8.00 (m, 4H, H$_{bipyr}$), 8.67 (dd, J=12.1, 8.3 Hz, 4H, H$_{bipyr}$) ppm.

$^{13}$C NMR (176 MHz, CDCl$_3$) δ=13.98 (CH$_3$), 22.54 (CH$_2$), 25.22 (CH$_2$), 29.92 (CH$_2$), 31.42 (CH$_2$), 75.53 (CH$_2$), 111.27 (t, J$_{C-F}$=13.1 Hz, Ar—C$_{ipso}$), 119.28 (C$_{pyrrole}$), 124.11 (C$_{bipyr}$), 126.26 (C$_{bipyr}$), 126.75 (C$_{bipyr}$), 130.02 (C$_{pyrrole}$), 134.85 (C$_{meso}$), 135.83 (C$_{bipyr}$), 136.68 (C$_{bipyr}$), 138.06 (m, Ar—F$_{para}$), 140.76 (dd, J$_{C-F}$=248.6, 13.1 Hz, Ar—C$_{meta}$), 144.76 (d, J$_{C-F}$=247.7 Hz, Ar—C$_{ortho}$), 150.33 (C$_{bipyr}$), 150.61 (C$_{pyrrole}$), 151.90 (C$_{bipyr}$), 157.33 (C$_{bipyr}$), 158.10 (C$_{bipyr}$) ppm.

$^{19}$F NMR (376 MHz, CDCl$_3$): δ=−156.90−−156.74 (m$_c$, J$_{C-F}$=22.5, 6.7 Hz, 2F, Ar—F$_{meta}$), −142.01−−141.89 (m$_c$, J$_{C-F}$=22.5, 6.7 Hz, 2F, Ar—F$_{ortho}$) ppm.

HRMS (ESI-TOF): m/z calc. for C$_{41}$H$_{35}$F$_4$N$_6$OR$^+$ [M]$^+$ 805.1852, found 805.1837.

UV/VIS (DCM): λ$_{max}$/nm [log(ε/L mol$^{-1}$ cm$^{-1}$)]=469 (4.84), 515 (4.19) nm.

47
[Bis(2,2'-bipyridyl(4-(prop-2-enyloxy)-2,3,5,6-tetrafluorophenyl)dipyrrinato)]ruthenium(II) chloride

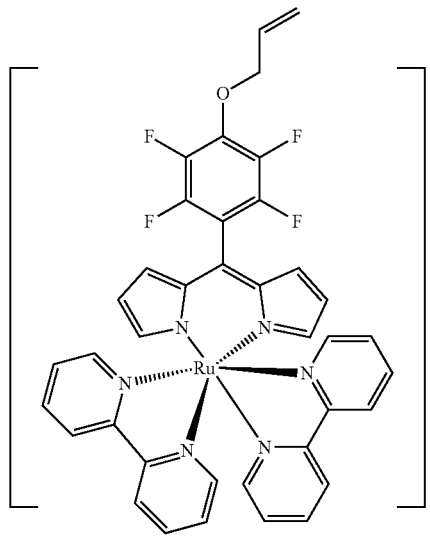

Under argon atmosphere and exclusion of light [bis(2,2'-bipyridyl)-(5-pentafluorophenyl)dipyrrinato)]ruthenium(II) chloride (70 mg, 92 µmol) was dissolved in dry THF (3.0 mL), freshly powdered KOH (7 mg, 0.12 mmol, 1.3 eq) and allylic alcohol (0.1 mL, 10 mg, 0.18 mmol, 2 eq) were added and the mixture was stirred for 2 h at rt. The mixture was diluted with DCM and washed with water several times. The organic layer was dried with sodium sulfate, filtered and evaporated to dryness. The crude product was purified by column chromatography (silica gel, DCM/MeOH=85:15) and recrystallisation (DCM/n-pentane) to obtain the product as black solid (59 mg, 80%).

Mp: >300° C.

$^1$H NMR (400 MHz, CDCl$_3$): δ=4.82 (d, J=6.1 Hz, 2H, CH$_2$), 5.35 (dd, J=10.3, 1.0 Hz, 1H, C=CH$_2$), 5.44 (dd, J=17.1, 1.3 Hz, 1H, C=CH$_2$), 6.00-6.10 (m, 1H, CH), 6.29 (dd, J=4.4, 1.4 Hz, 2H, H$_{pyrrole}$), 6.36-6.37 (m, 2H, H$_{pyrrole}$), 6.57 (d, J=4.3 Hz, 2H, H$_{pyrrole}$), 7.26-7.33 (m, 4H, H$_{bipyr}$), 7.67 (d, J=5.5 Hz, 2H, H$_{bipyr}$), 7.88-7.94 (m, 2H, H$_{bipyr}$), 7.94-8.02 (m, 4H, H$_{bipyr}$), 8.69-8.77 (m, 4H, H$_{bipyr}$) ppm.

$^{13}$C NMR (126 MHz, CDCl$_3$): δ=75.56 (CH$_2$), 111.87 (t, J$_{C-F}$=19.7 Hz, Ar—F$_{para}$), 119.38 (C$_{pyrrole}$), 120.32 (C=CH$_2$), 124.28 (C$_{bipyr}$), 124.32 (C$_{bipyr}$), 126.32 (C$_{bipyr}$), 126.80 (C$_{bipyr}$), 130.02 (C$_{pyrrole}$), 134.84 (C$_{meso}$), 136.05 (C$_{bipyr}$), 136.78 (C$_{bipyr}$), 137.17 (m, Ar—F$_{para}$), 140.95 (dd, J$_{C-F}$=250.0, 18.0 Hz, Ar—F$_{meta}$), 144.73 (d, J$_{C-F}$=249.0 Hz, Ar—F$_{ortho}$), 150.42 (C$_{bipyr}$), 150.60 (C$_{pyrrole}$), 157.39 (C$_{bipyr}$), 158.17 (C$_{bipyr}$) ppm.

$^{19}$F NMR (376 MHz, CDCl$_3$): δ=−156.10−−155.95 (m$_c$, J=22.6, 7.8 Hz, 2F, Ar—F$_{meta}$), −141.84−−141.72 (m$_c$, J=23.1, 7.5 Hz, 2F, Ar—F$_{ortho}$) ppm.

HRMS (ESI-TOF): m/z calc. for C$_{38}$H$_{27}$F$_4$N$_6$ORu$^+$ [M]$^+$ 761.1220, found 761.1290.

UV/VIS (DCM): λ$_{max}$/nm [log(ε/L mol$^{-1}$ cm$^{-1}$)]=469 (4.85), 516 (4.26) nm.

48
[Bis(2,2'-bipyridyl(4-(prop-2-ynyloxy)-2,3,5,6-tetrafluorophenyl)dipyrrinato)]ruthenium(II) chloride

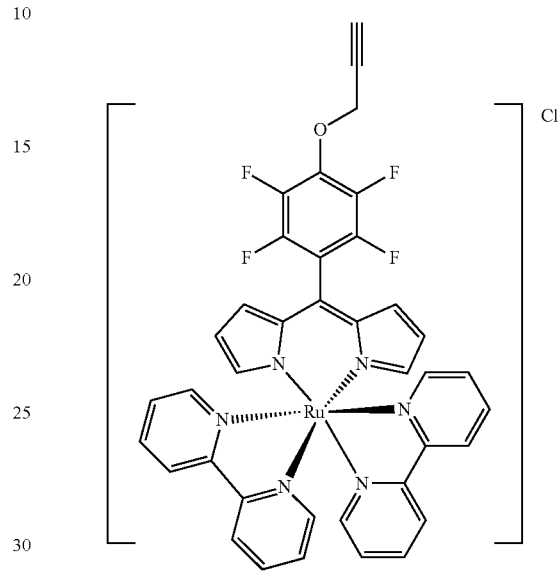

Under argon atmosphere and exclusion of light [bis(2,2'-bipyridyl)-(5-pentafluorophenyl)dipyrrinato)]ruthenium(II) chloride (70 mg, 92 µmol) was dissolved in dry THF (3.0 mL), freshly powdered KOH (7 mg, 0.12 mmol, 1.3 eq) and propargylic alcohol (0.1 mL, 100 mg, 0.18 mmol, 2 eq) were added and the mixture was stirred for 5 h at rt. The mixture was diluted with DCM and washed with water several times. The organic layer was dried with sodium sulfate, filtered and evaporated to dryness. Further purification was achieved by column chromatography (silica gel, DCM/MeOH=85:15) and recrystallisation (DCM/n-pentane) to obtain the product as black solid (45 mg, 62%).

Mp: >300° C.

$^1$H NMR (400 MHz, CDCl$_3$): δ=2.62 (t, J=2.4 Hz, 1H, CH), 4.99-5.00 (m, 2H, CH$_2$), 6.30 (dd, J=4.4, 1.4 Hz, 2H, H$_{pyrrole}$), 6.37-6.39 (m, 2H, H$_{pyrrole}$) 6.58 (d, J=4.3 Hz, 2H, H$_{pyrrole}$), 7.28-7.34 (m, 4H, H$_{bipyr}$), 7.69 (d, J=5.6 Hz, 2H, H$_{bipyr}$), 7.88-7.95 (m, 2H, H$_{bipyr}$), 7.95-8.01 (m, 4H, H$_{bipyr}$), 8.62-8.69 (m, 4H, H$_{bipyr}$) ppm.

$^{13}$C NMR (126 MHz, CDCl$_3$): δ=22.32 (CH), 61.73 (CH$_2$), 119.38 (C$_{pyrrole}$), 124.06 (C$_{bipyr}$), 124.08 (C$_{bipyr}$), 126.25 (C$_{bipyr}$), 126.76 (C$_{bipyr}$), 129.91 (C$_{pyrrole}$), 134.67 (C$_{meso}$), 135.95 (C$_{bipyr}$), 136.67 (C$_{bipyr}$), 150.42 (C$_{bipyr}$), 150.63 (C$_{pyrrole}$), 151.88 (C$_{bipyr}$), 157.33 (C$_{bipyr}$), 158.07 (C$_{bipyr}$) ppm.

$^{19}$F NMR (376 MHz, CDCl$_3$): δ=−155.21 (m$_c$, J=22.7, 8.4 Hz, Ar—C$_{meta}$), −141.37 (m$_c$, J=22.8, 8.2 Hz, Ar—C$_{ortho}$) ppm.

HRMS (ESI-TOF): m/z calc. for C$_{38}$H$_{26}$F$_4$N$_6$ORu$^{2+}$ [M+H]$^{2+}$ 760.1137, found 760.1109.

UV/VIS (DCM): λ$_{max}$/nm [log(ε/L mol$^{-1}$ cm$^{-1}$)]=469 (4.53), 518 (3.92) nm.

Reaction of [bis(2,2'-bipyridyl)-(4-prop-2-ynylamino)-2,3,5,6-tetrafluorophenyl)dipyrrinato)]ruthenium(II) chloride and 8-(azido-2,3,5,6-tetrafluorophenyl)-4,4-difluoro-4-bora-3a,4a-diaza-s-indacene

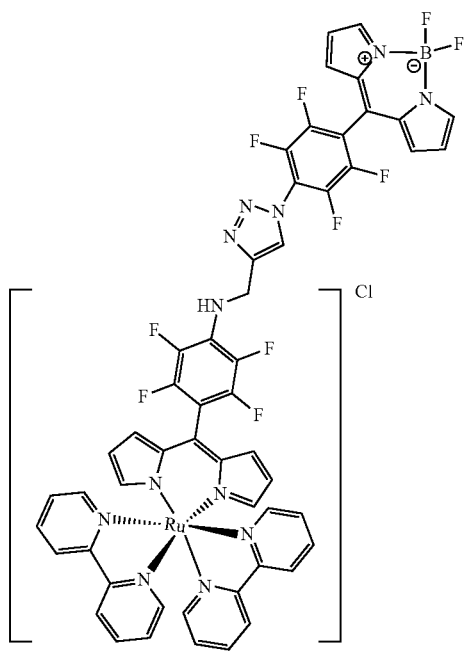

A mixture of [bis(2,2'-bipyridyl(4-(prop-2-ynylamino)-2,3,5,6-tetrafluorophenyl) dipyrrinato)]ruthenium(II) chloride (35 mg, 44 µmol), 8-(4-azido-2,3,5,6-tetrafluorophenyl)-BODIPY (33 mg, 88 µmol, 2 eq), $CuSO_4$ $5H_2O$ (5 mg, 22 µmol, 50 mol %) and sodium ascorbate (52 mg, 264 µmol, 6 eq) were dissolved in dry DMSO (3 mL) and stirred for 1 h under the exclusion of light. The mixture was diluted with DCM and washed several times with water. The organic layer was dried with sodium sulfate, filtered and evaporated to dryness. The crude product was purified by column chromatography (silica gel, DCM/MeOH=8:1) to obtain the product as black solid (25 mg, 48%).

Mp: >300° C.

$^1$H NMR (700 MHz, $CDCl_3$): δ=4.94 (d, J=6.7 Hz, 2H, $CH_2$), 6.27 (dd, J=4.4, 1.4 Hz, 2H, $H_{pyrrole}$), 6.34-6.35 (m, 2H, $H_{pyrrole}$), 6.60 (d, J=4.1 Hz, 2H, $H_{pyrrole}$), 6.63 (d, J=4.3 Hz, 2H, $H_{pyrrole}$), 6.94 (d, J=4.0 Hz, 2H, $H_{pyrrole}$), 7.29-7.32 (m, 4H, $H_{bipyr}$), 7.69 (d, J=5.6 Hz, 2H, $H_{bipyr}$), 7.88-7.92 (m, 2H, $H_{bipyr}$), 7.94-7.97 (m, 2H, $H_{bipyr}$), 7.98-7.99 (m, 2H, $H_{bipyr}$), 8.00 (m, 2H, $H_{pyrrole}$), 8.29 (s, 1H, $H_{triazol}$), 8.57-8.63 (m, 4H, $H_{bipyr}$) ppm.

$^{13}$C NMR (176 MHz, $CDCl_3$): δ=41.03 ($CH_2$), 119.08 ($C_{pyrrole}$), 120.11 ($C_{pyrrole}$), 123.63 ($C_{bipyr}$), 124.93 ($C_{triazol}$), 126.29 ($C_{bipyr}$), 126.70 ($C_{bipyr}$), 130.28 ($C_{pyrrole}$), 130.61 ($C_{pyrrole}$), 134.59 ($C_{meso}$), 135.36 ($C_{meso}$), 135.82 ($C_{bipyr}$), 136.52 ($C_{bipyr}$), 141.73 (dd, $J_{C-F}$=259.4, 15.0 Hz, Ar—$F_{meta}$), 144.69 (dd, $J_{C-F}$=247.7, 51.3 Hz, Ar—$C_{ortho}$), 146.97 ($C_{bipyr}$), 150.02 ($C_{pyrrole}$), 150.64 ($C_{bipyr}$), 151.99 ($C_{bipyr}$), 157.22 ($C_{bipyr}$), 158.08 ($C_{bipyr}$) ppm.

$^{19}$F NMR (376 MHz, $CDCl_3$): δ=-158.59 ($m_c$, J=17.0 Hz, 2F, Ar—$F_{meta}$), -144.67 ($m_c$, J=28.2 Hz, 2F, $BF_2$), -144.02 ($m_c$, J=22.5, 10.2 Hz, 2F, Ar—$F_{meta}$), -142.61 ($m_c$, J=16.9 Hz, 2F, Ar—$F_{ortho}$), -135.09 ($m_c$, $J_{C-F}$=22.5, 10.2 Hz, 2F, Ar—$F_{ortho}$) ppm.

HRMS (ESI-TOF): m/z calc. for $C_{53}H_{32}BF_{10}N_{12}Ru$ [M]$^+$ 1139.1844, found 1139.1956.

UV/Vis (DCM) $\lambda_{max}$/nm [log(ε/L mol$^{-1}$ cm$^{-1}$)]=470 (4.83), 520 (4.76) nm.

Reaction of [Bis(2,2'-bipyridyl)-(4-azidopropylamino)-2,3,5,6-tetrafluorophenyl)dipyrrinato)]ruthenium(II) chloride and 8-(4-N-Prop-2-ynylamino-2,3,5,6-tetrafluorophenyl)-4,4-difluoro-4-bora-3a,4a-diaza-s-indacene

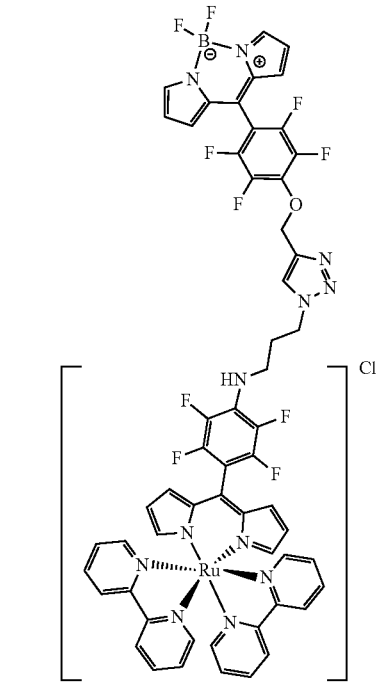

A mixture of [bis(2,2'-bipyridyl)-(4-N-azidopropylamino)-2,3,5,6-tetrafluorophenyl)dipyrrinato)]ruthenium(II) chloride (34 mg, 40 µmol), 8-(4-N-prop-2-ynylamino-2,3,5,6-tetrafluorophenyl)-BODIPY (32 mg, 81 µmol, 2 eq), $CuSO_4$ $5H_2O$ (10 mg, 40 µmol, 1 eq) and sodium ascorbate (47 mg, 240 µmol, 6 eq) was dissolved in dry DMSO (3 mL) and stirred for 1 h under the exclusion of light. The mixture was diluted with DCM and with water several times. The organic layer was dried with sodium sulfate, filtered and evaporated to dryness. The crude product was purified by column chromatography (silica gel, DCM/MeOH=8:1) to obtain the product as black solid (11 mg, 22%).

Mp: 151-155° C.

$^1$H NMR (700 MHz, $CDCl_3$): δ=0.90 (t, J=7.2 Hz, 2H, $CH_2$), 2.33-2.37 (m, 2H, $CH_2$), 2.64 (s, 1H, NH), 4.65 (t, J=6.7 Hz, 2H, $CH_2$), 5.54 (br s, 1H, NH), 6.28 (dd, J=4.4, 1.4 Hz, 2H, $H_{pyrrole}$), 6.33-6.35 (m, 2H, $H_{pyrrole}$) 6.44 (dd, J=4.2, 1.7 Hz, 2H, $H_{pyrrole}$), 6.55 (d, J=4.0 Hz, 2H, $H_{pyrrole}$) 6.67 (d, J=4.3 Hz, 2H, $H_{pyrrole}$), 6.86 (d, J=4.3 Hz, 2H, $H_{pyrrole}$), 7.28-7.32 (m, 4H, $H_{bipyr}$), 7.69 (d, J=5.4 Hz, 2H, $H_{bipyr}$), 7.86-7.89 (m, 2H, $H_{bipyr}$), 7.91-7.94 (m, 2H, $H_{bipyr}$), 7.98 (s, 1H, $H_{triazol}$), 8.00 (d, J=5.6 Hz, 2H, $H_{bipyr}$) 8.43-8.47 (m, 4H, $H_{bipyr}$) ppm.

$^{19}$F NMR (376 MHz, $CDCl_3$): δ=-159.96 ($m_c$, J=15.0 Hz, 2F, Ar—$F_{meta}$), -153.94 ($m_c$, J=19.8, 5.7 Hz, 2F, Ar—$F_{meta}$), -144.77 ($m_c$, J=28.3 Hz, 2F, $BF_2$), -142.77 ($m_c$, J=14.9 Hz, 2F, Ar—$F_{ortho}$), -138.30 ($m_c$, J=13.9 Hz, 2F, Ar—$F_{ortho}$) ppm.

HRMS (ESI-TOF): m/z calc. for $C_{56}H_{38}BF_{10}N_{12}ORu$ [M]$^+$ 1197.2268, found 1197.2311.

UV/VIS (DCM): $\lambda_{max}$/nm [log($\varepsilon$/L mol$^{-1}$ cm$^{-1}$)]=470 (4.93), 517 (5.01) nm.

Fluorescence: $\lambda_{max}$=535 nm at $\lambda_{Exc}$=400 nm.

Reaction of [Bis(2,2'-bipyridyl)-(4-N-azidopropylamino)-2,3,5,6-tetrafluorophenyl)dipyrrinato)]ruthenium(II) chloride and 2-propynyl-tetra-O-acetyl-β-D-gluco-pyranoside

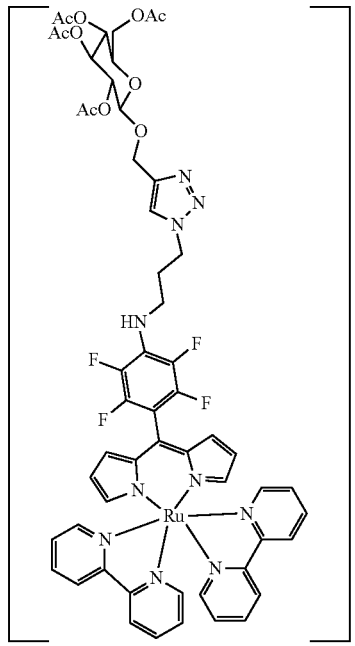

Under argon atmosphere and the exclusion of light [bis(2,2'-bipyridyl)-(4-N-azidopropylamino)-2,3,5,6-tetrafluorophenyl)dipyrrinato)]ruthenium(II) chloride (49 mg, 58 µmol) was dissolved in dry DMSO (5 mL), NaAsc (69 mg, 348 µmol, 6 eq), CuSO$_4$ 5H$_2$O (7 mg, 29 µmol, 50 mol %) and glucosyl alkyne (44 mg, 116 µmol, 2 eq) were added and the mixture stirred for 3 days at rt. Further purification was achieved by column chromatography (silica gel, DCM/MeOH=85:15) to obtain the product as black solid (28 mg, 41%).

Mp: 135-138° C.

$^1$H NMR (400 MHz, CDCl$_3$): δ=1.96-2.00 (m, 9H, OAc), 2.06 (s, 3H, OAc), 2.26-2.31 (m, 2H, CH$_2$), 3.45-3.56 (m, 2H, CH$_2$), 3.72-3.78 (m, 2H, CH$_2$), 4.16 (dd, J=12.4, 2.3 Hz, 2H, CH$_2$), 4.25 (dd, J=12.4, 4.6 Hz, 1H, H$_{glucose}$), 4.58 (t, J=6.7 Hz, 2H, CH$_2$), 4.69 (d, J=8.0 Hz, 1H, H$_{glucose}$), 4.83 (s, 1H, CH), 4.97-5.01 (m, 1H, H$_{glucose}$), 5.05-5.11 (m, 1H, H$_{glucose}$), 5.15-5.21 (m, 1H, H$_{glucose}$), 6.25 (dd, J=4.4, 1.3 Hz, 2H, H$_{pyrrole}$), 6.31-6.33 (m, 2H, H$_{pyrrole}$), 6.64 (d, J=4.4 Hz, 2H, H$_{pyrrole}$), 7.20-7.30 (m, 4H, H$_{bipyr}$), 7.65 (d, J=5.2 Hz, 2H, H$_{bipyr}$), 7.84-7.90 (m, 2H, H$_{bipyr}$), 7.92-7.98 (m, 4H, H$_{bipyr}$), 8.58-8.66 (m, 4H, H$_{bipyr}$) ppm.

$^{13}$C NMR (126 MHz, CDCl$_3$): δ=20.68 (OCH$_3$), 20.78 (OCH$_3$), 31.36 (CH$_2$), 41.09 (CH$_2$), 47.62 (CH$_2$), 61.90 (CH$_2$), 63.02 (C$_{glucose}$), 68.41 (C$_{glucose}$), 71.32 (C$_{glucose}$), 71.96 (C$_{gluocose}$), 72.88 (C$_{glucose}$), 99.91 (C$_{glucose}$), 119.10 (C$_{pyrrole}$), 123.64 (C$_{bipyr}$), 124.04 (C$_{bipyr}$), 124.07 (C$_{bipyr}$), 126.35 (C$_{bipyr}$), 126.75 (C$_{bipyr}$), 130.44 (C$_{pyrrole}$), 135.55 (C$_{bipyr}$), 135.92 (C$_{meso}$), 136.62 (C$_{bipyr}$), 150.01 (C$_{pyrrole}$), 150.64 (C$_{bipyr}$), 152.03 (C$_{bipyr}$), 157.31, (C$_{bipyr}$), 158.18 (C$_{bipyr}$), 169.56 (CO), 170.24 (CO), 170.80 (CO) ppm.

$^{19}$F NMR (376 MHz, CDCl$_3$): δ=-159.94 (m$_c$, J=17.5 Hz, 6F, Ar—F$_{meta}$), 143.06 (m$_c$, J$_{C-F}$=16.9 Hz, 6F, Ar—F$_{ortho}$) ppm.

HRMS (ESI-TOF): m/z calc. for $C_{55}H_{51}F_4N_{10}O_{10}Ru^+$ [M]$^+$ 1189.2775; found 1189.2776.

UV/VIS (DCM): $\lambda_{max}$/nm [log($\varepsilon$/L mol$^{-1}$ cm$^{-1}$)]=469 (4.39), 517 (3.69).

Synthesis of a Glycosylated Ruthenium Complex

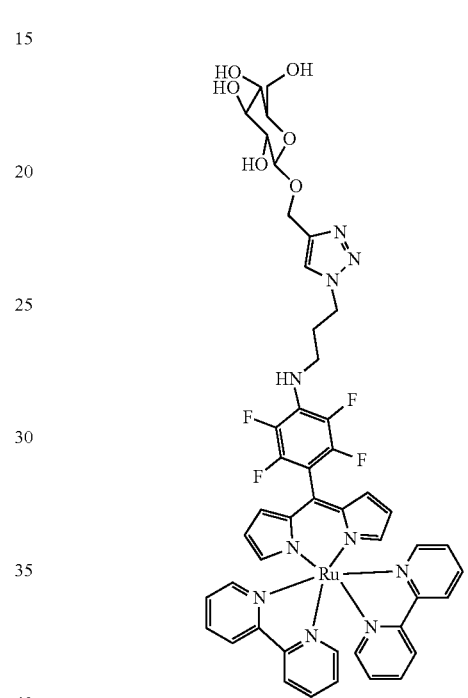

The complex from the previous reaction (100 mg, 84 µmol) was dissolved in MeOH (5 mL), sodium methoxide in MeOH (0.05 M, 5.25 mL, 0.42 mmol) was added and stirred for 1 h at rt. The mixture was evaporated to dryness and purified by column chromatography (silica gel, DCM/MeOH=85:15) to obtain the product as black solid (49 mg, 57%).

Mp: 185-187° C.

$^1$H NMR (400 MHz, (CD$_3$OD): δ=2.98 (s, 10H, CH$_2$), 4.60-4.65 (m, 4H, OH), 6.28 (dd, J=4.4, 1.4 Hz, 2H, H$_{pyrrole}$), 6.39-6.41 (m, 2H, H$_{pyrrole}$), 6.62 (d, J=4.3 Hz, 2H, H$_{pyrrole}$), 7.31-7.39 (m, 4H, H$_{bipyr}$), 7.81 (d, J=5.5 Hz, 2H, H$_{bipyr}$), 7.91-8.02 (m, 6H, H$_{bipyr}$), 8.53-8.59 (m, 4H, H$_{bipyr}$) ppm.

$^{13}$C NMR (126 MHz, (CD$_3$OD): δ=35.74 (CH$_2$), 61.75 (C$_{glucose}$), 73.73 (C$_{glucose}$), 73.73 (C$_{glucose}$), 76.64 (C$_{glucose}$), 76.72 (C$_{glucose}$), 118.79 (C$_{pyrrole}$), 123.33 (C$_{bipyr}$), 123.39 (C$_{bipyr}$), 126.15 (C$_{bipyr}$), 126.53 (C$_{bipyr}$), 129.91 (C$_{pyrrole}$), 135.61 (C$_{bipyr}$), 135.73 (C$_{bipyr}$), 136.25 (C$_{bipyr}$), 144.50 (C$_{meso}$), 149.82 (C$_{pyrrole}$), 150.90 (C$_{bipyr}$), 151.91 (C$_{bipyr}$), 157.52 (C$_{bipyr}$), 158.37 (C$_{bipyr}$), 163.62 (C$_{bipyr}$) ppm.

$^{19}$F NMR (376 MHz, (CD$_3$OD): δ=-162.38 (m$_c$, J=15.2 Hz, 2F, Ar—F$_{meta}$), -145.90 (m$_c$, J=15.1 Hz, 2F, Ar—F$_{ortho}$) ppm.

HRMS (ESI-TOF): m/z calc. for $C_{47}H_{43}F_4N_{10}O_6Ru^+$ [M]$^+$ 1021.2352, found 1021.2342.

UV/VIS (MeOH): $\lambda_{max}$/nm [log($\varepsilon$/L mol$^{-1}$ cm$^{-1}$)]=467 (4.80), 504 (4.29) nm.

[Bis(2,2'-bipyridyl(4-N-2-hydroxythylamino)-2,3,5,6-tetrafluorophenyl)dipyrrinato)]ruthenium(II) chloride

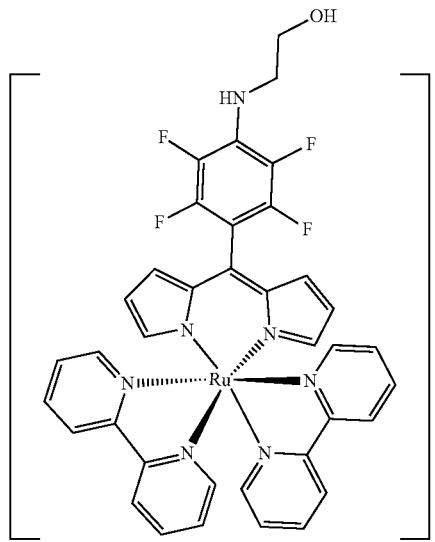

Under argon atmosphere [bis(2,2'-bipyridyl)-(5-pentafluorophenyl)dipyrrinato)]ruthenium(II) chloride (100 mg, 0.13 mmol) was dissolved in dry DMSO (3 mL), ethanolamine (160 mg, 0.16 mL, 2.63 mmol, 20 eq) was added and the mixture stirred for 48 h at 80° C. The mixture was diluted with DCM and washed with water several times. The organic layer was dried with sodium sulfate, filtered and evaporated to dryness. The crude product was purified by column chromatography to obtain the product as black solid (10 mg, 10%).

Mp=>300° C.

$^1$H NMR (400 MHz, CD$_3$OD): $\delta$=3.55 (t, J=5.8 Hz, 2H, CH$_2$), 3.74 (t, J=5.8 Hz, 2H, CH$_2$), 6.27 (dd, J=4.4, 1.3 Hz, 2H, H$_{pyrrole}$), 6.35-6.37 (m, 2H, H$_{pyrrole}$), 6.64 (dd, J=4.2 Hz, 2H, H$_{pyrrole}$), 7.30-7.35 (m, 2H, H$_{bipyr}$), 7.36-7.41 (m, 2H, H$_{bipyr}$), 7.78 (d, J=5.0 Hz, 2H, H$_{bipyr}$), 7.90-7.98 (m, 4H, H$_{bipyr}$), 8.03 (d, J=6.0 Hz, 2H, H$_{bipyr}$), 8.48-8.52 (m, 4H, H$_{bipyr}$) ppm.

$^{13}$C NMR (126 MHz, CD$_3$OD): $\delta$=47.45 (CH$_2$), 61.14 (CH$_2$), 118.93 (C$_{pyrrole}$), 126.46 (C$_{bipyr}$), 126.63 (C$_{bipyr}$), 130.39 (C$_{pyrrole}$), 135.67 (C$_{bipyr}$), 135.78 (C$_{bipyr}$), 136.31 (C$_{meso}$), 149.82 (C$_{pyrrole}$), 150.84 (C$_{bipyr}$), 152.21 (C$_{bipyr}$), 158.34 (C$_{bipyr}$) ppm.

$^{19}$F NMR (376 MHz, CD$_3$OD): $\delta$=−161.82 (m$_c$, J=14.5 Hz, 2F, Ar—F$_{meta}$), −145.50--145.25 (m, 2F, Ar—F$_{ortho}$) ppm.

HRMS (ESI-TOF): m/z calc. for C$_{37}$H$_{28}$F$_4$N$_7$ORu [M]+ 764.1335, found 764.1341.

UV/VIS (MeOH): $\lambda_{max}$/nm [log($\varepsilon$/L mol$^{-1}$ cm$^{-1}$)]=467 (5.03), 504 (4.50) nm.

[Bis(2,2'-bipyridyl)-(1-thio-β-D-glucosyl)-2,3,5,6-tetrafluorophenyl)dipyrrinato)]ruthenium(II) chloride

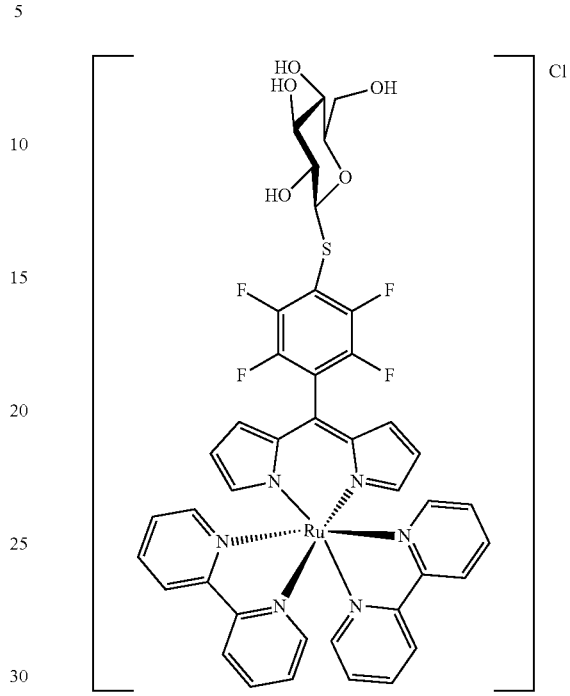

Under argon atmosphere and the exclusion of light [bis(2,2'-bipyridyl)-(5-pentafluorophenyl)dipyrrinato)]ruthenium (II) chloride (100 mg, 0.13 mmol) was dissolved in dry DMF (3 mL), 1-thio-β-D-glucose sodium salt hydrate (37 mg, 0.17 mmol, 1.3 eq) was added and the mixture stirred for 10 min at rt. The mixture was evaporated to dryness and purified by column chromatography (DCM/MeOH=85:15) to obtain the product as black solid (60 mg, 50%).

Mp: 220-223° C.

$^1$H NMR (400 MHz, CD$_3$OD): $\delta$=3.32-3.38 (m, 2H, CH$_{glucose}$), 3.40-3.46 (m, 1H, CH$_{glucose}$), 3.58-3.63 (m, 1H, CH$_{glucose}$), 4.90-4.96 (m, 2H, CH$_2$), 6.31 (dd, J=4.5, 1.3 Hz, 2H, H$_{pyrrole}$), 6.44-6.45 (m, 2H, H$_{pyrrole}$), 6.63 (d, J=4.4 Hz, 2H, H$_{pyrrole}$), 7.33-7.38 (m, 4H, H$_{bipyr}$), 7.83 (d, J=5.0 Hz, 2H, H$_{bipyr}$), 7.90-8.05 (m, 6H, H$_{bipyr}$), 8.58 (t, J=8.2 Hz, 4H, H$_{bipyr}$) ppm.

$^{13}$C NMR (126 MHz, CD$_3$OD): $\delta$=61.46 (C$_{glucose}$), 70.16 (C$_{glucose}$), 74.44 (C$_{glucose}$), 78.25 (C$_{glucose}$), 81.13 (C$_{glucose}$), 81.15 (C$_{glucose}$), 85.50 (CH$_2$), 112.46 (t, J$_{C-F}$=20.6 Hz, Ar—C$_{ipso}$), 119.31 (C$_{pyrrole}$), 126.20 (C$_{bipyr}$), 126.62 (C$_{bipyr}$), 129.75 (C$_{pyrrole}$), 134.37 (C$_{meso}$), 135.86 (C$_{bipyr}$), 136.40 (C$_{bipyr}$), 144.39 (dd, J$_{C-F}$=247.3, 15.8 Hz, Ar—C$_{meta}$), 146.91 (dd, J$_{C-F}$=247.0, 15.6 Hz, Ar—C$_{ortho}$), 150.44 (C$_{pyrrole}$), 150.94 (C$_{bipyr}$), 151.87 (C$_{bipyr}$), 157.54 (C$_{bipyr}$), 158.33 (C$_{bipyr}$) ppm.

$^{19}$F NMR (376 MHz, CD$_3$OD): $\delta$=−142.96 (m$_c$, J=24.3, 11.3 Hz, 2F, Ar—F$_{meta}$), −134.40--134.22 (m, 2F, Ar—F$_{ortho}$) ppm.

HRMS (ESI-TOF): m/z calc. for C$_{41}$H$_{33}$F$_4$N$_6$O$_5$RuS$^+$ [M]$^+$ 899.1213, found 899.1230.

UV/VIS (MeOH): $\lambda_{max}$/nm [log($\varepsilon$/L mol$^{-1}$ cm$^{-1}$)]=440 (4.56), 468 (4.90) nm.

Example 4

Cell Tests of Selected Compounds in the HT 29 and Other Cell Lines

The photosensitizing activity was determined in the following cell lines:
HT29 (human colon adenocarcinoma cell line)
L929 (mouse fibroblast cell line)
A431 (human epidermoid carcinoma cell line)
A253 (submaxillary salivary gland, epidermoid cell line)
CAL-27 (human tongue squamous cell carcinoma cell line)
J774A.1 (Mouse BALB/c monocyte macrophage).

The cell lines were grown in DMEM (PAA Laboratories GmbH) supplemented with 10% heat-inactivated fetal calf serum (FCS, PAA Laboratories GmbH), 1% penicillin (10000 IU) and streptomycin (10000 μg/ml, PAA Laboratories GmbH). Cells were kept as a monolayer culture in a humidified incubator (5% $CO_2$ in air at 37° C.). A photosensitizer stock solution (2 mM) was performed in DMSO and was kept in the dark at 4° C. Further dilution was performed in DMEM medium without phenol red supplemented with 10% FCS to reach a final photosensitizer concentration of 2 or 10 μM, respectively. $2 \cdot 10^4$ cells/ml were seeded in micro plates ($2 \cdot 10^5$ cells/well). Cells were incubated with fresh medium (DMEM without phenol red) containing 10% FCS with 2 or 10 μM of the photosensitizer for 24 h before light exposure. Before photosensitization, cells were washed, cell culture medium was exchanged with DMEM without phenol red and 10% FCS, then irradiated at room temperature with white light source at a fixed fluence rate of about 100 mW/cm$^2$ (50 J/cm$^2$). Following irradiation, cells were incubated in a humidified incubator (5% $CO_2$ in air at 37° C.) for 24 h until cell viability assay. The cell viability was assessed by the XTT assay. 500 mg XTT (sodium 3'-[phenylaminocarbonyl]-3,4-tetrazolium]-bis(4-methoxy-6-nitro)benzene sulfonic acid, Applichem GmbH) is dissolved in 500 ml PBS-Buffer (without $Ca^{2+}$ and $Mg^2$) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS was dissolved in 1 ml PBS-Buffer. The solution should be stored frozen and should not be exposed to light. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with RPMI without phenol red and 10% FCS (100 μl) prior adding 50 μl XTT reaction solution per well. The micro plate was incubated for 2-3 hours at 37° C. and 5% $CO_2$ until an orange dye was formed. The micro plate has been shaken gently to evenly distribute the dye in the wells. The absorbance of the samples was measured with a spectrophotometer (Infinite 200, Tecan Group Ltd.) at a wavelength of 490 nm.

Figure 6:
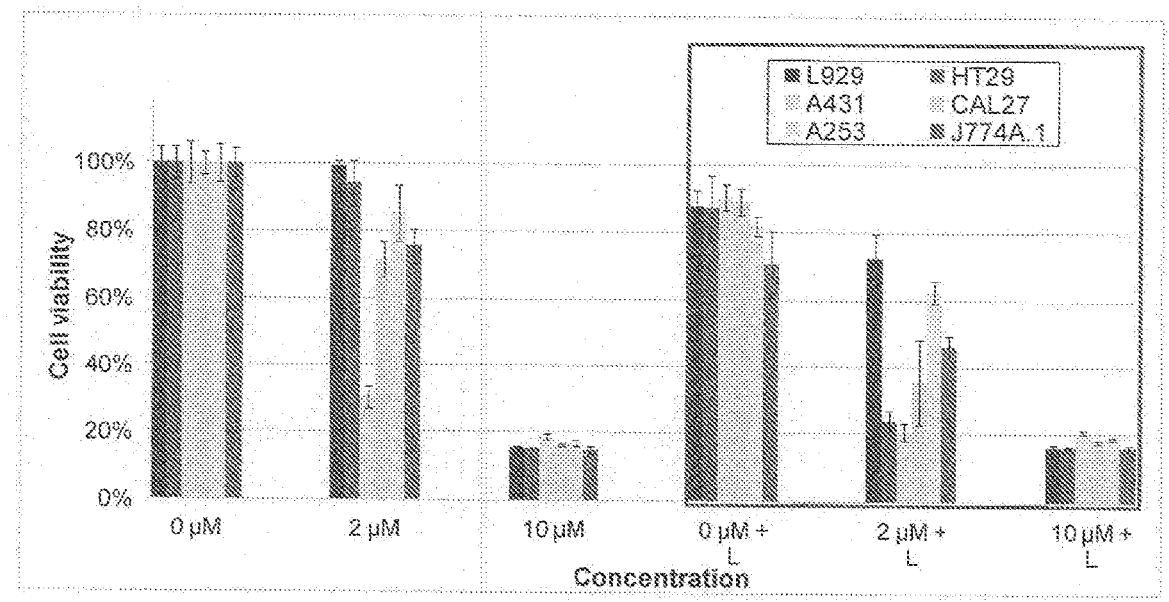
FIG. 6 illustrates the photodynamic activity ('+L' means phototoxicity) and the light independent antitumor activity of [bis(2,2'-bipyridyl(4-(hexyloxy)-2,3,5,6-tetrafluorophenyl)¬dipyrrinato)]-ruthenium(II) chloride.
Figure 7:
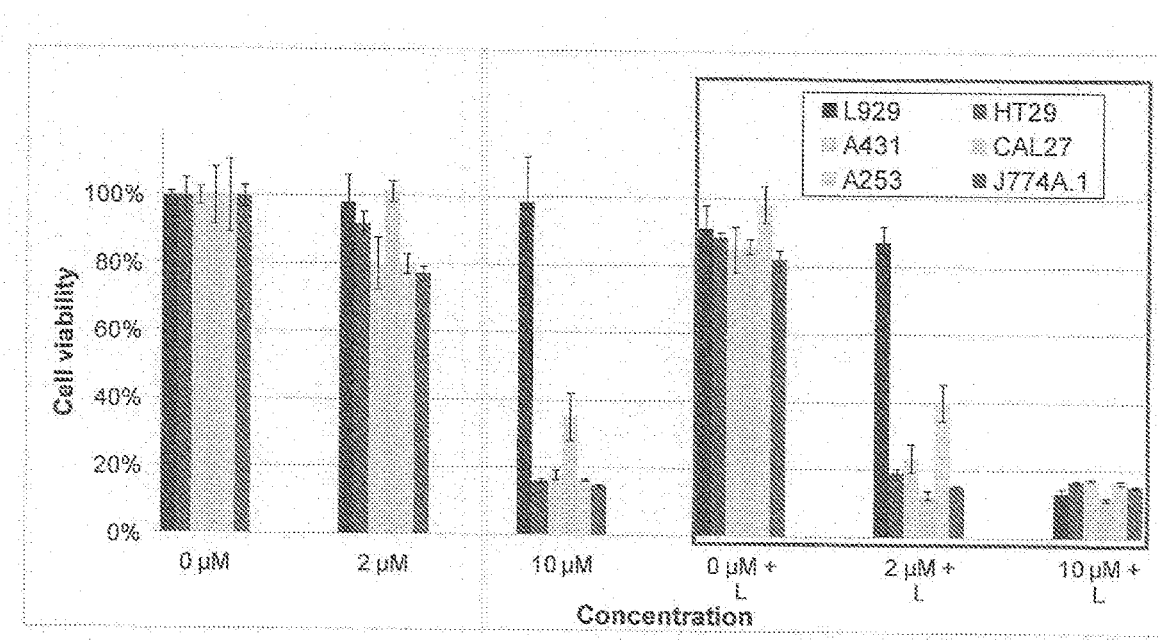
FIG. 7 illustrates the photodynamic activity ('+L' means phototoxicity) and the light independent antitumor activity of [bis(2,2'-bipyridyl(4-(prop-2-enylamino)-2,3,5,6-tetrafluorophenyl)¬dipyrrinato)]-ruthenium(II) chloride
Figure 8:
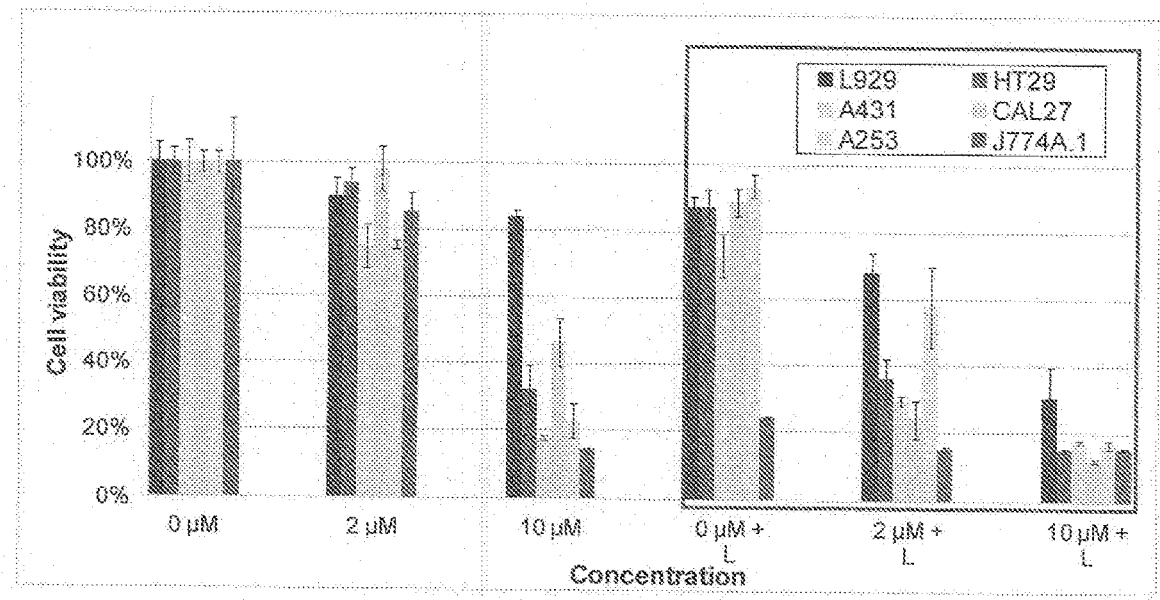
FIG. 8 illustrates the photodynamic activity ('+L' means phototoxicity) and the light independent antitumor activity of [bis(2,2'-bipyridyl(4-(prop-2-enyloxy)-2,3,5,6-tetrafluorophenyl)¬dipyrrinato)]-ruthenium(II) chloride.
Figure 9A:
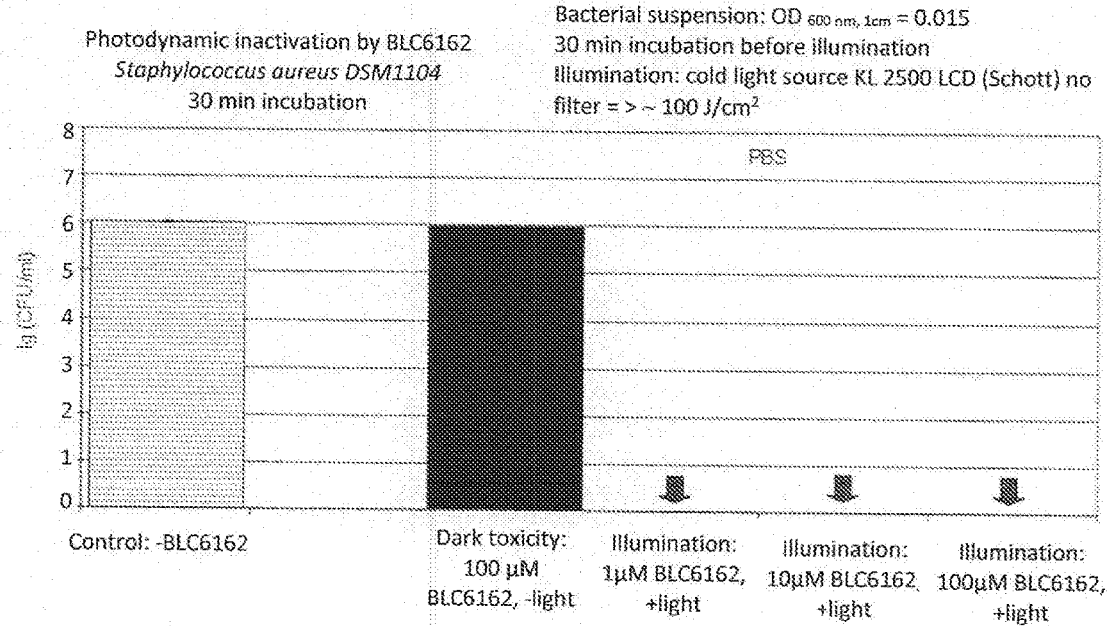
FIGS. 9A, 9B and 9C illustrate the photodynamic activity ('+light' means phototoxicity) and the light independent antibacterial activity of tris[5-(4-β-D-thioglucosyl)-2,3,5,6-tetrafluoro¬phenyl)¬dipyrrinato gallium(III)
Figure 9B:
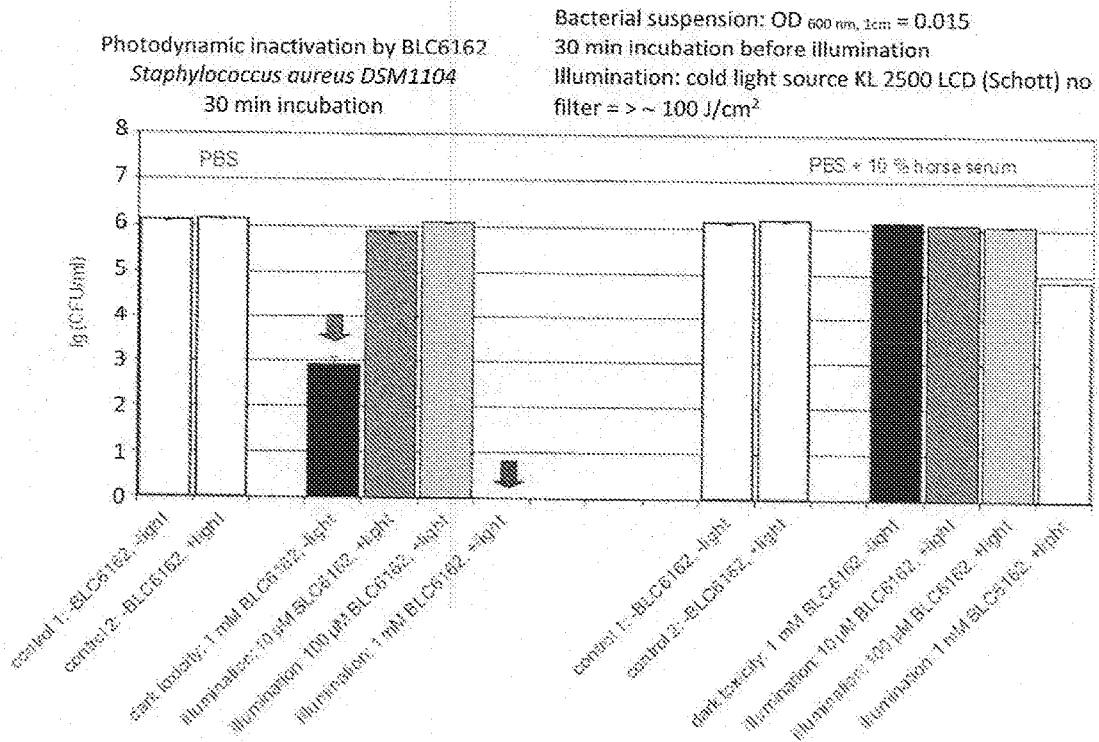
Figure 9C:
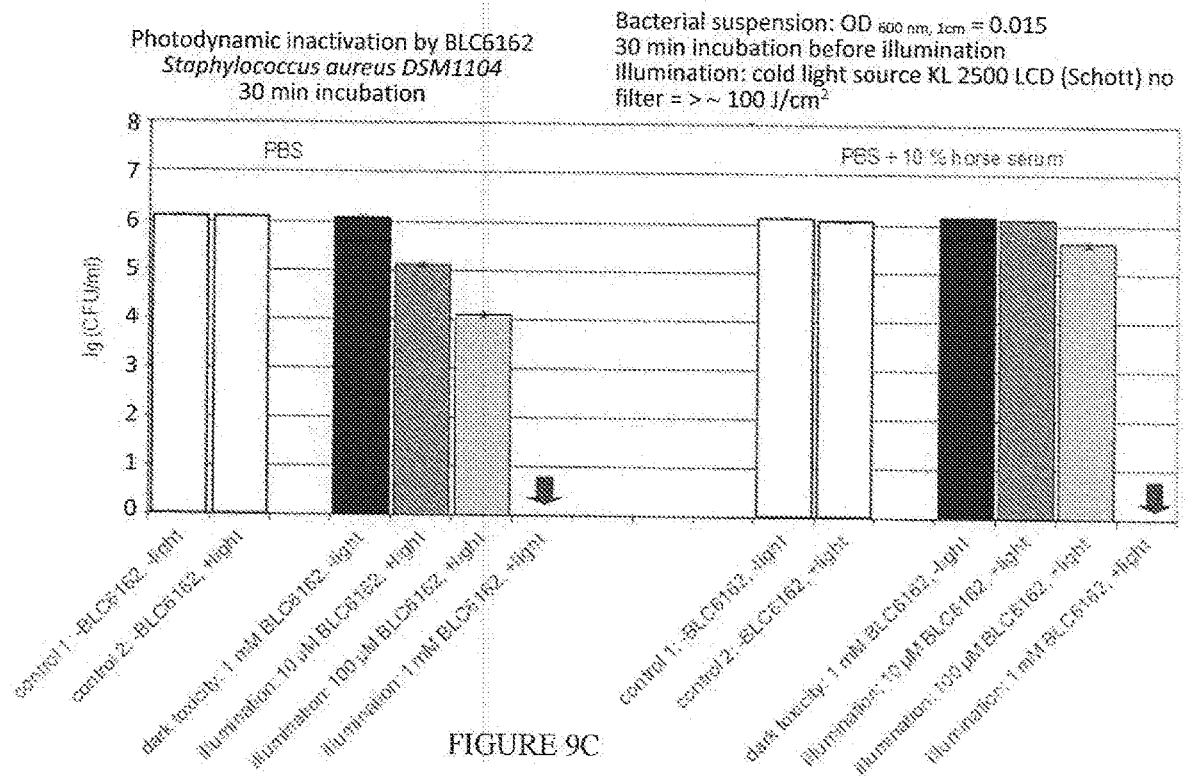

The examples 4.1 to 4.8 illustrate in FIGS. 1 to 8 the photodynamic activity ('+L' means phototoxicity) and the light independent antitumor activity of selected compounds which are subject of the present invention. Compounds of examples 4.3 and 4.5 shown in FIGS. 3 and 5 exhibit a high activity against the cell lines under irradiation but no activity without light. Compounds of activity against the cell lines under irradiation but no activity without light. Compounds of examples 4.6, 4.7, and 4.8 on the other hand exhibit a high toxicity against tumor cells even in the absence of light, as shown in FIGS. 6, 7 and 8 respectively.

4.1 Cell Test of [bis(2,2'-bipyridyl(4-(prop-2-ynylamino)-2,3,5,6-tetrafluorophenyl)-dipyrrinato)]ruthenium(II) chloride

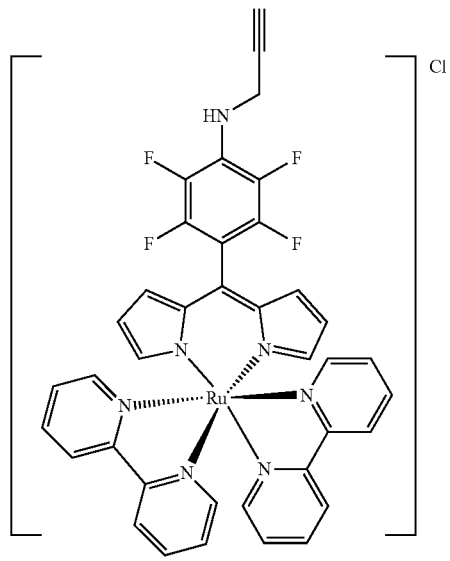

4.2 Cell Test of [bis(2,2'-bipyridyl(4-(prop-2-ynyloxy)-2,3,5,6-tetrafluorophenyl)-dipyrrinato)]ruthenium(II) chloride

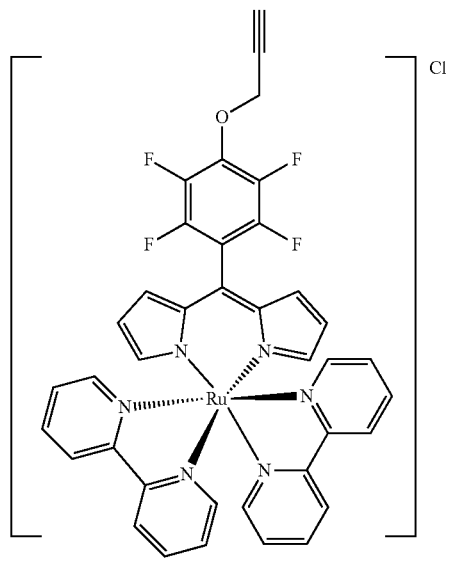

4.3 Cell Test of tris[5-(4-β-D-thioglucosyl)-2,3,5,6-tetrafluorophenyl)dipyrrinato galliumn(III)
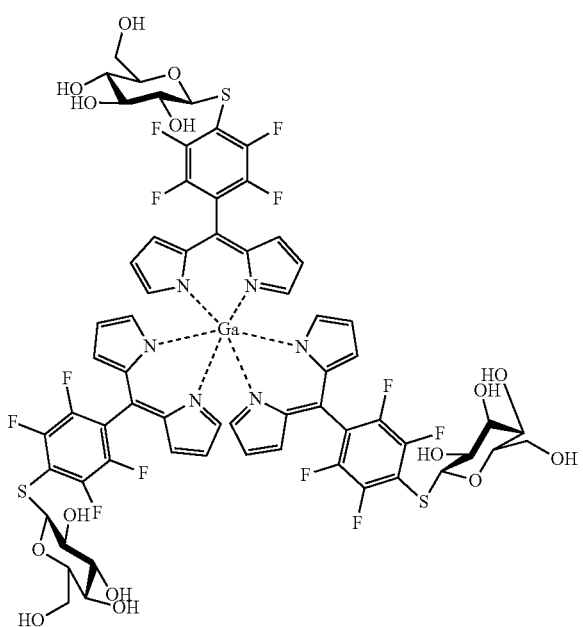
4.4 Cell Test of Ruthenium Complex-BODIPY Conjugate
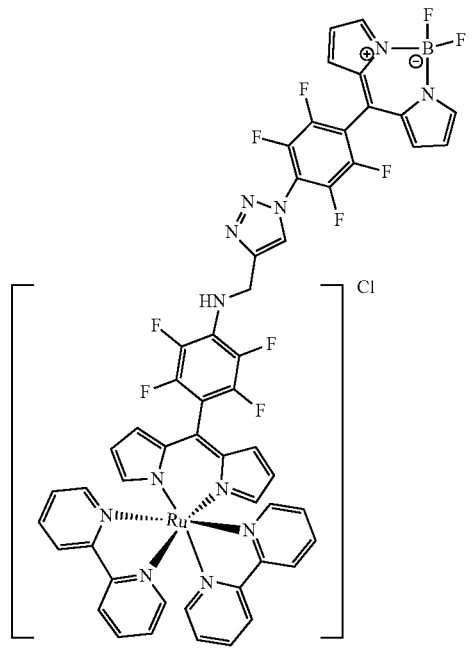
4.5 Cell Test tris[5-(4-β-D-thiogalactosyl)-2,3,5,6-tetrafluorophenyl)dipyrrinato gallium(III)
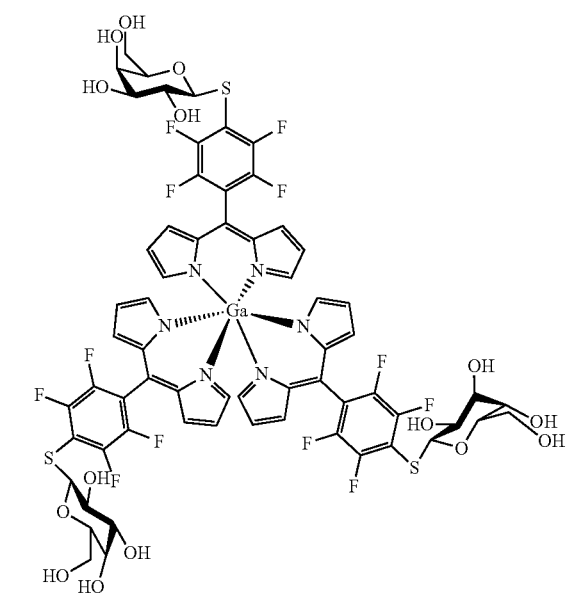
4.6 Cell Test of [bis(2,2'-bipyridyl(4-(hexyloxy)-2,3,5,6-tetrafluorophenyl)-dipyrrinato)]ruthenium(II) chloride
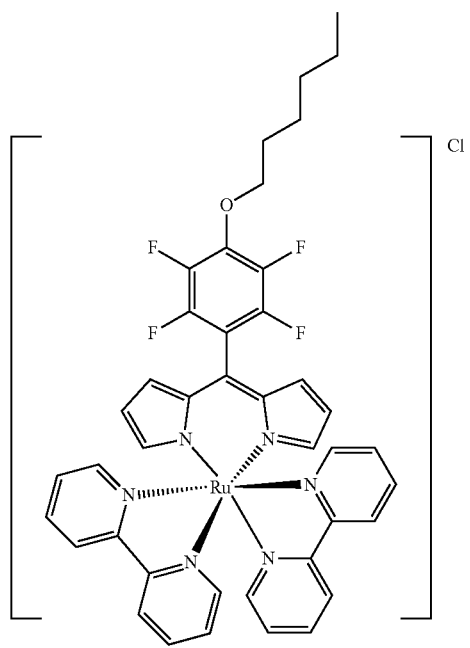

4.7 Cell test of [bis(2,2'-bipyridyl(4-(prop-2-enylamino)-2,3,5,6-tetrafluorophenyl)-dipyrrinato)]ruthenium(II) chloride

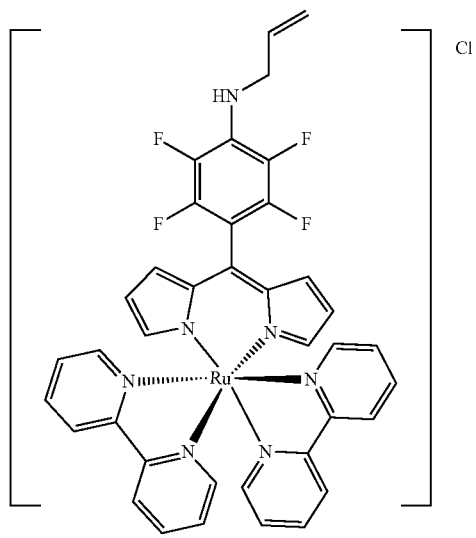

4.8 Cell test of [bis(2,2'-bipyridyl(4-(prop-2-enyloxy)-2,3,5,6-tetrafluorophenyl)-dipyrrinato)]ruthenium(II) chloride

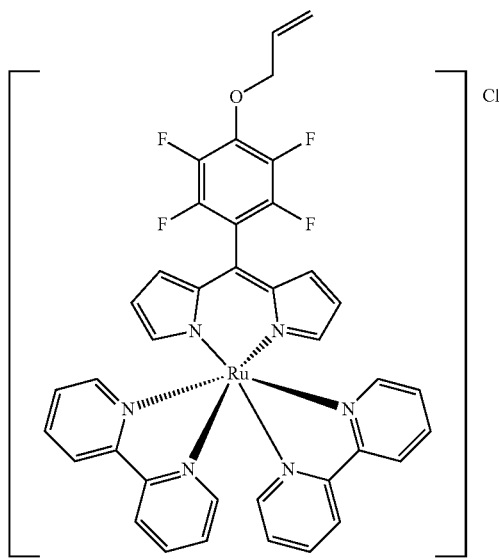

Example 5

Antibacterial Testing

The organisms studied were *Staphylococcus aureus* DSM 11729, Gram-positive; *Acinetobacter baumannii* DSM30007, and *Klebsiella pneumoniae* DSM30104, both Gram-negative.

Cultures cells are suspended in sterile phosphate-buffered saline (PBS) or sterile PBS supplemented with 10% sterile horse blood serum. The bacterial suspensions are placed into sterile black well plates with clear bottoms. Concentrations of photosensitizer used in the study were as follows: 100 µM, 10 µM and 1 µM. After an incubation time period of 30 minutes, the samples are exposed to white light, with a power density and irradiation time resulting in an energy fluency of about 100 J/cm$^2$. Control plates contained no photosensitizer and are not exposed to laser light. The control samples for dark toxicity are only exposed to photosensitizer without any illumination. After irradiation, the samples are removed and suspended again in the culture media. The numbers of colony-forming units (CFU/ml) are enumerated after an adequate incubation time period.

Figure 10:
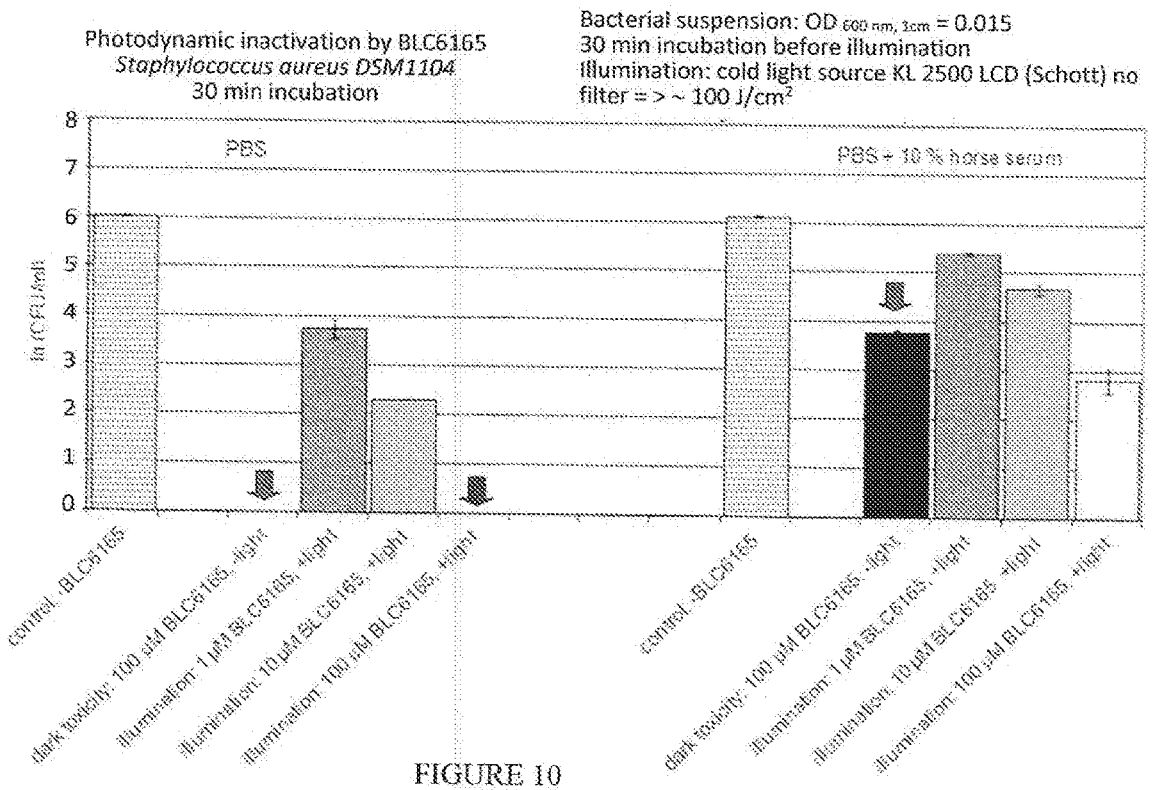
FIG. 10 illustrates the photodynamic activity ('+light' means phototoxicity) and the light independent antibacterial activity of complex-BODIPY conjugate.
Figure 11:
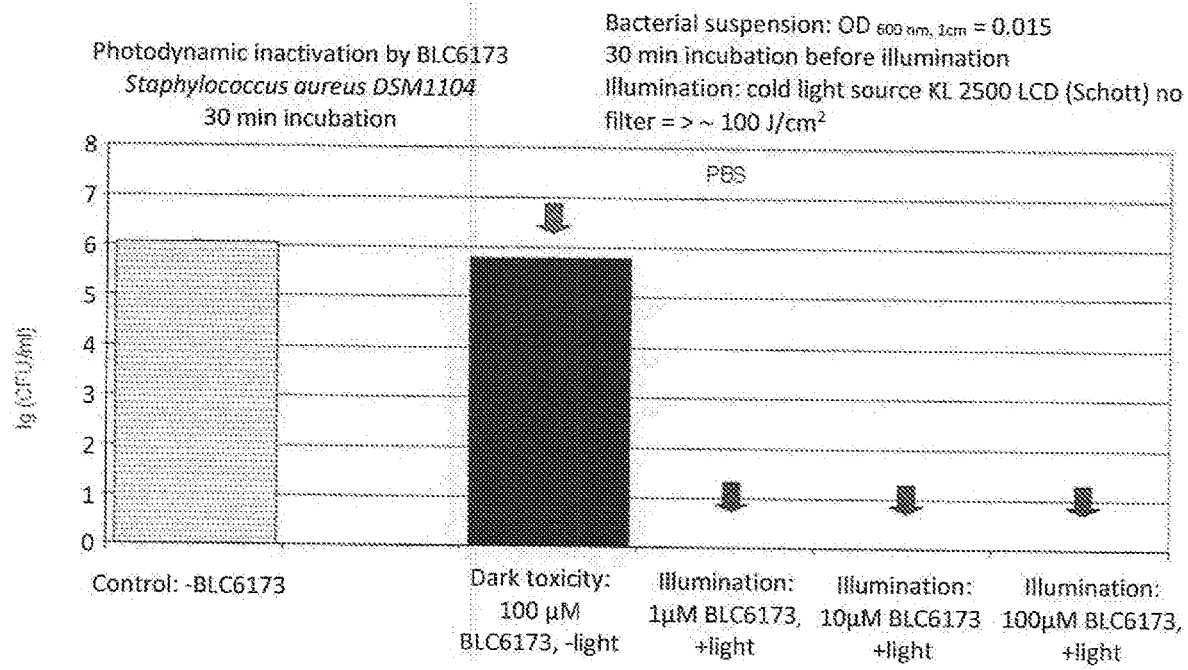
FIG. 11 illustrates the photodynamic activity ('+light' means phototoxicity) and the light independent antibacterial activity of tris[5-(4-β-D-thiogalactosyl)-2,3,5,6-tetrafluoro¬phenyl)¬dipyrrinato gallium(III).
Figure 12:
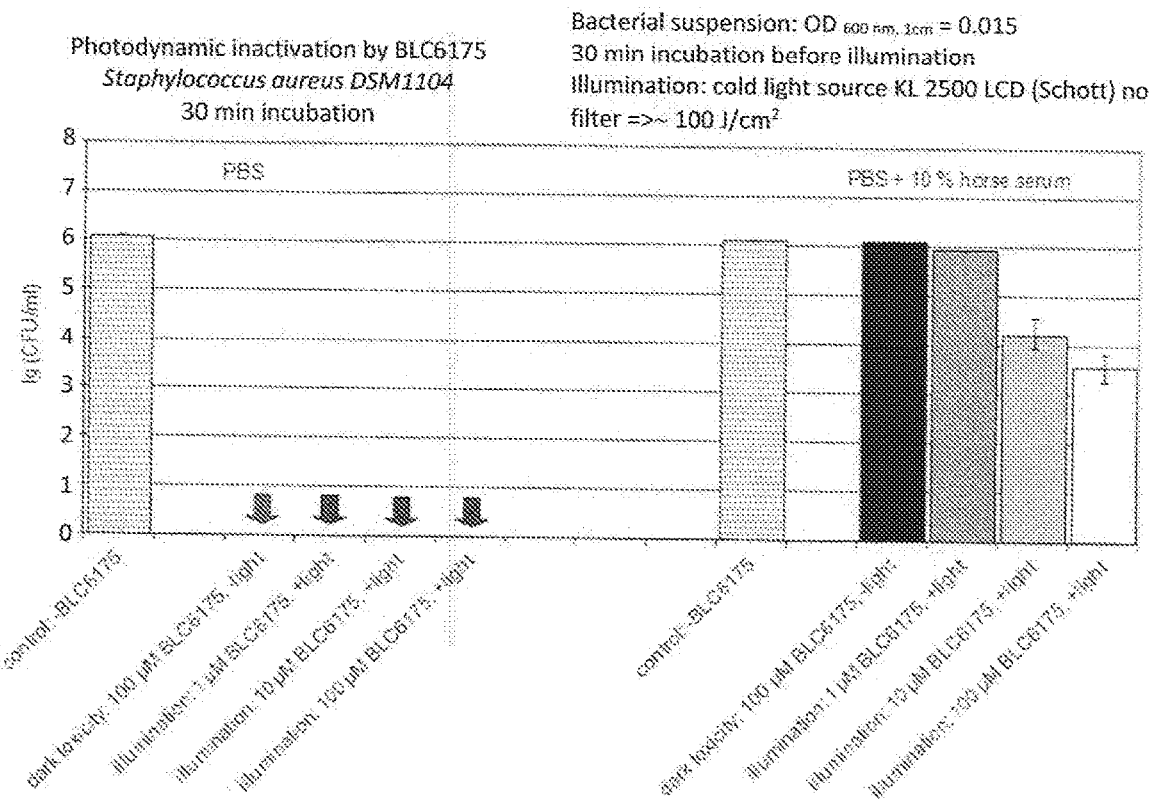
FIG. 12 illustrates the photodynamic activity ('+light' means phototoxicity) and the light independent antibacterial activity of [bis(2,2'-bipyridyl(4-(prop-2-enylamino)-2,3,5,6-tetrafluorophenyl)-dipyrrinato)]-ruthenium(II) chloride.
Figure 13:
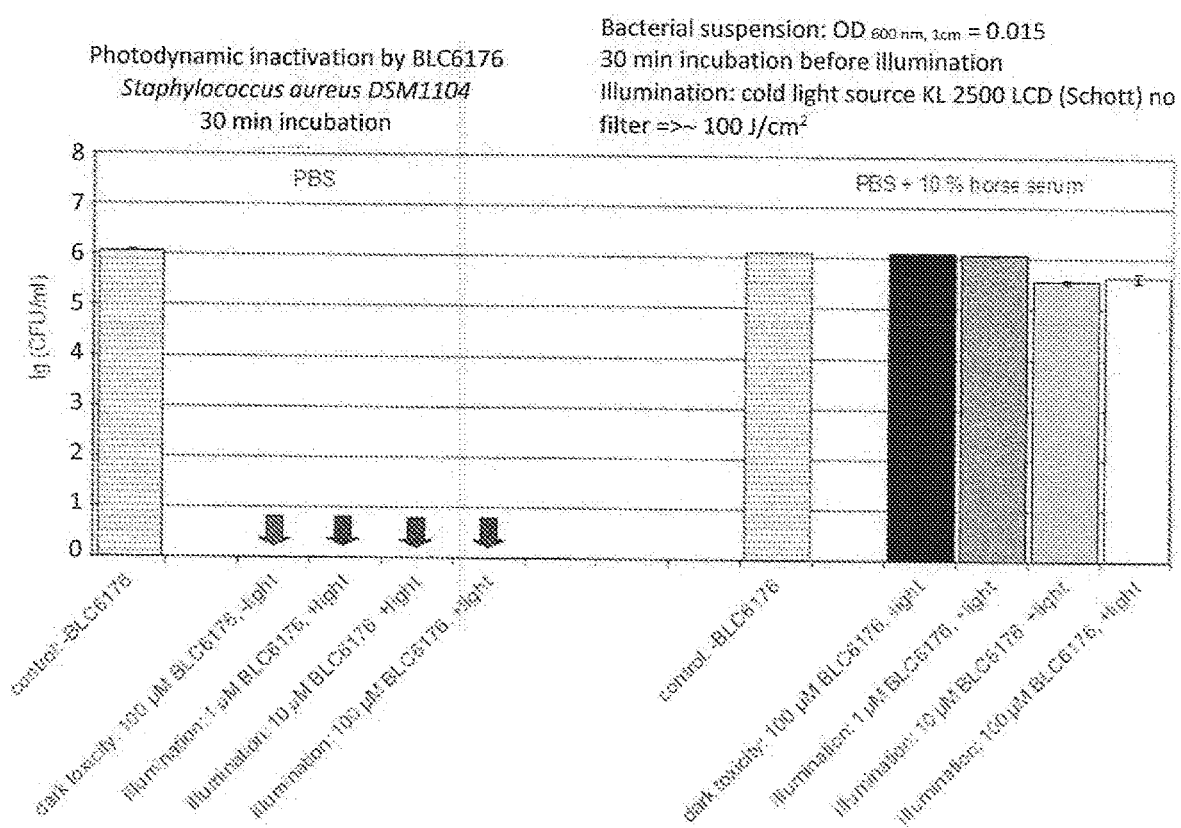
FIG. 13 illustrates the photodynamic activity ('+light' means phototoxicity) and the light independent antibacterial activity of [bis(2,2'-bipyridyl(4-(prop-2-enyloxy)-2,3,5,6-tetrafluorophenyl)¬dipyrrinato)]-ruthenium(II) chloride.

The examples 5.1 to 5.5 illustrate in FIGS. 9 to 13 the photodynamic activity ('+light' means phototoxicity) and the light independent antibacterial activity of selected compounds which are subject of the present invention. Compounds of examples 5.1 and 5.3 show a high activity against *S. aureus* (and *K. pneumoniae* for 5.1) under irradiation, however nearly no activity without light (FIGS. 9A-C and 11). Compounds of examples 5.2, 5.4, and 5.5 on the other hand exhibit a high toxicity against *S. aureus* even in the absence of light (FIGS. 10, 12 and 13). For examples 5.1, 5.2, and 5.4 antibacterial activity is also observed in the presence of complex media (serum addition) (FIGS. 9A-C, 10 and 12).

5.1. Antibacterial test of tris[5-(4-β-D-thioglucosyl)-2,3,5,6-tetrafluorophenyl)-dipyrrinato gallium (III)

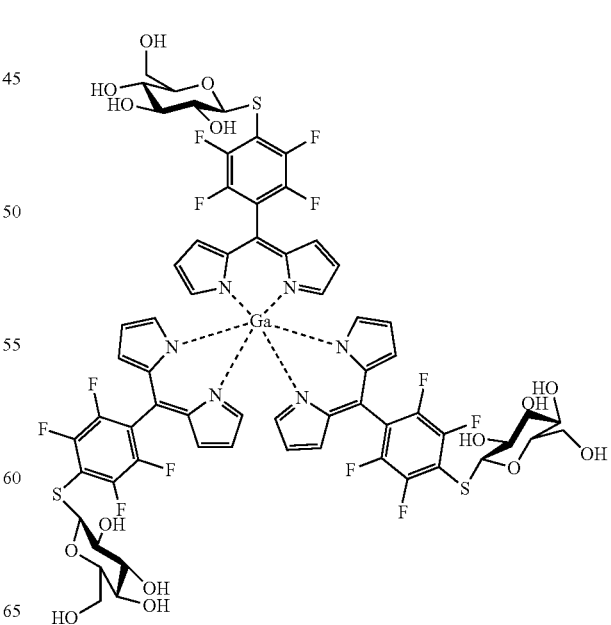

5.2 Antibacterial Test of Ruthenium Complex-BODIPY Conjugate

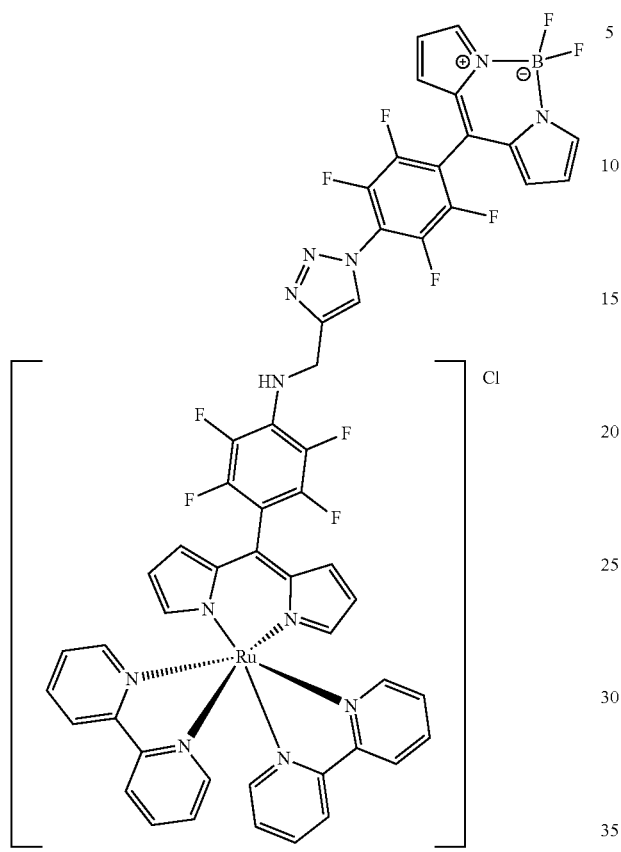

5.3 Antibacterial test of tris[5-(4-β-D-thiogalactosyl)-2,3,5,6-tetrafluorophenyl)-dipyrrinato gallium (III)

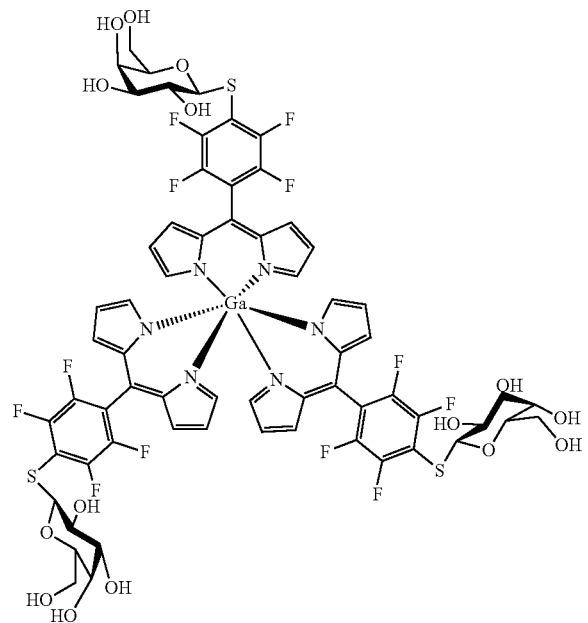

5.4 Antibacterial Test of [bis(2,2'-bipyridyl(4-(prop-2-enylamino)-2,3,5,6-tetrafluorophenyl)dipyrrinato)] ruthenium(II) chloride

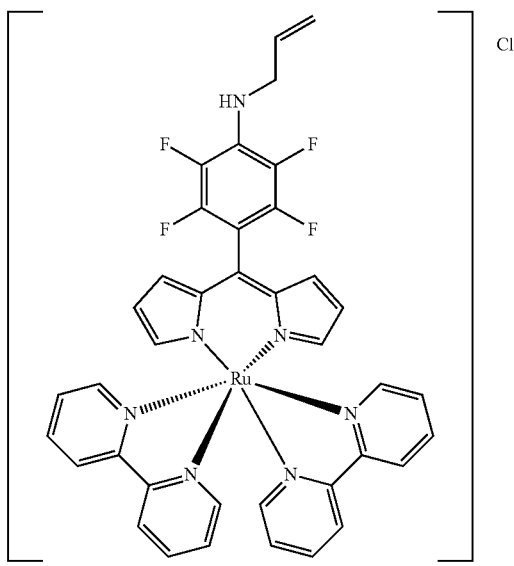

5.5 Antibacterial Test of [bis(2,2'-bipyridyl(4-(prop-2-enyloxy)-2,3,5,6-tetrafluorophenyl)dipyrrinato)] ruthenium(I) chloride

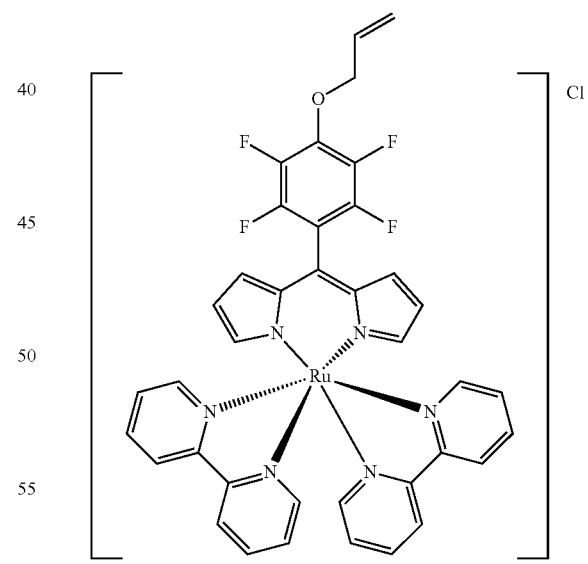

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

What is claimed is:

1. A metal complex of the formula 1 or 2:

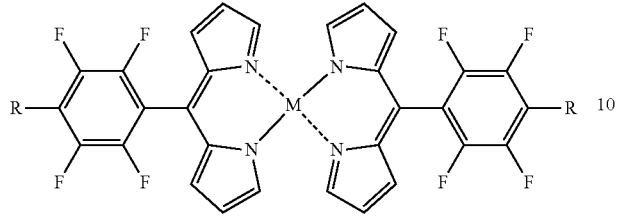

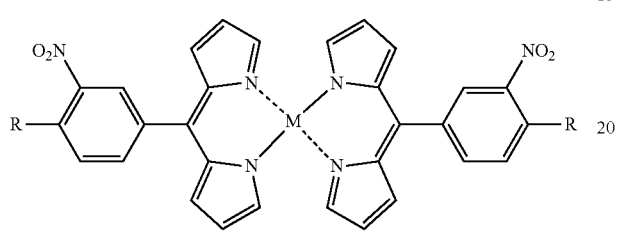

Wherein:
M(II) is a divalent metal ion selected from the group consisting of iron, cobalt, nickel, copper, platinum, and zinc;
R is selected from the group consisting of O—$R^1$, NH—$R^1$, N($R^1$)$_2$ and S—$R^1$ wherein $R^1$ is selected from the group consisting of:
 a short chain alkyl, alkenyl, or alkynyl group consisting of 1-15 carbon atoms;
 a short chain alkyl group consisting of 1-4 carbon atoms and carrying 1 to 4 hydroxyl groups;
 a carbohydrate moiety;

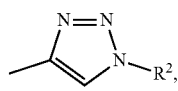

wherein $R^2$ is a carbohydrate moiety or a substituted borondipyrromethene moiety; and

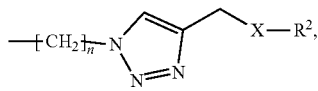

wherein n=1 to 5, X is O or NH and $R^2$ is a carbohydrate moiety or a substituted borondipyrromethene moiety.

2. The metal complex according to claim 1 or a pharmaceutically acceptable salt thereof when used in tumor therapy or photodynamic therapy.

3. The metal complex according to claim 1 or a pharmaceutically acceptable salt thereof when used in therapy or photodynamic therapy of tumors, dermatological disorders, viral or bacterial infections, ophthalmological disorders or urological disorders.

4. The metal complex according to claim 1 or a pharmaceutically acceptable salt thereof used for the preparation of a pharmaceutical composition for tumor therapy or photodynamic tumor therapy.

5. The metal complex according to claim 1 or a pharmaceutically acceptable salt thereof when used in the diagnosis, therapy or photodynamic therapy of arthritis and tumors.

6. A pharmaceutical composition comprising metal complex according to claim 1 or a pharmaceutically acceptable salt thereof as an active ingredient.

7. The pharmaceutical composition according to claim 6, further conjugated to a targeting agent, wherein the targeting agent is a peptide.

8. A metal complex of the formula 1 or 2:

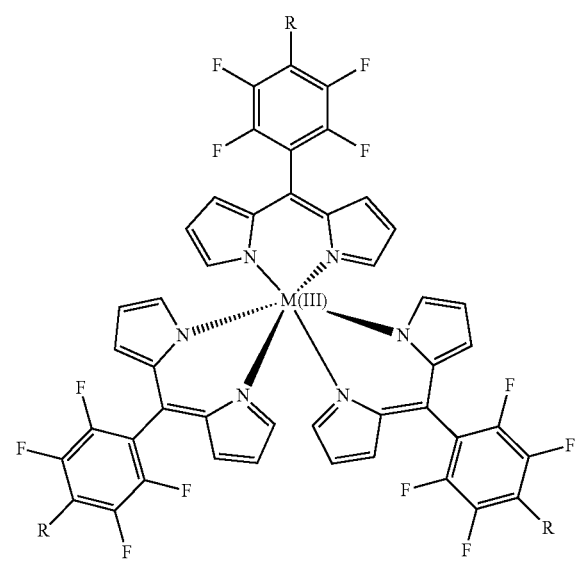

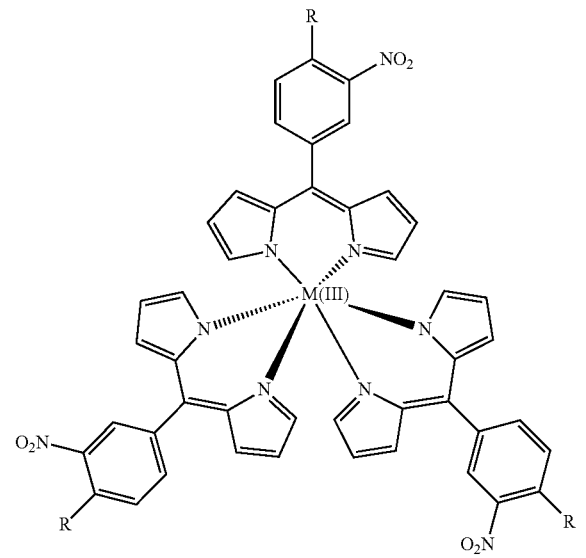

Wherein:
M(III) is a trivalent metal ion selected from the group consisting of iron, cobalt, ruthenium, rhodium, iridium, indium, and gallium;
R is selected from the group consisting of O—$R^1$, NH—$R^1$, N($R^1$)$_2$ and S—$R^1$ wherein $R^1$ is selected from the group consisting of:
 a short chain alkyl, alkenyl, or alkynyl group consisting of 1-15 carbon atoms;

a short chain alkyl group consisting of 1-4 carbon atoms and carrying 1 to 4 hydroxyl groups;
a carbohydrate moiety;

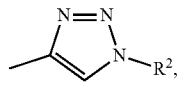

wherein R² is a carbohydrate moiety or a substituted borondipyrromethene moiety; and

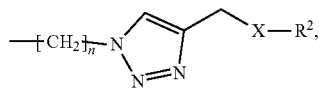

wherein n=1 to 5, X is O or NH and R² is a carbohydrate moiety or a substituted borondipyrromethene moiety.

9. The metal complex according to claim 8 or a pharmaceutically acceptable salt thereof when used in tumor therapy or photodynamic therapy.

10. The metal complex according to claim 8 or a pharmaceutically acceptable salt thereof when used in therapy or photodynamic therapy of tumors, dermatological disorders, viral or bacterial infections, ophthalmological disorders or urological disorders.

11. The metal complex according to claim 8 or a pharmaceutically acceptable salt thereof used for the preparation of a pharmaceutical composition for tumor therapy or photodynamic tumor therapy.

12. The metal complex according to claim 8 or a pharmaceutically acceptable salt thereof when used in the diagnosis, therapy or photodynamic therapy of arthritis and tumors.

13. A pharmaceutical composition comprising metal complex according to claim 8 or a pharmaceutically acceptable salt thereof as an active ingredient.

14. The pharmaceutical composition according to claim 13, further conjugated to a targeting agent, wherein the targeting agent is a peptide.

15. A metal complex of the formula 1 or 2:

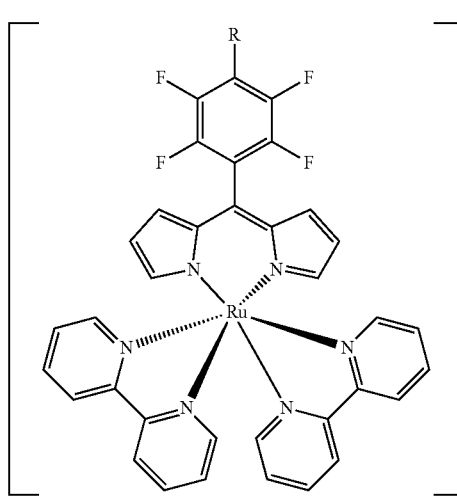

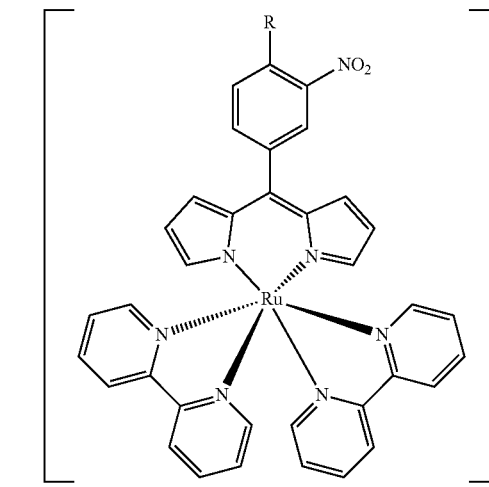

Wherein:
An⁻ is an acceptable counterion;
R is selected from the group consisting of O—R¹, NH—R¹, N(R¹)₂ and S—R¹ wherein R¹ is selected from the group consisting of:
a short chain alkyl, alkenyl, or alkynyl group consisting of 1-15 carbon atoms;
a short chain alkyl group consisting of 1-4 carbon atoms and carrying 1 to 4 hydroxyl groups;
a carbohydrate moiety;

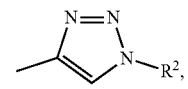

wherein R² is a carbohydrate moiety, a substituted borondipyrromethene moiety or a hydrophilic polymer; and

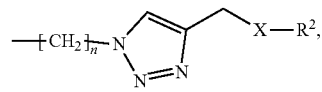

wherein n=1 to 5, X is O or NH and R² is a carbohydrate moiety, a substituted borondipyrromethene moiety or a hydrophilic polymer.

16. The metal complex according to claim 15 or a pharmaceutically acceptable salt thereof when used in tumor therapy or photodynamic therapy.

17. The metal complex according to claim 15 or a pharmaceutically acceptable salt thereof when used in therapy or photodynamic therapy of tumors, dermatological disorders, viral or bacterial infections, ophthalmological disorders or urological disorders.

18. The metal complex according to claim 15 or a pharmaceutically acceptable salt thereof used for the preparation of a pharmaceutical composition for tumor therapy or photodynamic tumor therapy.

19. The metal complex according to claim 15 or a pharmaceutically acceptable salt thereof when used in the diagnosis, therapy or photodynamic therapy of arthritis and tumors.

20. A pharmaceutical composition comprising metal complex according to claim 15 or a pharmaceutically acceptable salt thereof as an active ingredient.

21. The pharmaceutical composition according to claim 20, further conjugated to a targeting agent, wherein the targeting agent is a peptide.

* * * * *